(12) United States Patent
Guttman et al.

(10) Patent No.: US 11,249,071 B2
(45) Date of Patent: Feb. 15, 2022

(54) REACTIVATION OF X CHROMOSOME GENES

(71) Applicant: CALIFORNIA INSTITUTE OF TECHNOLOGY, Pasadena, CA (US)

(72) Inventors: Mitchell Guttman, Los Angeles, CA (US); Chun-Kan Chen, Alhambra, CA (US); Colleen A. McHugh, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/138,208

(22) Filed: Apr. 25, 2016

(65) Prior Publication Data

US 2016/0313304 A1 Oct. 27, 2016

Related U.S. Application Data

(60) Provisional application No. 62/152,301, filed on Apr. 24, 2015.

(51) Int. Cl.
*G01N 33/50* (2006.01)

(52) U.S. Cl.
CPC ............................ *G01N 33/5023* (2013.01)

(58) Field of Classification Search
CPC .................................................. G01N 33/5023
See application file for complete search history.

(56) References Cited

U.S. PATENT DOCUMENTS

| | | | |
|---|---|---|---|
| 8,541,387 B2 | 9/2013 | Pandey et al. | |
| 2010/0022514 A1 | 1/2010 | Cho et al. | |
| 2010/0285476 A1 | 11/2010 | Rusche et al. | |
| 2011/0104177 A1* | 5/2011 | Baylin ................... | A61K 31/19 424/158.1 |
| 2012/0021519 A1 | 1/2012 | Ichida et al. | |
| 2013/0035374 A1 | 2/2013 | Morrisey | |
| 2013/0210899 A1* | 8/2013 | Wood ..................... | A61K 31/00 514/44 R |
| 2015/0252364 A1 | 9/2015 | Krieg et al. | |
| 2016/0017323 A1 | 1/2016 | Prakash et al. | |
| 2016/0030458 A1* | 2/2016 | Jones ................... | A61K 31/706 514/43 |
| 2017/0044609 A1 | 2/2017 | Guttman et al. | |
| 2019/0048339 A1 | 2/2019 | Lee et al. | |

FOREIGN PATENT DOCUMENTS

| | | |
|---|---|---|
| WO | WO 2002/085400 A1 | 10/2002 |
| WO | WO 2005/009349 A2 | 2/2005 |
| WO | WO 2008/124133 A1 | 10/2008 |
| WO | WO 2009/134418 A2 | 11/2009 |
| WO | WO 2012/016081 A2 | 2/2012 |
| WO | WO 2012/018881 A2 | 2/2012 |
| WO | WO 2014/121062 A1 | 8/2014 |
| WO | WO 2018/081661 | 5/2018 |

OTHER PUBLICATIONS

Gartler, et al. "X-Chromosome Inactivation", Encyclopedia of Life Sciences, 2005, pp. 1-7.*
Malvaez, et al. (2013) "HDAC3-selective inhibitor enhances extinction of cocaine-seeking behavior in a persistent manner." PNAS, vol. 110(7):2647-52. (Year: 2013).*
Keen, et al. (2003, Breast Cancer Res. Treat., vol. 81, No. 3:177-86). (Year: 2003).*
Csankovszki et al (J. Cell Biol. 153(4): 773-783, 2001) (Year: 2001).*
Keohane et al (Developmental Biology 180, 618-630 (1996)) (Year: 1996).*
Rumbaugh, et al. Neuropsychopharmacology (2015) 40, 2307-2316) (Year: 2015).*
Sun et al., (Proc. Nt. Acad. Sci. USA 104(39): 15282-15287, 2007) (Year: 2007).*
Xu et al., (Oncotarget 8(60): 101406-101417, 2017) (Year: 2017).*
Chueh et al., (Antioxidants & Redox Signaling 23(1): 2015) (Year: 2015).*
Rumbaugh, et al., (Neuropsychopharmacology (2015) Supplemental Information, 10 pages) (Year: 2015).*
Abdelkarim, Hazem et al.; "Photoreactive "Nanorulers" detect a novel conformation of full length HDAC3-SMRT complex in solution"; ACS Chem Biol.; Nov. 15, 2013; 8(11); 21pp.; DOI: 10.1021/cb400601g.
Berg, Thorsten; "Inhibition of transcription factors with small organic molecules"; Current opinion in chemical biology; 2008; 12; pp. 464-471.
Birmingham, Amanda et al.; "A protocol for designing siRNAs with high functionality and specificity"; Nature Protocols; 2007; vol. 2; No. 9; pp. 2068-2078.
Cerase, Andrea et al.; "Xist localization and function: new insights from multiple levels"; Genome Biology; 2015; 16; 166; 12pp.
Chen, Chun-Kan et al.; "Xist recruits the X chromosome to the nuclear lamina to enable chromosome-wide silencing"; Science; vol. 354; Issue 6311; Oct. 28, 2016; pp. 468-472; DOI: 10.1126/science.aae0047.
Chu, Ci et al.; "Systematic Discovery of Xist RNA Binding Proteins"; Cell; Apr. 9, 2015; 161; pp. 404-416.
Cong, Le et al.; "Multiplex genome engineering using CRISPR/Cas systems"; Science; Feb. 15, 2013; 339(6121); pp. 819-823.
Dickinson, Liliane A. et al.; "Inhibition of RNA polymerase II transcription in human cells by synthetic DNA-binding ligands"; Proceedings of the National Academy of Sciences; Oct. 1998; vol. 95; p. 12890-12895.
Engreitz, Jesse M. et al.; "RNA-RNA Interactions Enable Specific Targeting of Noncoding RNAs to Nascent Pre-mRNAs and Chromatin Sites"; Cell; Sep. 25, 2014; 159(1); pp. 188-199.

(Continued)

*Primary Examiner* — Richard A Schnizer
(74) *Attorney, Agent, or Firm* — Knobbe Martens Olson & Bear LLP

(57) ABSTRACT

Methods of prohibiting Xist-dependent silencing of X chromosome genes include targeting the required Xist silencing complex components including SHARP, SMRT, HDAC3, SAF-A, LBR, and the respective binding sites of SHARP, LBR, and SAF-A on Xist, thereby prohibiting Xist repression, allowing for reactivation of the silenced X chromosome genes.

10 Claims, 72 Drawing Sheets
(58 of 72 Drawing Sheet(s) Filed in Color)

Specification includes a Sequence Listing.

(56) References Cited

OTHER PUBLICATIONS

Engreitz, Jesse M. et al.; "The Xist lncRNA exploits three-dimensional genome architecture to spread across the X-chromosome"; Science; Aug. 16, 2013; 341(6147); 18pp.; doi: 10.1126/science.1237973.

Fang, Rui et al.; "Probing Xist RNA Structure in Cells Using Targeted Structure-Seq"; PLOS Genetics; Dec. 8, 2015; 29pp.

Fumagalli, Marzia et al.; "Telomeric DNA damage is irreparable and causes persistent DNA damage response activation"; Nat. Cell. Biol.; 2013; 14(4); pp. 355-365.

Gilbert, Luke A. et al.; "Genome-Scale CRISPR-Mediated Control of Gene Repression and Activation"; Cell; 159; Oct. 23, 2014; pp. 647-661.

Gupta, Nidhi et al.; "A Locked Nucleic Acid Antisense Oligonucleotide (LNA) Silences PCSK9 and Enhances LDLR Expression In Vitro and In Vivo"; PLoS ONE; May 2010; vol. 5; Issue 5; e10682; pp. 1-9.

Guttman, Mitchell et al.; "lincRNAs act in the circuitry controlling pluripotency and differentiation"; Nature; vol. 477; Sep. 15, 2011; 12pp.

Hermann, Thomas et al.; "Adaptive recognition by nucleic acid aptamers"; Science; Feb. 4, 2000; vol. 287; pp. 820-825.

International Search Report and Written Opinion for corresponding International Application No. PCT/US16/29265, dated Sep. 9, 2016, 15pp.

Khalil, Ahmad M. et al.; "Many human large intergenic noncoding RNAs associate with chromatin-modifying complexes and affect gene expression"; PNAS; vol. 106; No. 28; Jul. 14, 2009; pp. 11667-11672.

Konthur, Zoltan et al.; "Perspectives for systematic in vitro antibody generation"; Gene; vol. 364; 2005; pp. 19-29.

Kuo, Min-Hao et al.; "Roles of histone acetyltransferases and deacetylases in gene regulation"; Bioessays; 1998; vol. 20; Issue 8; pp. 615-626.

Lee, Ciaran M. et al.; "Nuclease Target Site Selection for Maximizing On-target Activity and Minimizing Off-target Effects in Genome Editing"; Molecular Therapy; Mar. 2016; 24(3); p. 475-487.

Lienert, Florian et al.; "Synthetic biology in mammalian cells: Next generation research tools and therapeutics"; Nat. Rev. Mol. Cell Biol.; Feb. 2014; 15(2); pp. 95-107.

McHugh, Colleen A. et al.; "The Xist lncRNA interacts directly with SHARP to silence transcription through HDAC3"; Nature; vol. 521; May 14, 2015; 24pp.

Mikami, Suzuka et al.; "Structural Insights into the Recruitment of SMRT by the Corepressor SHARP under Phosphorylative Regulation"; Structure; Jan. 7, 2014; vol. 22; Issue 1; pp. 35-46.

Olins, Ada L. et al.; "An in vitro model for Pelger-Huet anomaly"; Nucleus; vol. 1; Issue 6; Nov./Dec. 2010; 7pp.

Oliveira, Sabrina et al.; "Targeting tumors with nanobodies for cancer imaging and therapy"; J. Control. Release; 2013; vol. 172; Issue 3; pp. 607-617.

Patel, Dinshaw J. et al.; "Structure, recognition and discrimination in RNA aptamer complexes with cofactors, amino acids, drugs and aminoglycoside antibiotics"; Rev. Molec. Biotechnol.; vol. 74; Issue 1; Mar. 1, 2000; pp. 39-60.

Shishkin, Alexander A. et al.; "Simultaneous generation of many RNA-seq libraries in a single reaction"; Nat. Methods; Apr. 2015; 12(4); pp. 323-325.

Simon, Matthew D. et al.; "High-resolution Xist binding maps reveal 2-step spreading during X-inactivation"; Nature; Dec. 19, 2013; 504(7480); pp. 465-469.

Staarup, Ellen Marie et al.; "Short locked nucleic acid antisense oligonucleotides potently reduce apolipoprotein B mRNA and serum cholesterol in mice and non-human primates"; Nucleic Acids Res.; vol. 38; No. 20; Jul. 8, 2010; pp. 7100-7111.

Steeland, Sophie et al.; "Nanobodies as therapeutics: big opportunities for small antibodies"; Drug Discov. Today; Jul. 2016; vol. 21; Issue 7; pp. 1076-1113.

Subramanian, Romesh R. et al.; "Enhancing antisense efficacy with multimers and multi-targeting oligonucleotides (MTOs) using cleavable linkers"; Nucleic Acids Res.; Oct. 7, 2015; vol. 43; No. 19; pp. 9123-9132.

Theodosiou, Zenonas et al.; "Automated analysis of FISH and immunohistochemistry images: A review"; Cytometry; 2007; vol. 71A; pp. 439-450.

Wutz, Anton et al.; "Chromosomal silencing and localization are mediated by different domains of Xist RNA"; Nature Genet.; vol. 30; Feb. 2002; pp. 167-174.

You, Seo-Hee et al.; "Nuclear Receptor Corepressors are Required for the Histone Deacetylase Activity of HDAC3 In Vivo"; Nature Struct. Mol. Biol.; Feb. 2013; 20(2); pp. 182-187.

European Search Report issued in corresponding application EP16784113.9, dated Dec. 10, 2018, 8 pages.

Ohhata, T., et al., Lineage-specific function of the noncoding GTsix RNA forXist repression and Xi reactivation in mice, Genes & Development, Aug. 15, 2011, vol. 25, No. 16, pp. 1702-1715.

Chu, Ci., et al., Systematic Discovery of Xist RNA Binding Proteins and Supplemental Information, Cell, Apr. 1, 2015, vol. 161, No. 2, 22 pages.

International Search Report and Written Opinion dated Jan. 26, 2018 in Application No. PCT/US2017/058900.

Communication Pursuant to Article 94(3) EPC in European Patent Application No. 16784113.9, dated Feb. 7, 2020.

European Search Report issued in application EP17863915.9, dated Jun. 26, 2020, 10 pages.

Fatemi et al. "De-repressing Lnc-RNA Targeted Genes to Upregulate Gene Expression: Focus on Small Molecule Therapeutics" Mol. Ther. Nucleic Acids. Vol. 3 No. 11 (2014), e196.

Keen CJ et al.: "A novel histone deacetylase inhibitor, Scriptaid, enhances expression of functional estrogen receptor a (ER) in ER negative human breast cancer cells in combination with 5-aza 2'-deoxycytidine", Breast Cancer Research and Treatment, Springer, NY, US, vol. 81, No. 3, Jan. 1, 2003 (Jan. 1, 2003), pp. 177-186, XP008081645, ISSN: 0167-6806, DOI: 10.1023/A:1026146524737.

Monfort et al. "Identification of Spen as a Crucial Factor for Xist Function through Forward Genetic Screening in Haploid Embryonic Stem Cells" Cell Reports, vol. 12, No. 4, pp. 554-561, 2015.

Oliveria et al. "HDAC inhibition decreases XIST expression on female IVP bovine blastocysts" Journal of Reproduction and Fertility, vol. 145, No. 1 (2013), pp. 9-17.

Rumbaugh, et al. Neuropsychopharmacology (2015) 40, 2307-2316).

Rumbaugh, et al. Neuropsychopharmacology (2015) Supplemental Information, 10 pages.

Sun et al., (Proc. Nt. Acad Sci. USA 104(39): 15282-15287, 2007).

Xu et al., (Oncotarget 8(60): 101406-101417, 2017).

Chueh et al., (Antioxidants and redox Signaling 23(1): 2015).

* cited by examiner

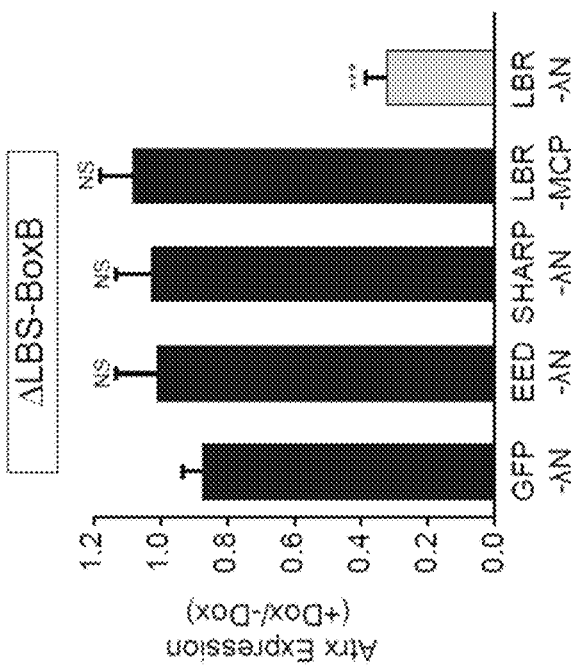
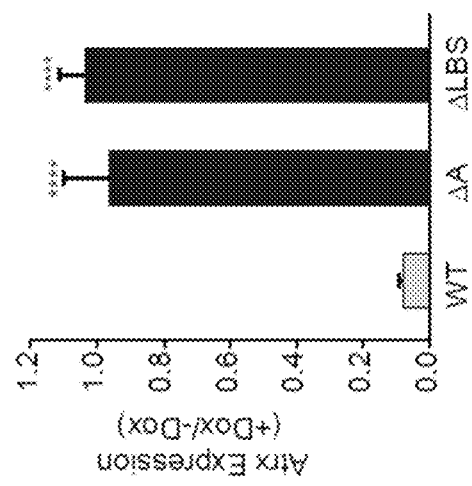
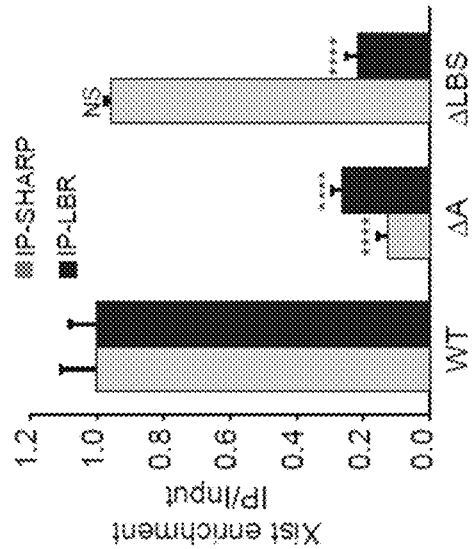
FIG. 3B
FIG. 3C
FIG. 3D

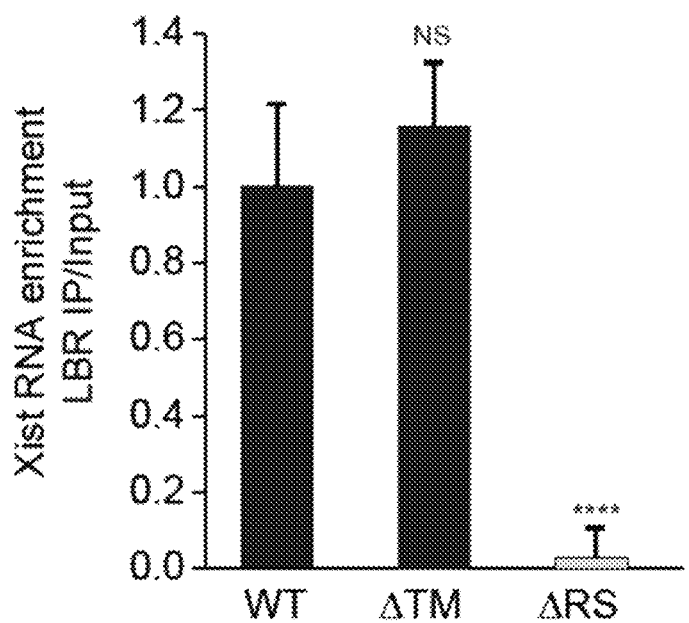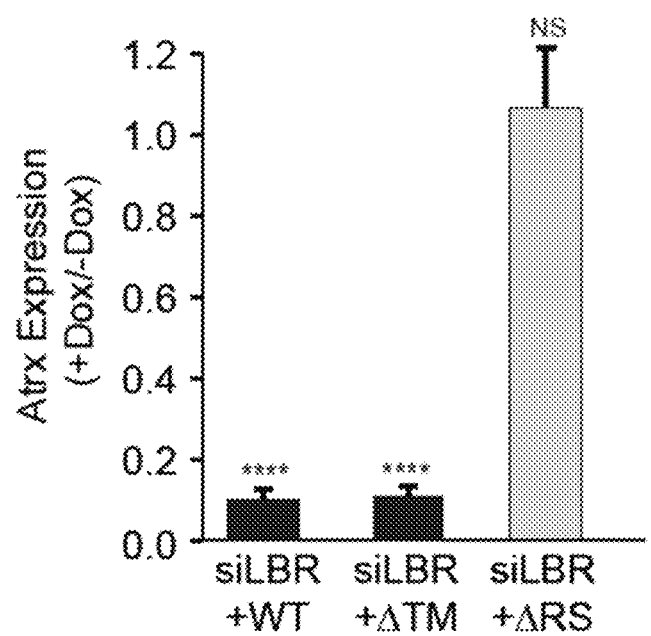

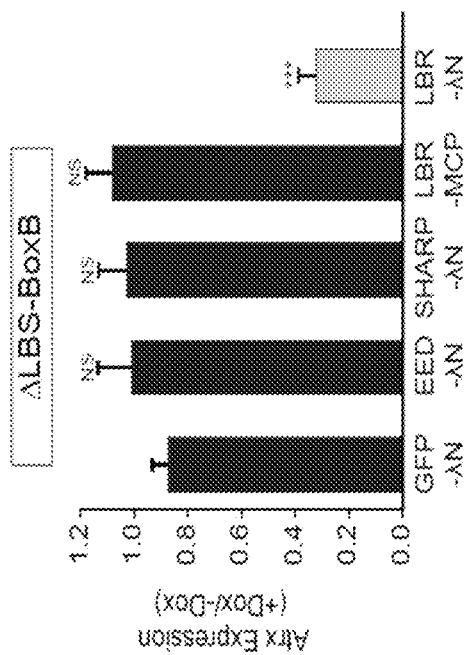
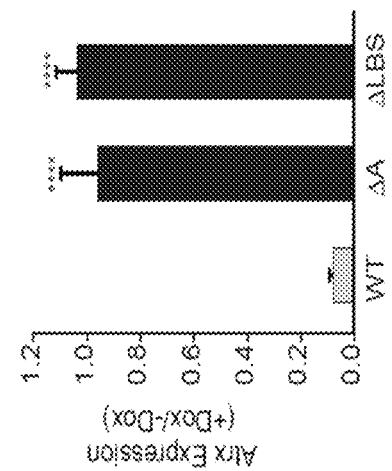
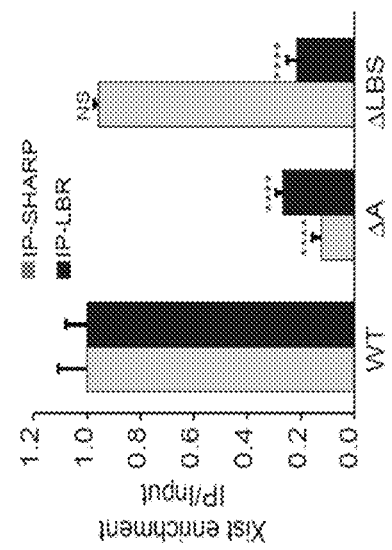

REACTIVATION OF X CHROMOSOME GENES

CROSS-REFERENCE TO RELATED APPLICATION(S)

The present application claims priority to and the benefit of U.S. Provisional Application Ser. No. 62/152,301 filed on Apr. 24, 2015, entitled "Targeting and Synthesizing Long Non-Coding RNA Regulatory Interactions," the entire content of which is incorporated herein by reference.

STATEMENT REGARDING FEDERALLY SPONSORED RESEARCH OR DEVELOPMENT

This invention was made with government support under Grant No. OD012190 awarded by the National Institutes of Health. The government has certain rights in the invention.

INCORPORATION BY REFERENCE

The instant application contains a Sequence Listing which has been submitted in ASCII format via EFS-Web and is hereby incorporated by reference in its entirety. Said ASCII copy, was created on Jul. 11, 2016, is named 1224396SEQ-LISTING.txt, and is 2,392 bytes in size.

BACKGROUND

Many long non-coding RNAs (lncRNAs) affect gene expression, but the mechanisms by which they act are still largely unknown. One of the studied lncRNAs is Xist, which is required for transcriptional silencing of one X-chromosome during development in female mammals. Xist initiates XCI by spreading across the future inactive X-chromosome, excluding RNA Polymerase II (PolII), and repositioning active genes into transcriptionally silenced nuclear compartments. All of these roles—localization, RNA PolII exclusion, and repositioning—are required for proper silencing of transcription during the initiation of XCI.

Despite extensive efforts to define the mechanism of Xist-mediated transcriptional silencing, proteins required for Xist-mediated silencing have not been identified. The main challenge is the lack of methods to comprehensively define the proteins that directly interact with the Xist lncRNA in the cell.

SUMMARY

In some embodiments of the present invention, a method of identifying a molecule that prohibits Xist-dependent silencing of X chromosome genes includes administering a candidate molecule to a cell having at least one Xist-dependent X chromosome gene or to a cell having an Xist-dependent autosome gene, the candidate molecule being selected to target Xist-dependent activity of a component in an Xist silencing complex, the component being a protein or a long noncoding RNA (lncRNA) selected from SHARP, SMRT, HDAC3, SAF-A, LBR, the binding site of SHARP on Xist, the binding site of LBR on Xist, or the binding site of SAF-A on Xist; and measuring expression activity of the at least one Xist-dependent X chromosome gene or the Xist-dependent autosome gene, in which increased expression activity of the at least one Xist-dependent X chromosome gene or the Xist-dependent autosome gene identifies the candidate molecule as a molecule that prohibits Xist-dependent silencing of X chromosome genes.

In some embodiments, a method of identifying a candidate that reactivates expression of silenced X chromosome genes or a silenced Xist-dependent autosome gene, includes identifying a molecule that prohibits Xist-dependent silencing of X chromosome genes.

In some embodiments, a method of prohibiting Xist-dependent silencing of at least one X chromosome gene or Xist-dependent silencing of an autosomal gene, includes administering a molecule to a cell having at least one X chromosome gene or an Xist-dependent autosome gene, the molecule being selected to prohibit or disrupt an interaction selected from Xist long noncoding RNA (lncRNA) and SHARP, Xist lncRNA and LBR, Xist lncRNA and SAF-A, SHARP and SMRT, SMRT and HDAC3, or HDAC3 enzymatic activity.

In some embodiments of the present invention, method of prohibiting Xist-dependent silencing includes is selected from molecules that disrupt a gene encoding for Xist lncRNA, LBR, SAF-A, SHARP, SMRT or HDAC3; molecules that regulate transcription of Xist lncRNA, LBR, SAF-A, SHARP, SMRT or HDAC3; molecules that target Xist lncRNA or the mRNA of LBR, SAF-A, SHARP, SMRT, or HDAC3 selected from the group consisting of modified antisense oligonucleotides, small interfering RNA (siRNA), small hairpin RNA (shRNA), and micro RNA (miRNA); antibodies, small molecules, nucleic acid aptamers, or peptides that bind or inhibit the binding or enzymatic activity of LBR, SAF-A, SHARP, SMRT or HDAC3; or molecules that disrupt the binding of Xist with SHARP, Xist with LBR, or Xist with SAF-A.

In some embodiments, a method of reactivating expression of X chromosome genes silenced by Xist includes inhibiting one of the required components of the Xist silencing complex. In some embodiments, the method of reactivating expression of X chromosome genes silenced by Xist includes inhibiting one of the required components of the Xist silencing complex in combination with inhibition of DNA methylation.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 3B is a graph plotting Xist RNA enrichment level measured by RT-qPCR after immunoprecipitation of endogenous LBR or SHARP in wild-type, ΔA, or ΔLBS cells, in which error bars represent the SEM from four independent IP experiments, NS: not significant, * p-value<0.005, ** p-value<0.001 relative to wild type cells by an unpaired two-sample t-test, according to embodiments of the present invention.

FIG. 3C is a graph plotting relative Atrx mRNA expression in wild-type, ΔA, or ΔLBS-Xist cells, NS: not significant, * p-value<0.005, ** p-value<0.001 relative to wild type cells by an unpaired two-sample t-test, according to embodiments of the present invention.

FIG. 3D is a graph plotting expression of ΔLBS-Xist with a 3x-BoxB fusion (ΔLBS-BoxB) along with expression of GFP-λN (control), EED-λN, SHARP-λN, or LBR-λN; as an additional control, LBR was expressed fused with the bacteriophage MS2 Coat Protein (LBR-MCP), NS: not significant, * p-value<0.005, ** p-value<0.001 relative to cells transfected with GFP-λN (d) by an unpaired two-sample t-test, according to embodiments of the present invention.

FIG. 12A is a graph plotting enrichment of the Xist lncRNA after immunoprecipitation from a sample of pSM33 male cells. FIG. 12B is graph plotting enrichment over IgG from an immunoprecipitation of SHARP performed from a sample of UV-crosslinked females ES cells that were treated with retinoic acid for 24 hours in which the levels of recovered Xist lncRNA (black bars), Neat1 lncRNA (white bars), and 45S pre-ribosomal RNA (gray bars) were measured by RT-qPCR, and enrichment of each RNA after capture with anti-SHARP antibody was calculated relative to the level of RNA captured with IgG control antibody. FIG. 12C is graph plotting enrichment of various lncRNAs after immunoprecipitation in pSM33 male cells—including Neat1, Malat1, Firre, and Tug1—are shown. FIG. 12D is a graph plotting the enrichment of various mRNA controls after immunoprecipitation in pSM33 male cells—including Oct4, Nanog, Stat3, and Suz12—as shown.

FIG. 21B is a graph plotting Xist RNA enrichment level after immunoprecipitation of a 3×-FLAG tagged LBR normalized to input RNA levels in cells expressing full-length LBR (WT), ΔRS-LBR, or ΔTM-LBR according to methods described herein, with error bars representing the SEM from three independent IP experiments, according to embodiments of the present invention.

FIG. 21C is a graph plotting the relative Atrx mRNA expression upon siRNA knockdown of the endogenous LBR and expression of a cDNA construct expressing the full length LBR (WT), ΔTM-LBR, or ΔRS-LBR, according to embodiments of the present invention.

FIG. 24B is graph plotting the Xist RNA enrichment level measured by RT-qPCR after immunoprecipitation of endogenous LBR or SHARP in wild-type, ΔA, or ΔLBS cells, with error bars representing the SEM from four independent IP experiments, with error bars representing the SEM across 50 individual cells, NS: not significant, * p-value<0.005, ** p-value<0.001 relative to wild type cells, according to embodiments of the present invention.

FIG. 24C is a graph plotting the relative Atrx mRNA expression in wild-type, ΔA, or ΔLBS-Xist cells, with error bars representing the SEM across 50 individual cells, NS: not significant, * p-value<0.005, ** p-value<0.001 relative to wild type cells, according to embodiments of the present invention.

FIG. 24D is a graph plotting expression of ΔLBS-Xist with a 3×-BoxB fusion (ΔLBS-BoxB) along with expression of GFP-λN (control), EED-λN, SHARP-λN, or LBR-λN, with LBR fused with the bacteriophage MS2 Coat Protein (LBR-MCP) as a control, with error bars representing the SEM across 50 individual cells, NS: not significant, * p-value<0.005, ** p-value<0.001 relative to cells transfected with GFP-λN, according to embodiments of the present invention.

DETAILED DESCRIPTION

Figure 1A:
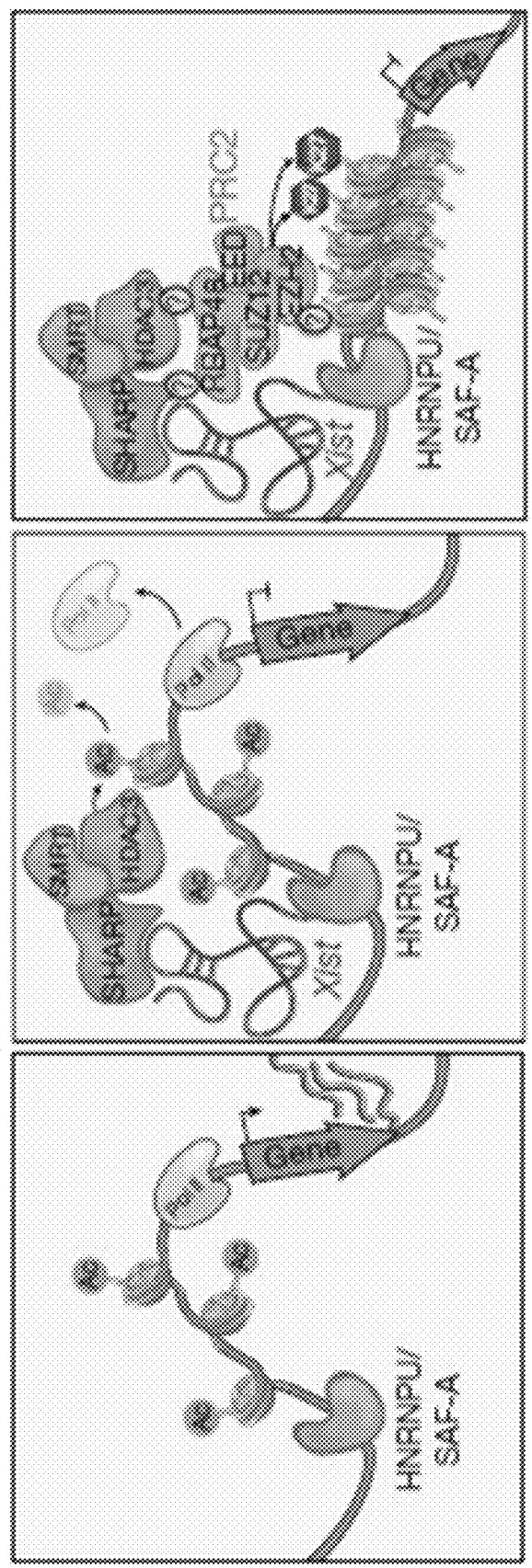
FIG. 1A is a schematic depicting a model for Xist-mediated transcriptional silencing and recruitment of PRC2 across the X-chromosome, according to embodiments of the present invention.
Figure 1B:
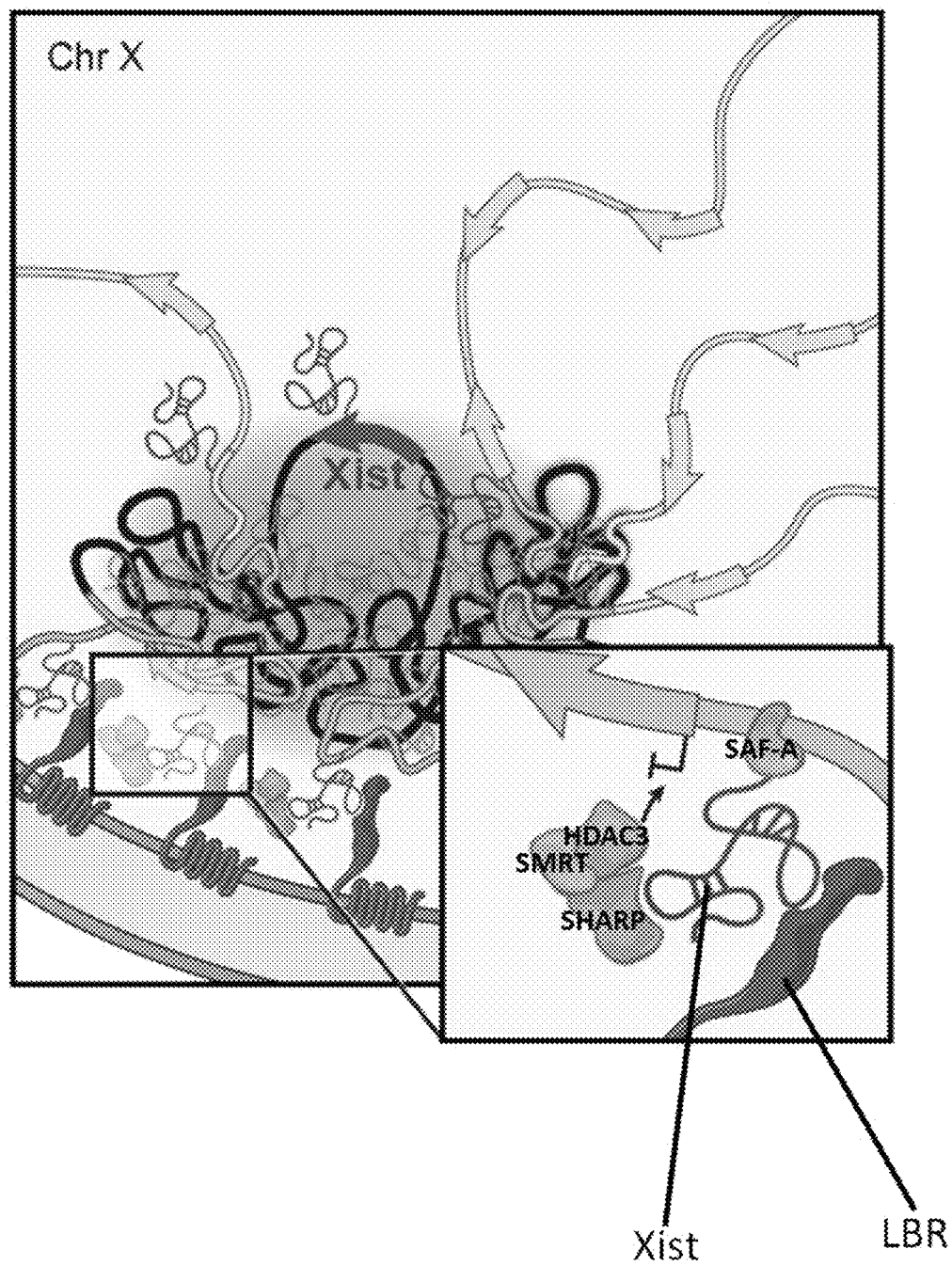
FIG. 1B is a schematic depicting a model for how Xist-mediated recruitment to the nuclear lamina enables spreading to active genes and transcriptional silencing on the X chromosome, according to embodiments of the present invention.

The Xist long noncoding RNA (lncRNA) mediates X chromosome inactivation (XCI) in mammalian cells in a process that includes chromosome-wide silencing and remodeling of the 3-dimensional structure of the X chromosome. According to embodiments of the present invention, the protein components that interact with Xist lncRNA and are required for Xist-dependent transcriptional silencing of X chromosome genes include the SHARP, SMRT, HDAC3, SAF-A, and LBR proteins. As depicted in FIG. 1A, Xist lncRNA directly binds to SHARP, SHARP directly binds SMRT, and HDAC3 directly binds SMRT. As also shown in FIG. 1A, several other regions of Xist bind to the SAF-A protein, and SAF-A binds directly to genomic DNA of the X chromosome gene. As shown in FIG. 1B, the LBR transmembrane protein directly binds to Xist.

Using these identified protein interactions of Xist and the requirement of each of these proteins for Xist-dependent silencing of X chromosome genes, embodiments of the present invention include targeting of any one of these identified Xist interactions in order to inhibit, disrupt, or prevent Xist-dependent silencing of X chromosome genes.

As used herein, SHARP refers to the SMRT and HDAC associated repressor protein. The SHARP protein is also known as Spen or MINT and is a Spen (split end) protein.

As used herein, SMRT refers to the silencing mediator of retinoid and thyroid receptors protein and is also known as NCor2.

As used herein, HDAC3 refers to the enzymatic histone deacetylase 3 protein.

As used herein, SAF-A refers to the scaffold attachment factor A protein. SAF-A is also known as HNRNPU (heterogeneous nuclear ribonucleoprotein U).

As used herein, LBR refers to the Lamin B Receptor protein, a transmembrane protein that is an integral part of the nuclear lamina.

As used herein "silencing," "silenced," and like terms refer to the repression of expression activity of a gene. For example a silenced gene is not expressed, and does not undergo transcription.

As used herein, "gene" refers to any sequence of DNA nucleotides that is capable of being transcribed. As such a gene includes DNA that encodes for proteins and noncoding DNA that undergoes transcription. The gene may be in the genome (part of the chromosomes) of a cell, or the gene may be expressed exogenously on a plasmid vector in the cell. A chromosomal gene may be a naturally occurring gene or a gene that has been incorporated into the genome of the cell.

Figure 2:
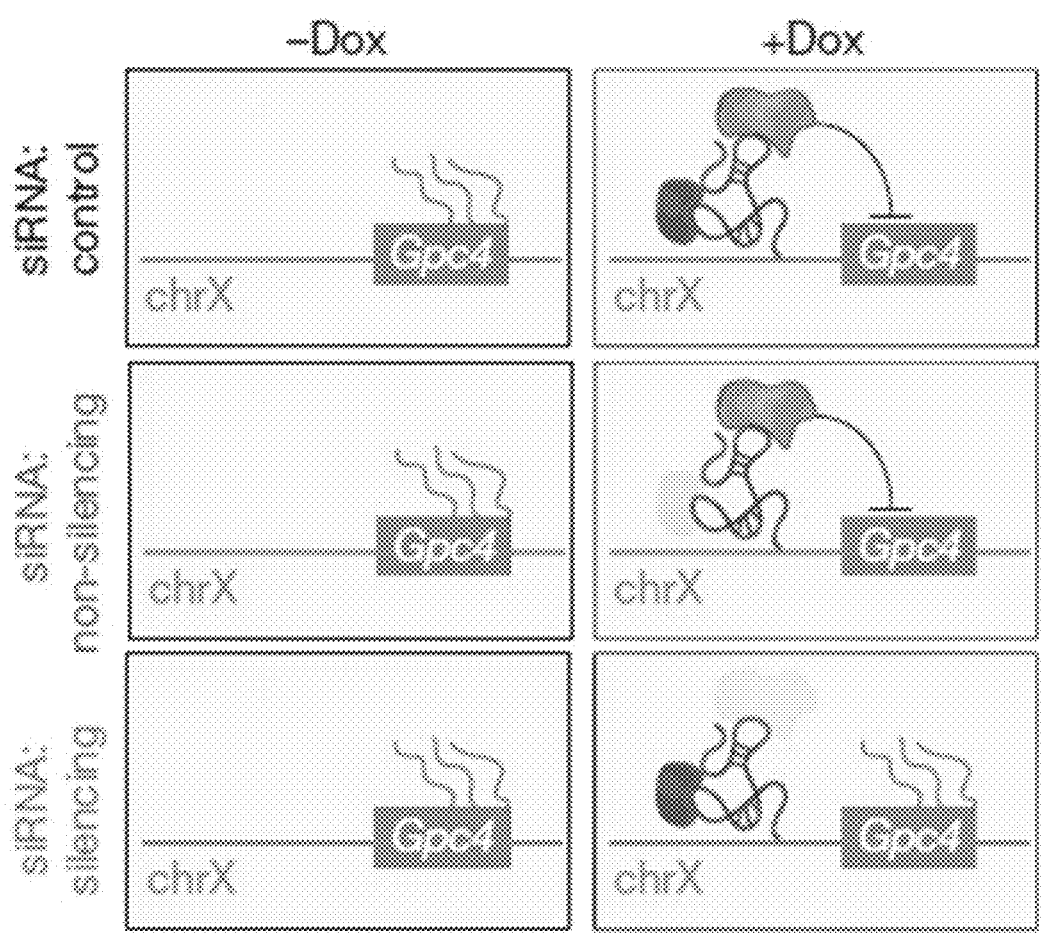
FIG. 2 is a schematic depicting a method of screening for Xist-mediated gene silencing for knockdown of control (top), non-silencing proteins (middle), or silencing proteins (bottom), according to embodiments of the present invention.

As used herein, "prohibits," "prohibition," and like terms refer to the inhibition, disruption, or prevention of an activity. In some embodiments of the present invention, prohibition of Xist-dependent gene silencing includes inhibition, disruption, reactivation of silenced transcription, or the prevention (preclusion) of transcription/expression of an Xist-dependent gene. Prevention of silencing is depicted in FIG. 2 in which the Xist expression is controlled by a tetracycline-inducible promoter from its endogenous locus. The addition of doxycycline induces expression of Xist which under wild type conditions (e.g., interaction with the Xist silencing complex components) silences X chromosome genes or any engineered Xist-dependent gene. With controlled Xist expression, Xist-dependent silencing is shown to be prevented in that Xist is expressed in the presence of doxycycline (dox+), but inhibition of one of the Xist silencing complex components results in transcription. This prevention (i.e., prohibition or preclusion) of silencing is shown, for example, in FIGS. 3C, 3D, 4, 5A, 6B and 6D, in which the expression of the indicated gene would have been silenced if the inhibition method or molecule was not administered.

As used herein, "administering," and like terms refer to the act of providing. In some embodiments of the present invention, the administering of an inhibitor molecule or a candidate molecule to a cell includes providing the molecule to a cell. This act of providing or administering includes the necessary methods and incubation to provide the molecule to and into the cell.

As used herein, "expression activity," and like terms refer to any and all activity that is associated with a gene. Examples of expression activity include modifications of chromatin, recruitment of transcription factors, chromatin regulators, the presence of RNA II polymerase, activation of transcription including interactions upstream or downstream of the transcription start site (e.g., enhancer, operator, or promoter regions). Examples of expression activity include any factors required for transcription of the gene or for translation of the mRNA transcript.

As used herein, the phrase "measuring expression activity" refers to any method that is capable of determining if an Xist-dependent gene can undergo expression. Measuring of expression activity may include measuring recruitment of RNA Polymerase II (RNA Pol II). Measuring of expression activity may include measuring transcription (e.g., the levels of mRNA) of an Xist-dependent gene or measuring translation (e.g., protein levels) or the protein products of an Xist-dependent gene.

As used herein, the phrase "Xist-dependent X chromosome gene" refers to any X chromosome gene that undergoes X chromosome inactivation. As almost all X chromosome genes are silenced by Xist, these X chromosome genes are Xist-dependent—i.e, X chromosome genes are silenced by Xist-mediated repression.

As used herein, the phrase "Xist-dependent autosome gene" refers to any gene that has been engineered to incorporate Xist in which expression of the Xist-dependent autosome gene requires inhibition of Xist to reverse or prohibit the Xist-mediated silencing of the autosome gene.

As used herein the "Xist-silencing complex" refers to all of the required components for Xist-mediated gene silencing which include: SHARP, SMRT, HDAC3, SAF-A, LBR, the binding site of SHARP on Xist, the binding site of LBR on Xist, and the binding site of SAF-A on Xist.

As used herein, "reactivation" and like terms refer to the reversal of gene silencing. For example, reactivation of a silenced gene refers to the "unsilencing" of the gene, thereby allowing for expression of the gene. For example, a reactivated silenced gene is expressed and therefore undergoes transcription and translation.

Targeting of Xist Silencing Complex Interactions

According to embodiments of the present invention, prohibiting any one of the direct interactions in the Xist silencing complex results in the inhibition or preclusion of Xist-mediated gene silencing. For example, Xist-mediated silencing is inhibited or prevented by prohibiting any one of the direct interactions selected from SHARP with SMRT, SMRT with HDAC3, SAF-A with Xist, LBR with Xist, or SHARP with Xist. According to embodiments of the present invention, methods for prohibiting Xist-mediated gene silencing include any of the many possible methods and/or molecules for prohibiting the required interactions in the Xist silencing complex. For example, in some embodiments, a method for identifying a molecule that prohibits Xist-dependent silencing of X chromosome genes includes administering a candidate molecule selected to target Xist-dependent activity of a component in an Xist silencing complex. The component may be a protein or a long noncoding RNA (lncRNA) selected from SHARP, SMRT, HDAC3, SAF-A, LBR, the binding site of SHARP on Xist, the binding site of LBR on Xist, or the binding site of SAF-A on Xist. The molecule may be administered to a cell having at least one Xist-dependent X chromosome gene or to a cell having an Xist-dependent autosome gene. Prohibiting of Xist-dependent gene silencing is defined as any observed amount of transcription in cell administered an a candidate molecule relative to a cell that is not administered the candidate molecule.

According to embodiments of the present invention, molecules that target any of the required Xist silencing complex interactions are useful for their ability to either prevent or reverse the silencing of X chromosome genes or any Xist-mediated silenced gene.

Embodiments of the present invention include methods for identifying a molecule that prohibits Xist-mediated gene silencing by selecting molecules that are capable of targeting the required Xist silencing complex interactions.

Embodiments of the present invention include molecules that disrupt a gene encoding for a component of the Xist silencing complex. For example, the molecules may include those that disrupt a gene or part of a gene encoding for any of SHARP, SMRT, HDAC3, SAF-A, LBR, the binding site of SHARP on Xist, the binding site of LBR on Xist, or the binding site of SAF-A on Xist. Methods for gene disruption include CRISPR/Cas9, TALENS, zinc-finger nuclease (ZFN) proteins, and nucleases that specifically target the gene or part of a gene as described in Lienert et al., 2014, *Nat. Rev. Mol. Cell Biol.,* 15:95-107, and Lee et al., 2016, *Molec. Therapy,* 24:475-487, the entire contents of both of which are herein incorporated by reference.

Figure 3A:
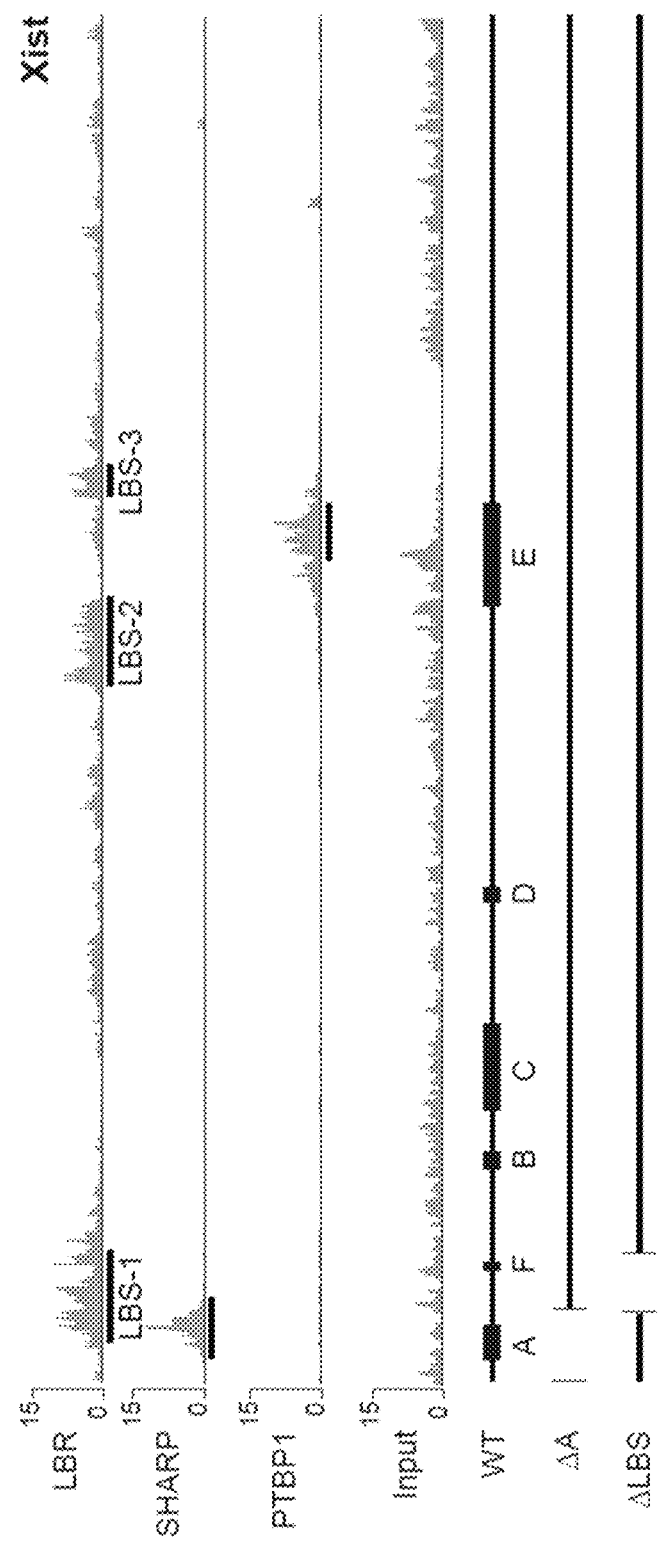
FIG. 3A shows CLIP data plotted across the Xist RNA for LBR, SHARP, and PTBP1 proteins, according to embodiments of the present invention in which the values represent fold-enrichment at each position on Xist normalized to a size-matched input RNA control as following methods described herein, and input represents the total RNA control for the LBR CLIP sample; bottom: A schematic of the annotated repeat regions on the Xist RNA (WT) and the locations of the deleted regions in the ΔA (nucleotides 1-937) and ΔLBS (nucleotides 898-1682) Xist RNA.

For example, as shown in FIG. 3A, one LBR binding site (LBS-1) on Xist was deleted using CRISPR-mediated knock out to generate ΔLBS Xist. Using an X-chromosome silencing assay, cell expression of the Atrx gene was measured using wild type (WT) Xist and ΔLBS Xist. As shown in FIG. 3C, cells with WT Xist did not express Atrx, and cells with ΔLBS Xist inhibited Xist-mediated silencing and expressed Atrx.

Figure 4:
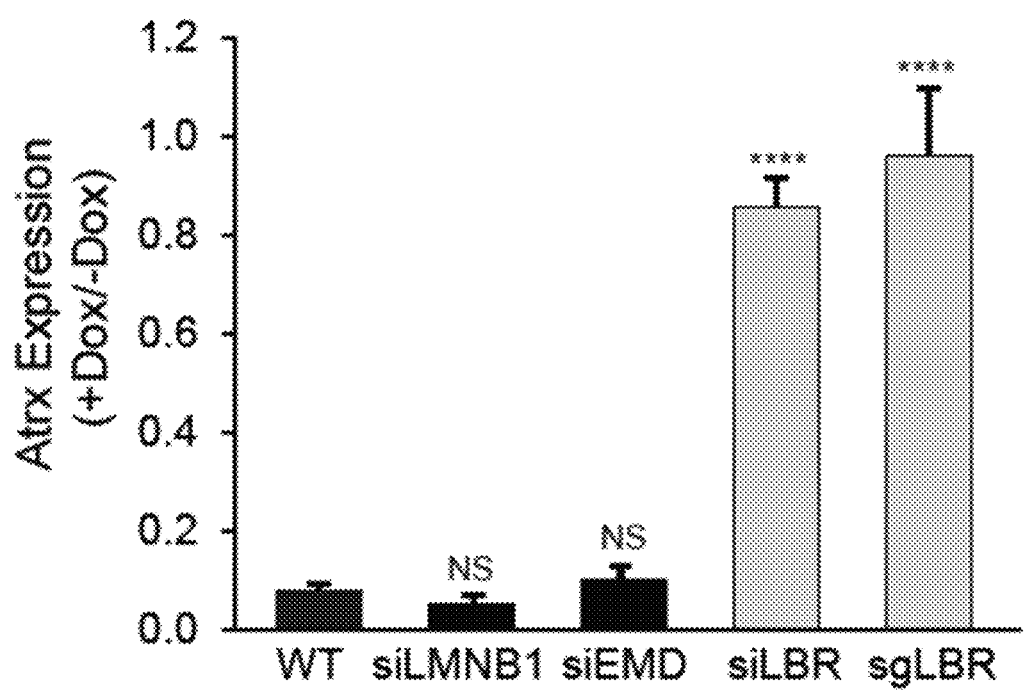
FIG. 4 is graph plotting the number of mRNA molecules of Atrx (an X chromosome gene) after induction of Xist (+dox) relative to levels prior to Xist induction (−dox) upon knock down of various nuclear lamina proteins with WT: scrambled siRNA control, siEMD: Emerin knockdown. siLMNB1: Lamin B1 knockdown. sgLBR: Knockdown of LBR using an sgRNA and dCas9-KRAB following methods disclosed herein, according to embodiments of the present invention.

Embodiments of the present invention include molecules that regulate transcription of a gene encoding for the protein or lncRNA component. Non-limiting examples include chromatin regulators, transcriptional factors, and small molecules that modulate the transcription of the gene encoding for the protein or lncRNA component. For example, the Kruppel-associated box repressor (KRAB) is a chromatin regulator that regulates gene expression by mediating chromatin states. KRAB was modified specifically to target the transcription of LBR using the CRISPR-Cas9 method. As such, cells expressing dCas9-KRAB and a single guide RNA (sgRNA) targeted near the transcription start site of LBR, knocks down expression of LBR and results in expression of the Artx gene despite the induction of (or presence of) Xist. The expression of Artx in cells with dCas9-KRAB mediated knockdown of LBR (sgLBR) with induced Xist expression is shown in FIG. 4.

Embodiments of the present invention include molecules that directly contact and inhibit or degrade the mRNA that encodes the protein component. For example, molecules that directly contact and inhibit mRNA of the protein component or directly contact a binding site on the lncRNA may be selected from antisense oligonucleotides, small interfering RNA (siRNA), small hairpin RNA (shRNA), CRISPR (sgRNA), and micro RNA (miRNA) targeted against mRNA of SHARP, SMRT, HDAC3, LBR, or SAF-A.

In some embodiments, antisense oligonucleotides (ASO) may be designed to target specific DNA or RNA regions corresponding to either regulator sites for each of the Xist silence complex components, thereby wholly or partially precluding expression of the component. The genomic DNA or the mRNA of SHARP, SMRT, HDAC3, LBR, or SAF-A may be targeted with antisense DNA or RNA oligonucleotides, respectively. For Xist lncRNA, in addition to the targeting of the gene with antisense DNA, the functional lncRNA may itself be targeted with antisense RNA oligonucleotides designed to specifically target and bind the RNA nucleotides of Xist that correspond to the binding sites for one of LBR binding sites (LBS1, LBS2, or LBS3), SAF-A, and/or SHARP. The LBS1 includes nucleotides 535 to1608 on Xist, LBS2 includes nucleotides 9506-10245 on Xist, and LBS3 includes nucleotides 11732 to 11956 on Xist. The SHARP binding site on Xist includes nucleotides 317 to 1056 on Xist. Antisense oligonucleotides targeted to any of these LBR, SAF-A or SHARP binding sites do not need to bind the entire binding region to disrupt or abolish the binding of the corresponding Xist complex component. While short ASOs suffer from specificity, long ASOs suffer from stability and proper delivery. ASOs may be modified to include high affinity RNA binders (e.g., locked nucleic acids (LNAs)) as well as chemical modifications. In some embodiments of the present invention, an ASO targeted to any of the Xist silencing complex components is 8 to 80 subunits (or nucleotides) in length. Design and modification of antisense oligonucleotides is described, for example, in Subramanian et al., 2015, Nucleic Acids Res. 43; 9123-9132; Staarup et al., 2010, Nucleic Acids Res., 38:7100-7111; Gupta et al., 2010, PLoS ONE, 5:e10682, 1-9; Prakash et al., US2016/0017323; and Krieg et al., US2015/0252364, the entire contents of all of which are herein incorporated by reference. Specific ASOs targeting SMRT are described in Pandey et al., U.S. Pat. No. 8,541,387, the entire content of which is herein incorporated by reference.

Figure 5A:
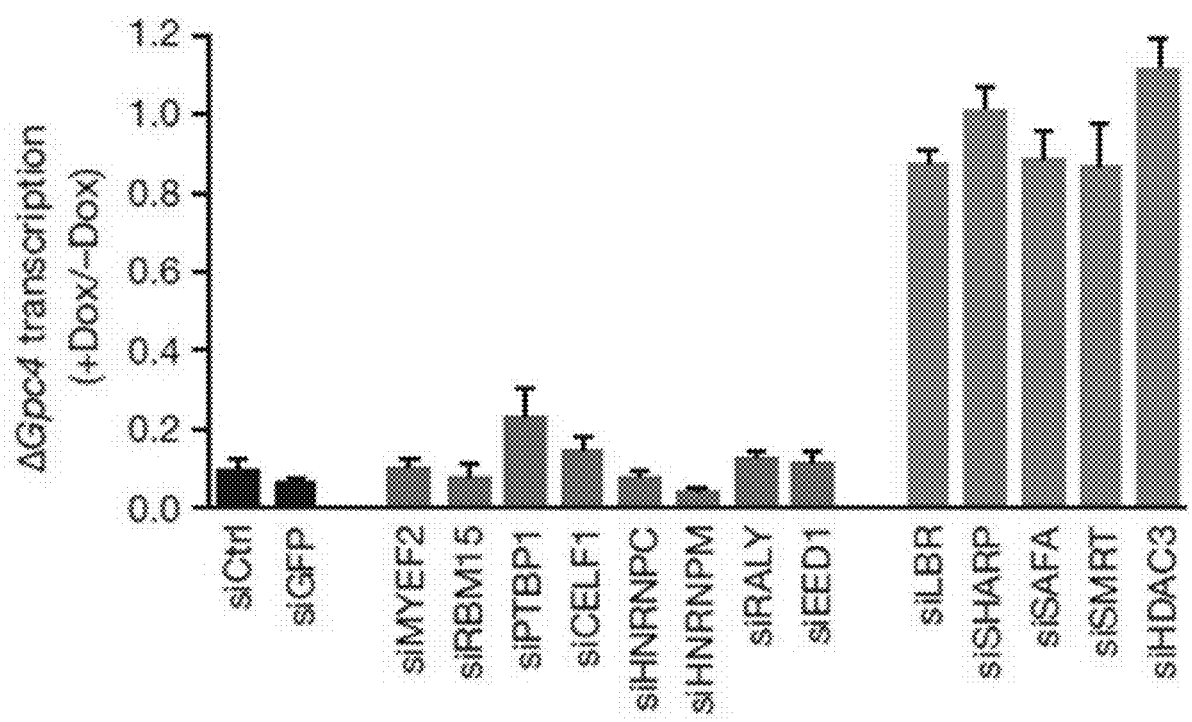
FIG. 5A is a graph plotting Gpc4 mRNA levels after induction of Xist (+dox) normalized to Gpc4 levels before Xist induction (−dox), with error bars: standard error of the mean across 50 cells from one experiment. siCtrl: scrambled siRNA control, and each siRNA as indicated, according to embodiments of the present invention.
Figure 5B:
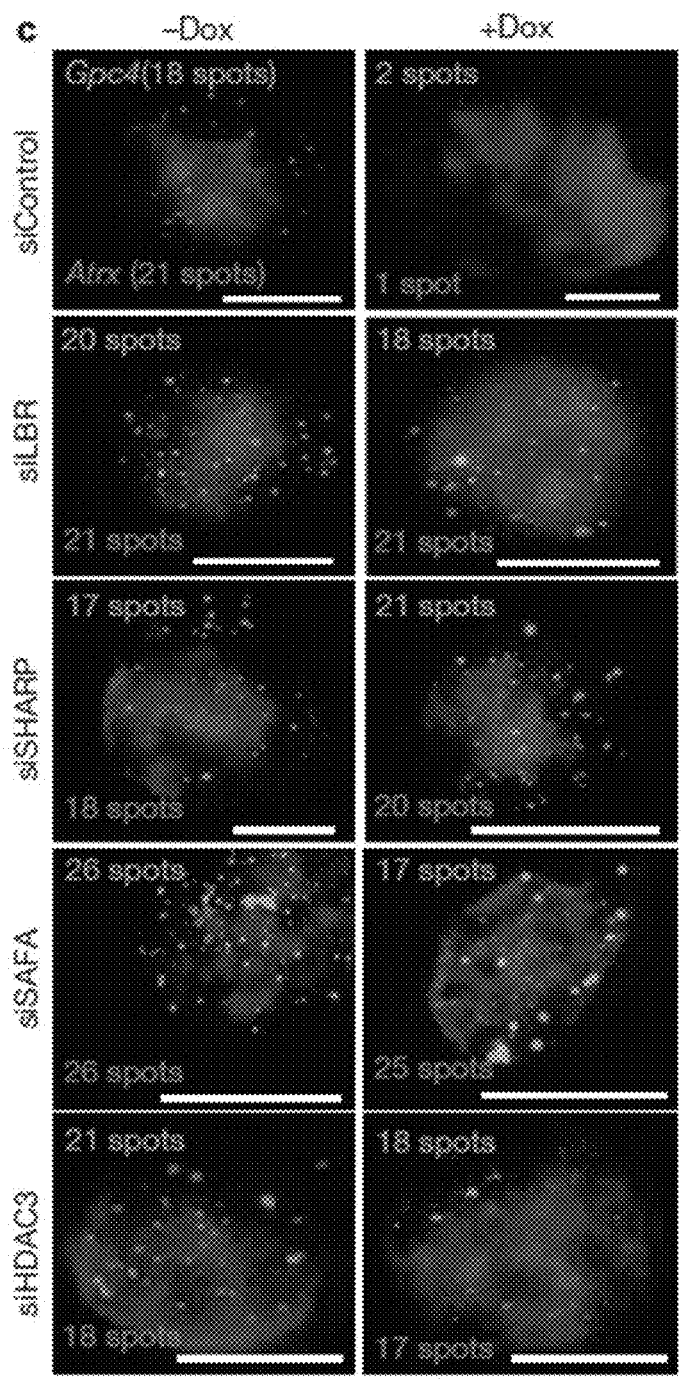
FIG. 5B shows images of individual cells for two X-linked mRNAs, Gpc4 (green) and Atrx (red), and DAPI (blue) after treatment with different siRNAs (rows), where the number of identified mRNAs is shown, with scale bars, 5 micrometers, according to embodiments of the present invention.
Figure 6A:
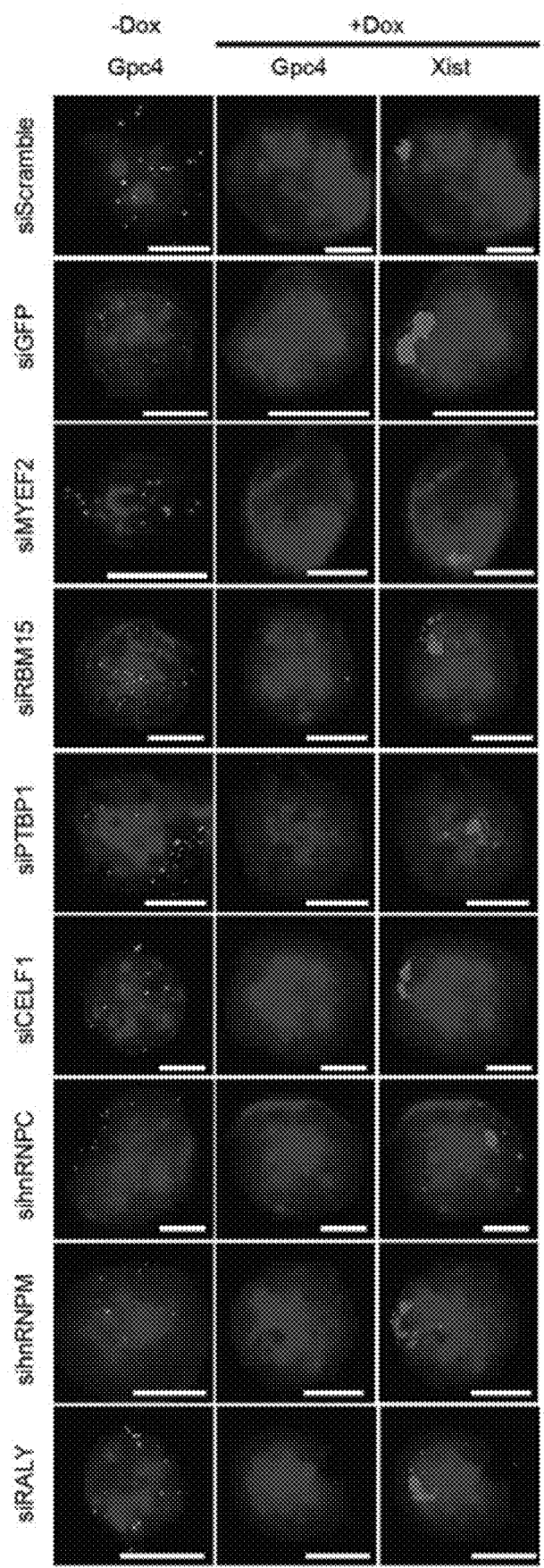
FIG. 6A shows representative images showing staining of DAPI (blue), Xist (red), and Gpc4 (green) for different siRNA knockdown in male ES cells prior to Xist induction (−Dox; left) or after Xist induction for 16 hours (+Dox; middle and right), according to embodiments of the present invention.
Figure 6A:
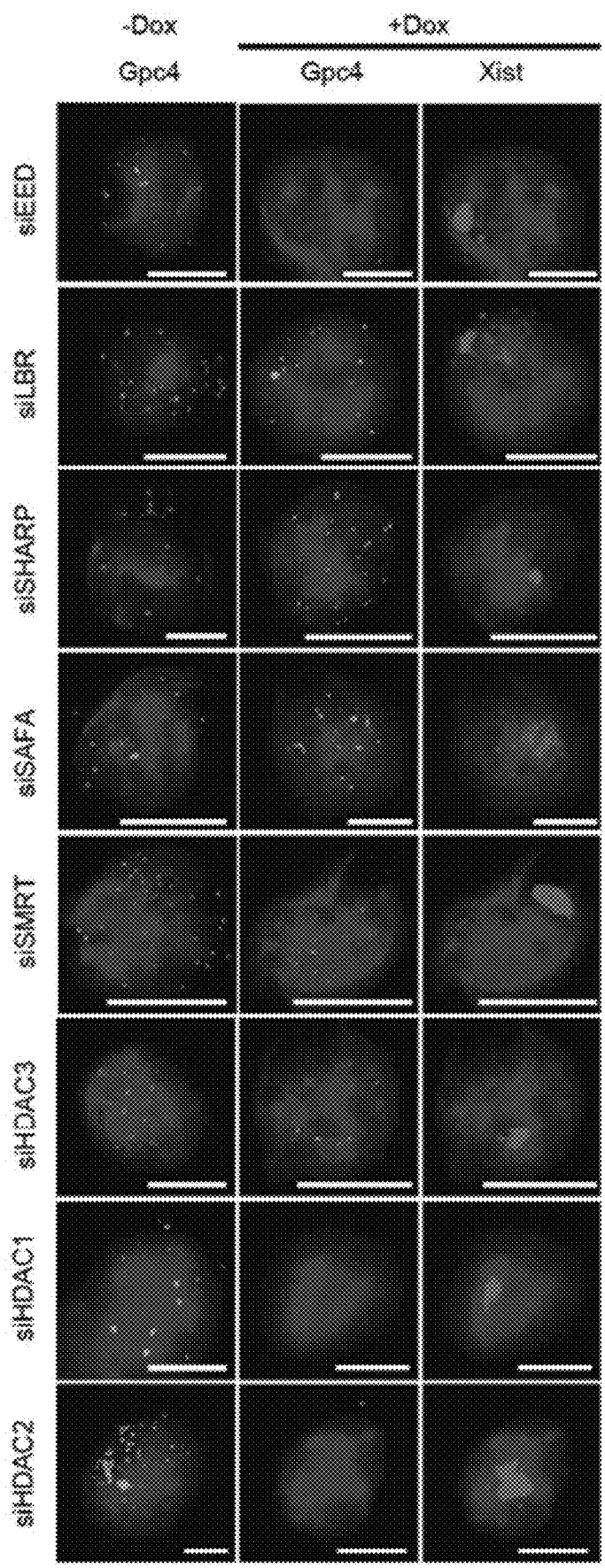
Figure 6B:
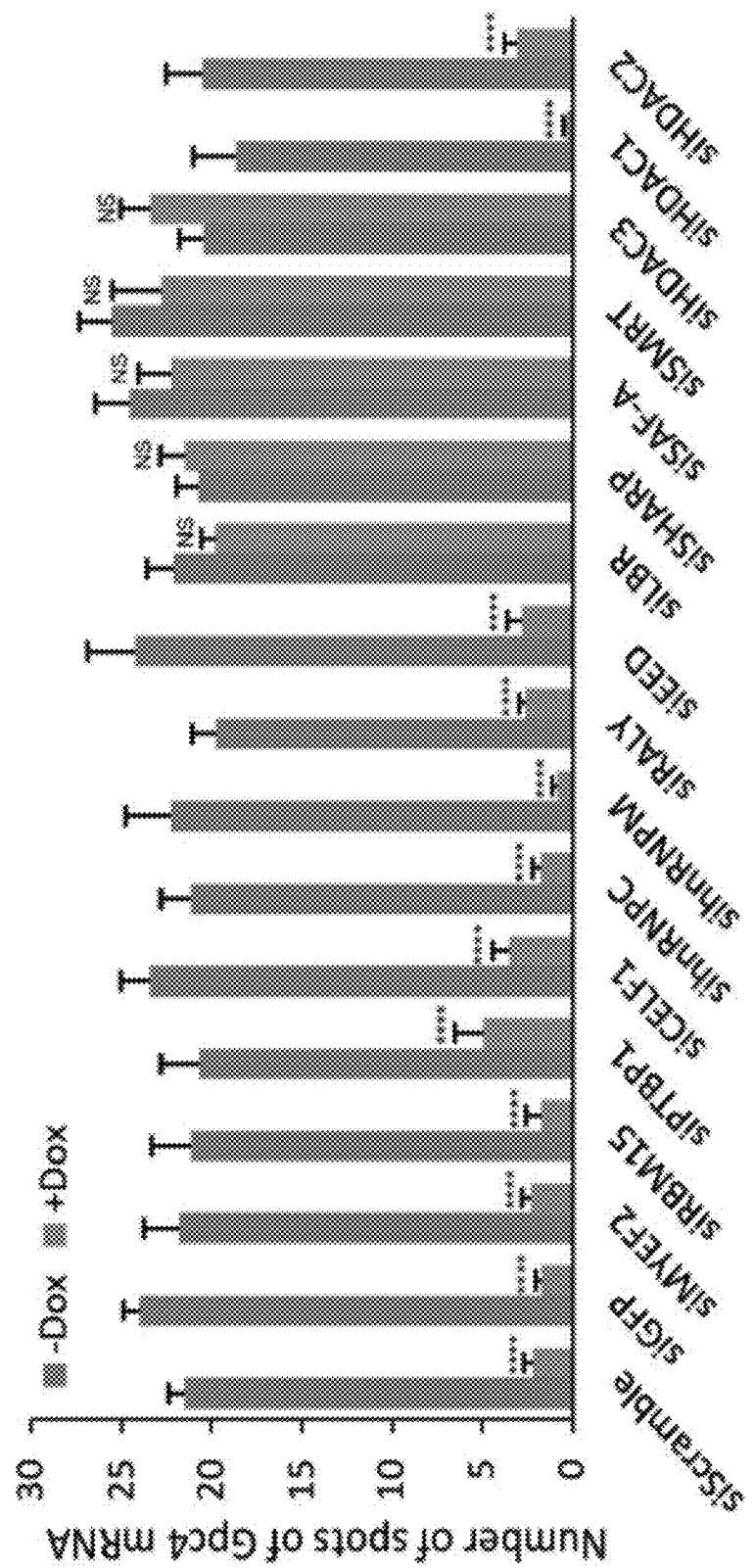
FIG. 6B shows quantification of the copy number of Gpc4 in −Dox and +Dox cells after knockdown with siRNAs targeting different mRNAs where error bars represent the standard error of the mean across 50 individual cells from one experiment, and NS: not significantly different between +Dox and −Dox cells; **** represents values with a p-value<0.001 between +Dox and −Dox cells based on an unpaired two-sample t-test with scale bars on the images represent 5 μm, according to embodiments of the present invention.
Figure 6C:
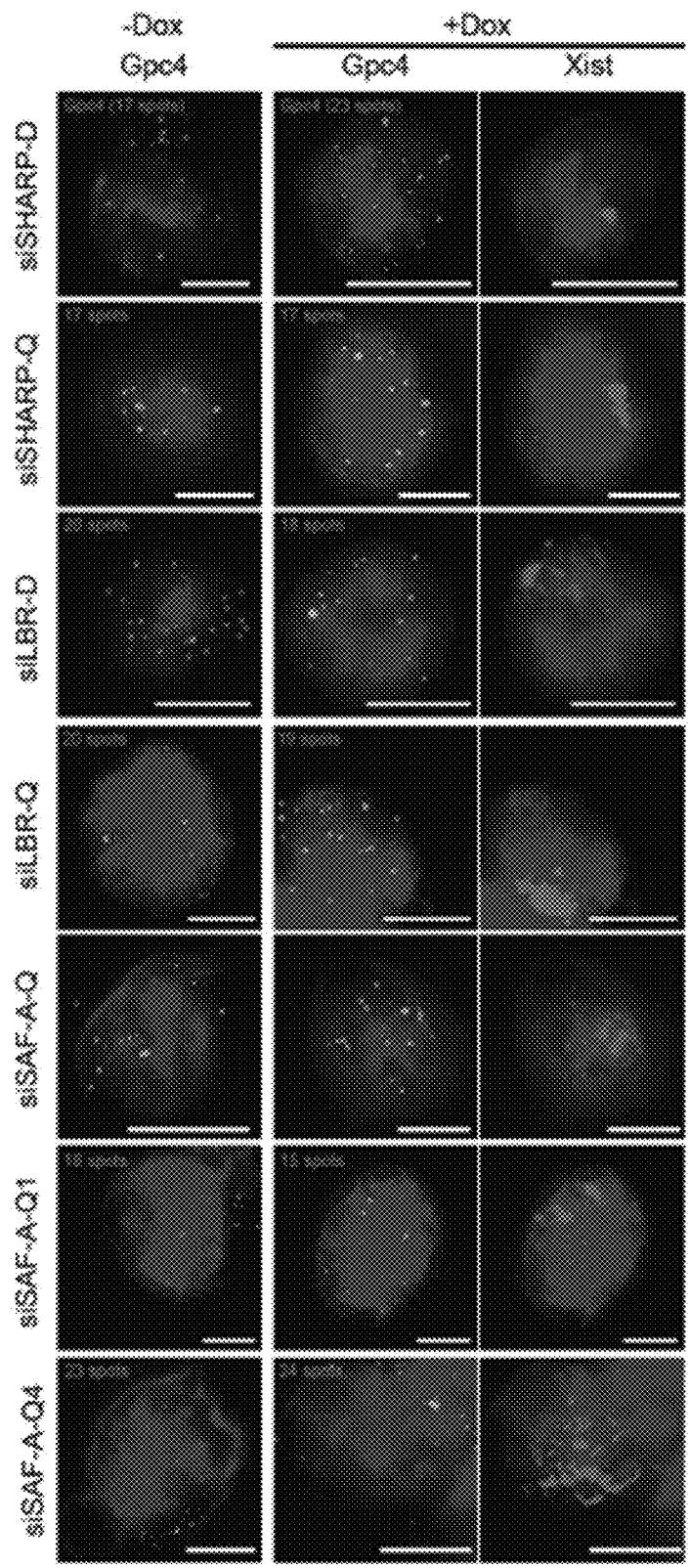
FIG. 6C shows representative images showing staining of DAPI (blue), Xist (red), and Gpc4 (green) after knockdown of proteins using independent, non-overlapping, siRNA pools, or individual siRNA deconvoluted from the pool prior to Xist induction (−Dox; left) or after Xist induction for 16 hours (+Dox; middle and right), for which cells were either transfected with the siRNA pool from Dharmacon (siRNA-D), Qiagen (siRNA-Q) or Ambion/Life Technologies (siRNA-A), or each individual siRNA deconvoluted from the pool from Dharmacon (siRNA-D1, 2, 3, 4) or Qiagen (siRNA-Q1, 2, 3, 4), according to methods described herein, according to embodiments of the present invention.
Figure 6C:
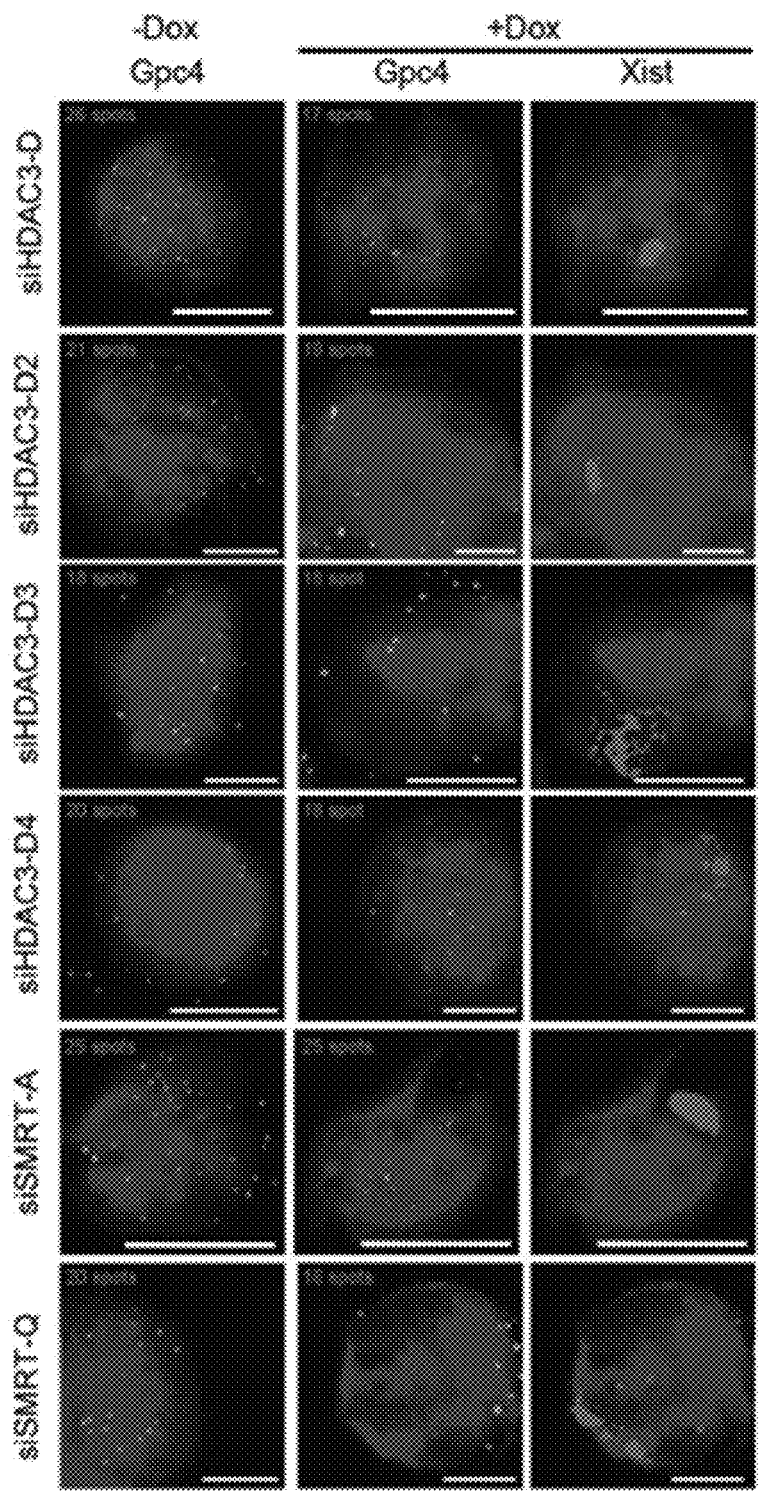
Figure 6D:
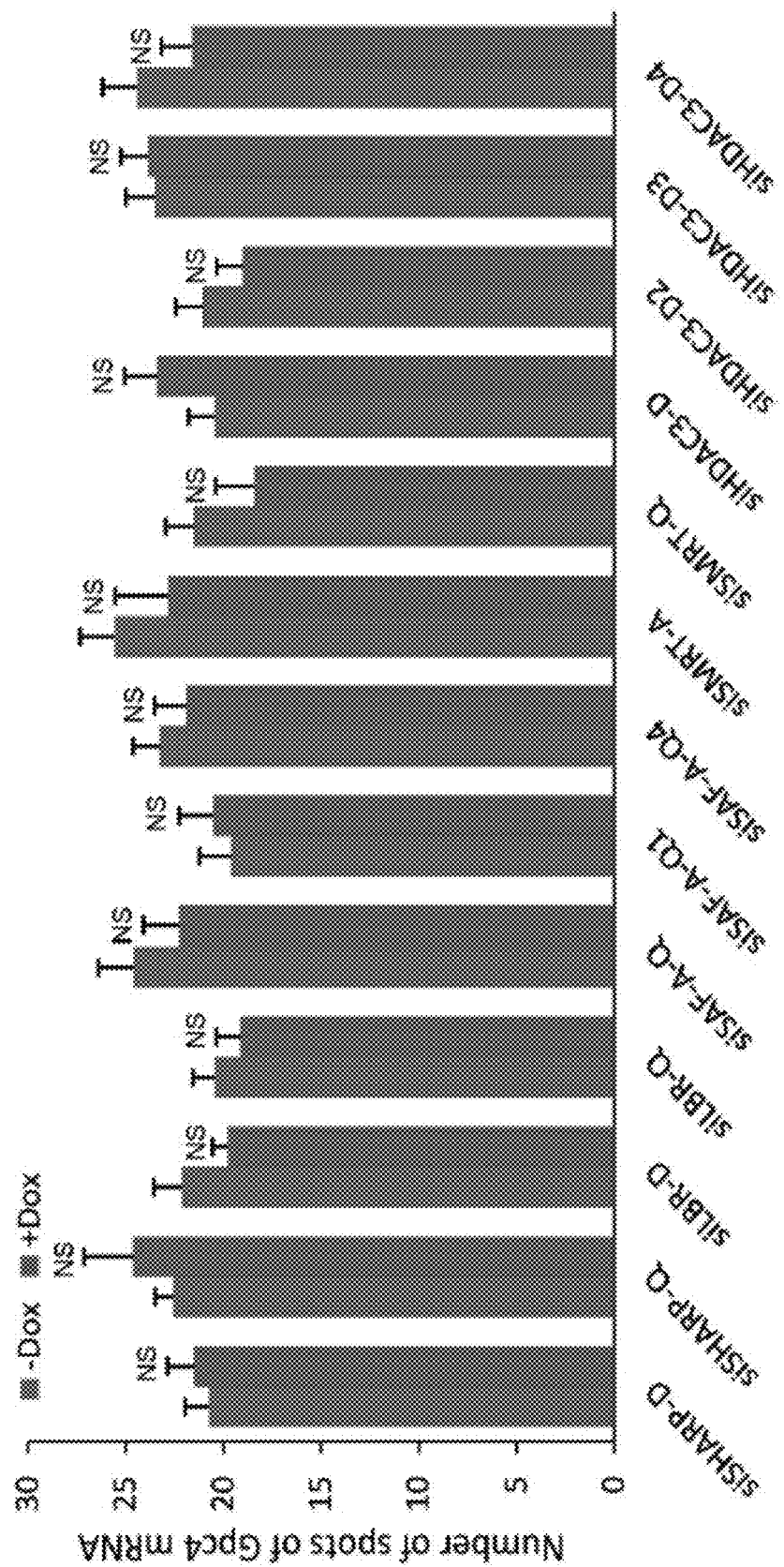
FIG. 6D is a graph of the quantification of the copy number of Gpc4 in −Dox and +Dox cells after knockdown with siRNAs targeting different mRNAs, with error bars represent the standard error of the mean across 50 individual cells from one experiment, with NS: not significantly different between +Dox and −Dox cells based on an unpaired two-sample t-test. Scale bars on the images represent 5 μm, according to embodiments of the present invention.

In some embodiments siRNA targeted to the mRNA of one of SHARP, SMRT, HDAC3, LBR, or SAF-A thereby prohibiting translation of the target protein. For example, siRNA targeted separately against each of SHARP, SMRT, HDAC3, LBR, and SAF-A in cells precludes Xist-dependent silencing. As shown in FIGS. 5A-5B, Gpc4 transcription proceeded with Xist induction when one of LBR, SHARP, SAF-A, SMRT, or HDAC3 expression was inhibited by siRNA. By comparison, siRNA targeted against other Xist silencing components—including components that directly bind Xist (e.g., PTBP1) did not inhibit Xist silencing as these components are not essential for Xist-dependent silencing. In another example, the amount of Gpc4 mRNA was quantified in cells undergoing Xist induction (+dox, orange bars) with siRNA knock down of the indicated proteins as shown in FIGS. 6A-6B, in which siRNA knockdown of any of LBR, SHARP, SAF-A, SMRT, or HDAC3 resulted in transcription (amount of Gpc4 mRNA) at levels comparable to the transcription in the absence of Xist (−dox, blue bars). Various siRNAs for each of SHARP, LBR, SAF-A, SMRT, and HDAC3 were assayed as shown in FIGS. 6C-6D, showing comparable effectiveness. Design of siRNAs with high functionality and specificity is described, for example, in Birmingham et al., 2007, *Nature Protocols*, 2:2068-2078, the entire content of which is herein incorporated by reference.

Embodiments of the present invention include molecules that directly contact the protein component and prohibit or disrupt binding of the protein component to lncRNA or another protein component, wherein the molecules that directly contact the protein component and prohibit or disrupt binding to lncRNA or another protein component are selected from the group consisting of antibodies, nanobodies, protein binding nucleic acid (DNA and RNA) aptamers, peptides, and small molecule inhibitors.

Considering the identified binding interactions of the Xist silencing complex proteins (SHARP, SMRT, HDAC3, SAF-A and LBR), embodiments of the present invention for prohibiting Xist-dependent gene silencing include targeting of these specific amino acid residues which may be carried out using several available methods including antibodies, nanobodies, DNA or RNA aptamers, peptides, and small molecule inhibitors. Methods for designing nanobodies are described in Steeland et al., 2016, *Drug Discov. Today*, doi:10.1016/j.drudis.2016.04.003 and Oliveira et al., 2013, *J. Control. Release*, 172:607-617, the entire contents of both of which are herein incorporated by reference. Methods for designing nucleic acid aptamers are described in Hermann and Patel, 2000, *Science*, 287:820-825, and Patel and Suri, 2000, *Rev. Molec. Biotechnol.*, 74:39-60, the entire contents of both of which are herein incorporated by reference.

In some embodiments of the present invention, prohibiting Xist-dependent gene silencing includes targeting of the SHARP protein with antibodies, nanobodies, aptamers, peptides, or small molecule inhibitors that target the binding sites for Xist on SHARP or the binding site for SMRT on SHARP. Xist binding sites on SHARP include four RNA recognition motifs (RRMs) (RRM1, RRM2, RRM3, and RRM4), where RRM1 includes amino acid (aa) residues 6-81, RRM2 includes aa residues 337-410, RRM3 includes aa residues 440-515, and RRM4 includes aa residues 519-591. The SMRT binding site on SHARP includes aa residues 3496-3664 which is referred to as the SPOC (Spen paralog and ortholog C-terminal) domain. Site directed mutagenesis studies have been reported for the SPOC residues with respect to binding to SMRT and transcription silencing activity. For example, SPOC domain residues K3516, K3606, R3548, and L3515 are vulnerable residues that upon manipulation decrease binding to SMRT. Additionally, phosphorylation is also required for the binding of SMRT and the SPOC domain of SHARP. (See, Mikami et al., 2014, *Structure*, 22: 35-46, the entire content of which is herein incorporated by reference.)

In some embodiments of the present invention, prohibiting Xist-dependent gene silencing includes prohibiting activity of the SMRT protein in the Xist silencing complex with antibodies, nanobodies, aptamers, peptides, or small molecule inhibitors that disrupt the interaction of SMRT with SHARP or SMRT with HDAC3. In some embodiments, targeting of the SMRT protein includes targeting the binding sites for SHARP or the binding site for HDAC3. The SHARP binding site on SMRT includes amino acids 2518-2525. The binding of residues 2518-2525 of SMRT to the SPOC domain of SHARP is dependent upon phosphorylation as described in Mikami et al., 2014, supra. The HDAC3 binding site on SMRT is referred to as the deactylase activating domain (DAD) at aa residues 395-489. In some embodiments, SMRT protein is targeted by the small molecule inhibitor arsenic trioxide.

In some embodiments of the present invention, prohibiting Xist-dependent gene silencing includes targeting the HDAC3 protein with antibodies, nanobodies, aptamers, peptides, or small molecule inhibitors that disrupt or prohibit the binding of HDAC3 with SMRT or abolish the deacetylase activity of HDAC3 and thereby prevent HDAC3 from acting to deacetylate chromatin and silence transcription. Of the 428 amino acid residues in HDAC3, the activity of HDAC3 is reported to be encompassed within residues 1-379. Residues His17, Lys25, Arg265, and Arg301 create a positively charged pocket. HDAC3 binding and conformational analysis is described in Abdelkarim et al., 2013, *ACS Chem Biol.*, doi:10.1021/cb400601g, the entire content of which is herein incorporated by reference. HDAC3 may be inhibited with a pan-HDAC inhibitor that targets both Class I and Class II HDAC proteins. However, as shown in FIGS. 6A-6B, inhibition of HDAC1 or HDAC2 does not prohibit Xist gene silencing. Accordingly, in some embodiments of the present invention, prohibition of Xist dependent gene silencing includes inhibiting with a Class I HDAC inhibitor or a HDAC3-specific inhibitor.

Figure 7A:
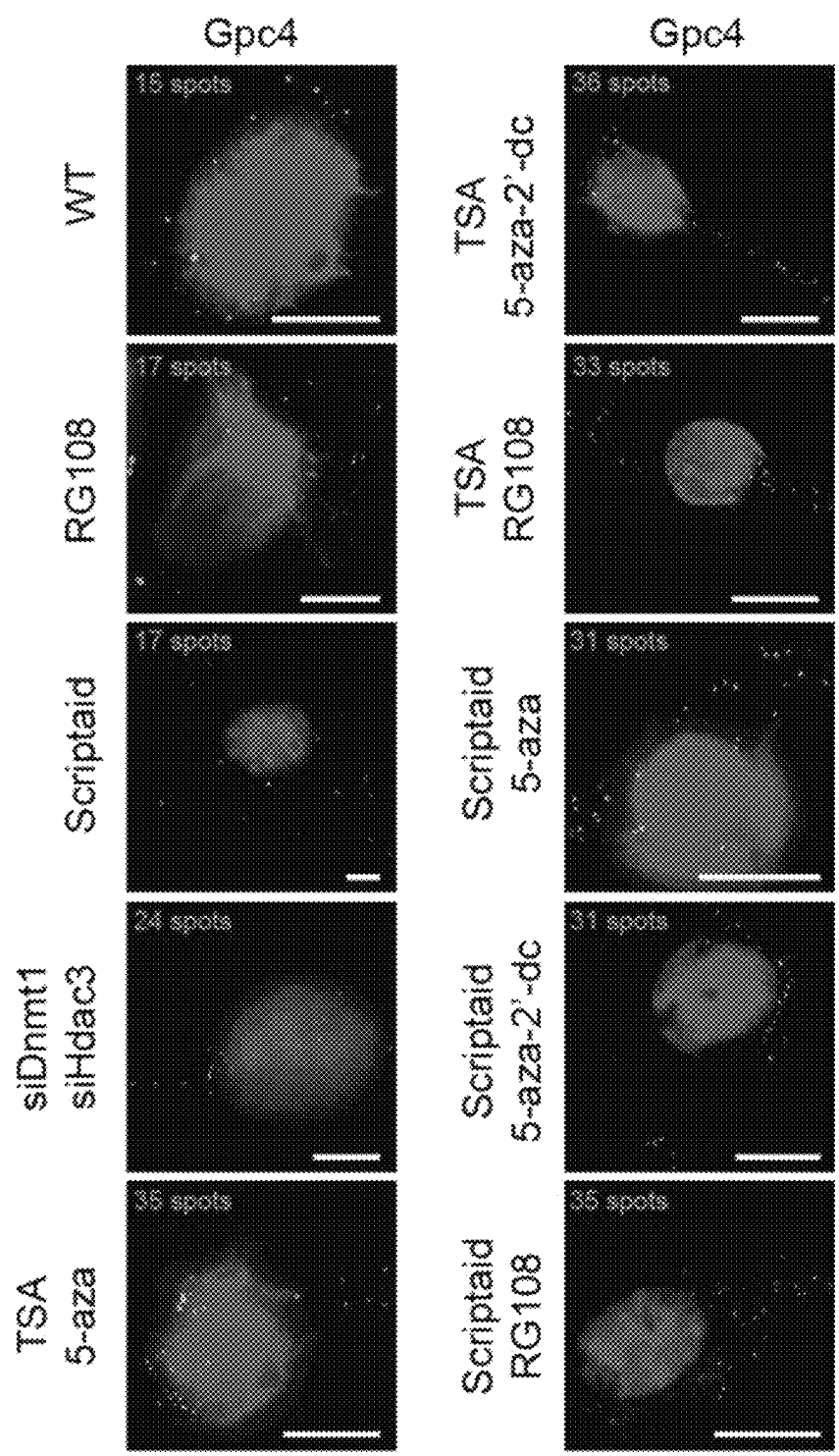
FIG. 7A shows images of individual cell for Gpc4 mRNAs (green) along with DAPI (blue) in cells with knock down of DNMT1 and HDAC3 or treating with DNMT1 and HDAC3 inhibitors, according to embodiments of the present invention.
Figure 7B:
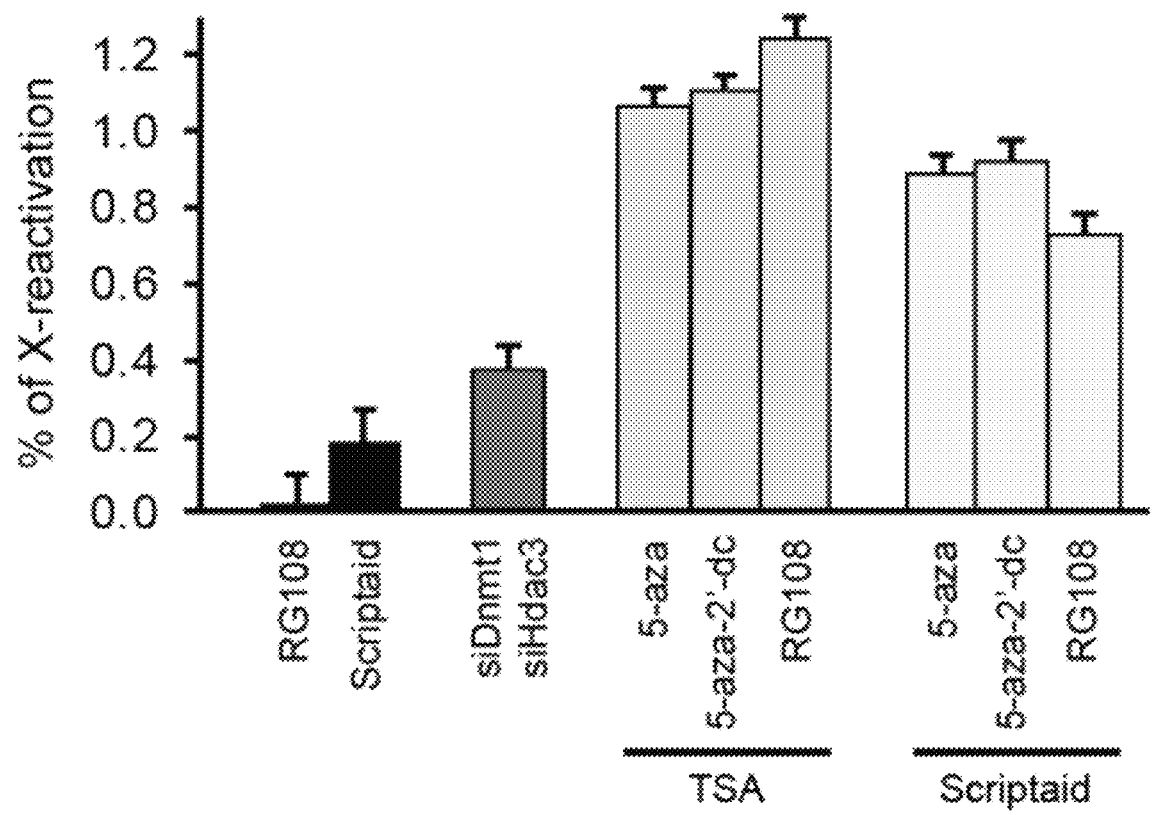
FIG. 7B is a graph of the quantification of the copy number of Gpc4 mRNA among different conditions, with error bars representing the standard error across 50 individual cells, scale bars: 5 micrometers, according to embodiments of the present invention.

Non-limiting examples of small molecule inhibitors of HDAC3 include Trichostatin A (TSA), Scriptaid, SAHA, RGFP 966, CUDC-907, Quisinostat, RG2833, PCI-24781, CUDC-101, Pracinostat, Resminostat, Rocilinostat, 4SC-202, Mocetinostat, HPOB, Entinostat, Droxinostat, and butryic acid. As shown in FIGS. 7A-7B, mouse MLF cells having silenced X genes were incubated with the HDAC3 inhibitor Scriptaid resulting in expression of Gpc4 as measured by levels of Gpc4 mRNA.

Reactivation of Xist-Mediated Silenced Genes

In some embodiments of the present invention, a method of reactivating expression of at least one Xist-dependent silenced X chromosome gene or a silenced Xist-dependent autosome gene includes prohibiting any one of the direct interactions in the Xist silencing complex thereby inhibiting Xist-mediated gene silencing. As shown in FIGS. 7A-7B, MLF cells having silenced X genes were incubated with the HDAC3 inhibitor Scriptaid (black bar) resulting in the reactivation of the Xist-dependent silent Gpc4 gene as measured by the levels of Gpc4 mRNA.

Figure 7C:
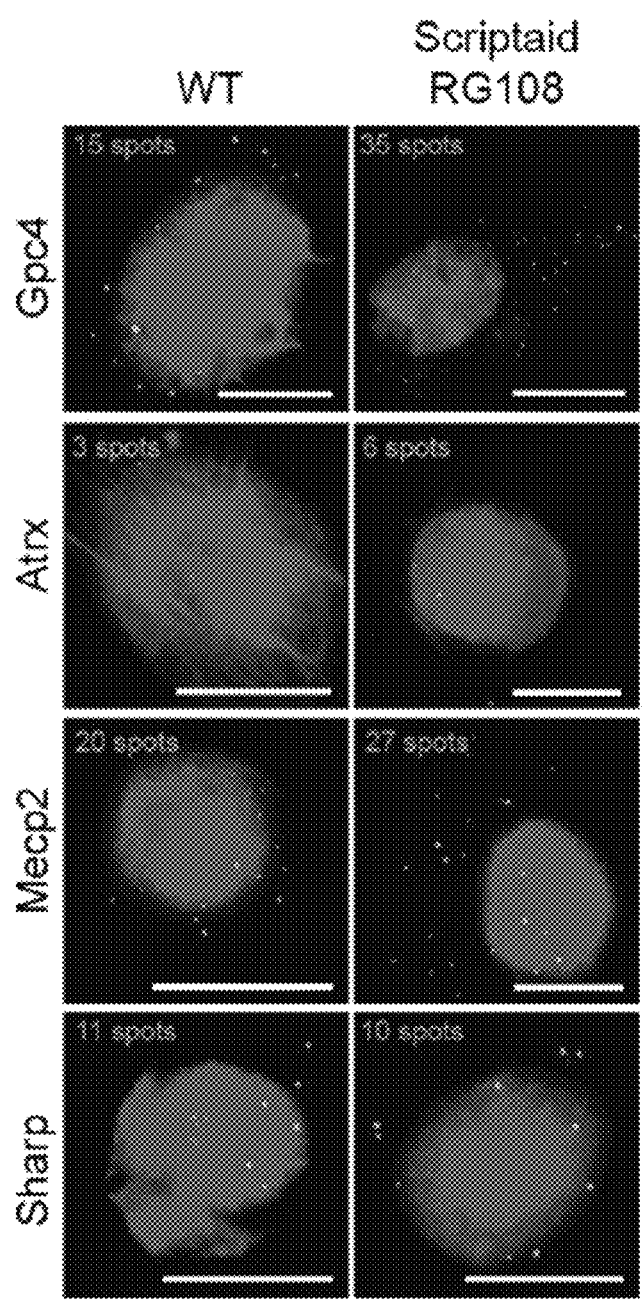
FIG. 7C shows images of individual cell for Gpc4, Atrx, Mecp2 or Sharp mRNAs (green) along with DAPI (blue) in cells treated with DMSO (WT) or DMNT1 and HDAC3 inhibitors, according to embodiments of the present invention.
Figure 7D:
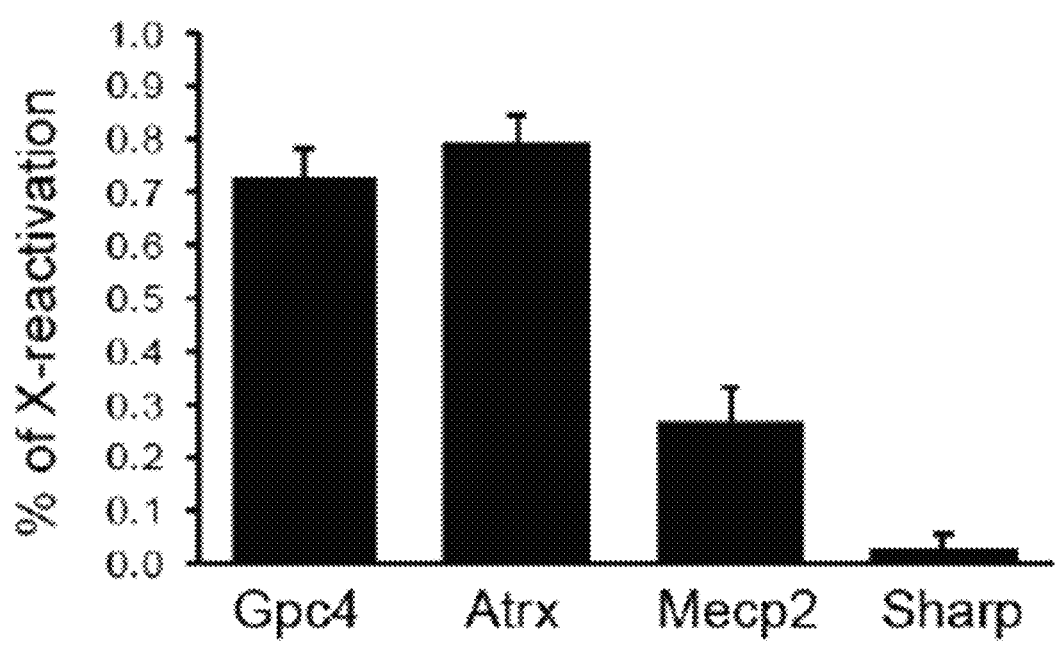
FIG. 7D is a graph of the quantification of the copy number of Gpc4, Atrx, Mecp2 or Sharp mRNA among different conditions, with error bars representing the standard error across 50 individual cells, scale bars: 5 micrometers, according to embodiments of the present invention.

In some embodiments of the present invention, reactivation of Xist-dependent silenced genes includes the prohibition of any one of the direct interactions in the Xist silencing complex in combination with inhibition of DNA methylation. For example, MLF cells were administered either the HDAC3 inhibitor Scriptaid or Trichostatin A (TSA) in combination with one of the DNA (cytosine-5-)methyltransferase 1 (DNMT1) inhibitors 5-Azacytidin (5-aza), 5-aza-2'deoxycytidine (5-aza-2'-dc), RG108, or SGI-1027. As shown in FIGS. 7A-7B the silenced X-chromosome gene Gpc4 was reactivated to a higher level of reactivation (i.e. having high levels of Gpc4 mRNA) than with Scriptaid alone. As shown in FIGS. 7C-7D, the X chromosome genes Gpc4, Atrx, and Mecp2 were reactivated in MLF cells administered with HDAC3 inhibitor and DNMT1 inhibitor, however, the SHARP autosomal gene remained unaffected.

The following Examples are presented for illustrative purposes only, and do not limit the scope or content of the present application.

EXAMPLES

Reference is made to the references cited in McHugh et al., 2015, *Nature*, 521:232-236, the entire contents of which are incorporated herein by reference.

Example 1

RNA Antisense Purification (RAP) Method to Purify Xist Complex

Figure 8:
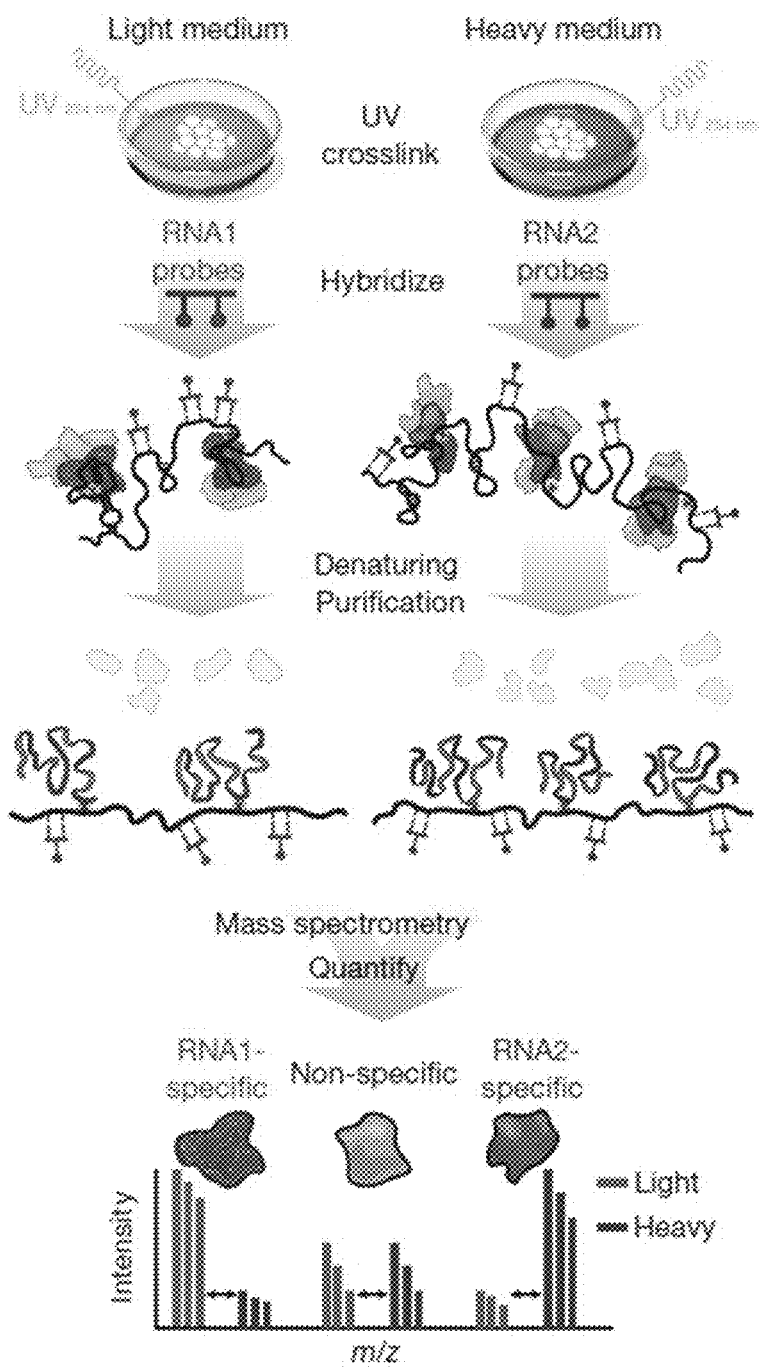
FIG. 8 is a schematic overview of the RAP-MS method, according to embodiments of the present invention.

To develop a method for identifying the proteins that directly interact with a specific lncRNA in vivo, the RNA Antisense Purification (RAP) method as described in Engreitz et al., 2013, *Science*, doi: 10.1126/science. 1237973, the entire content of which is herein incorporated by reference, was modified to purify a lncRNA complex and identify the interacting proteins by quantitative mass spectrometry (RAP-MS) (FIG. 8). Briefly, RAP-MS uses UV crosslinking to create covalent linkages between directly interacting RNA and protein and purifies lncRNAs in denaturing conditions to disrupt non-covalent interactions. This UV-crosslinking and denaturing approach, which is utilized by methods such as CLIP, is known to identify only direct RNA-protein interactions and to separate interactions that are crosslinked in the cell from those that merely associate in solution.

Adapting this UV-crosslinking and denaturing approach to enable purification of a specific lncRNA is challenging for several reasons: (i) In order to purify lncRNA complexes in denaturing conditions, an RNA capture method was needed that can withstand harsh denaturing conditions. (ii) In order to detect the proteins associated with a given lncRNA, high purification yields was needed of a lncRNA complex because, unlike nucleic acids, proteins cannot be amplified prior to detection. (iii) Because any individual RNA is likely to be present at a very low percentage of the total cellular RNA, high levels of enrichment are needed to identify specific interacting proteins. (iv) Because the number of background proteins will be high, even after enrichment, accurate and sensitive methods are necessary for protein quantification to detect specific lncRNA interacting proteins.

Figure 9A:
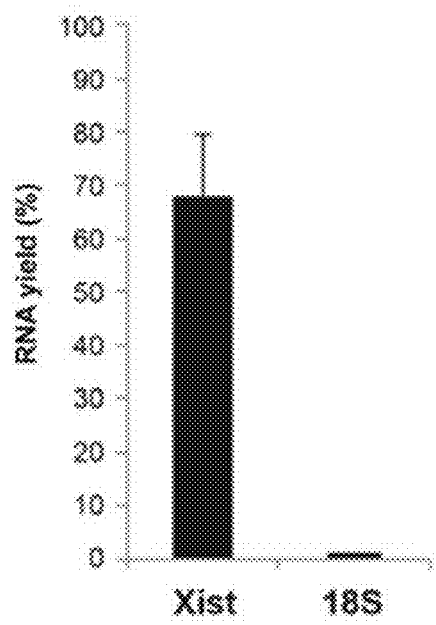
FIG. 9A is graph of the results of RT-qPCR measuring the percentage of the total cellular Xist or 18S recovered after RAP-MS of Xist, for which values are computed as the amount of each RNA in the elution divided by the amount of RNA in the starting ("input") lysate material, with error bars representing the standard error of the mean from 5 biological replicates, according to embodiments of the present invention.

The RAP-MS method addresses these challenges because: (i) RAP uses long biotinylated antisense probes, which form very stable RNA-DNA hybrids, and therefore can be used to purify lncRNA complexes in denaturing and reducing conditions (i.e., 4M urea at 67° C., Methods). (ii) The RAP method was optimized to achieve high yields of endogenous RNA complexes. Engreitz et al., 2013, supra, achieved less than 2% yield of the endogenous RNA complex; however, by optimizing hybridization, washing, and elution conditions an approximate 70% yield was obtained (FIG. 9A). (iii) Using the optimized conditions, the enrichment levels were increased for the target lncRNA complex (by approximately 5,000-fold, FIG. 9B) relative to our already high levels of enrichment achieved previously (by approximately 100-fold). (iv) To achieve sensitive quantification and to distinguish between specific proteins and background proteins, Stable Isotope Labeling by Amino acids in Culture (SILAC) was used to label proteins (FIG. 9C), which enables quantitative comparisons of purified proteins by mass spectrometry.

Figure 10A:
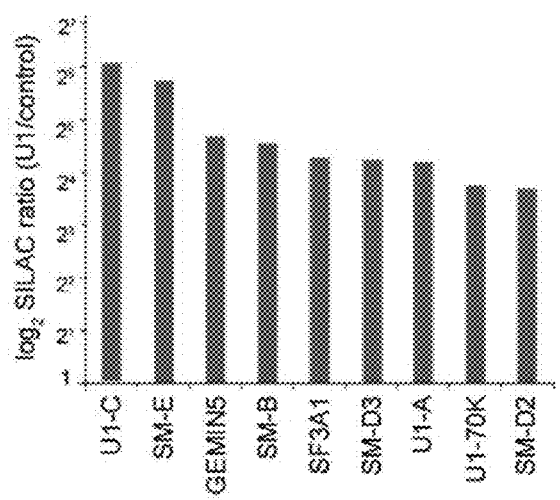
FIG. 10A is graph plotting SILAC ratios of top proteins enriched in the RAP-MS U1 snRNA, 18S rRNA, and 45S pre-rRNA experiments, according to embodiments of the present invention.
Figure 10A:
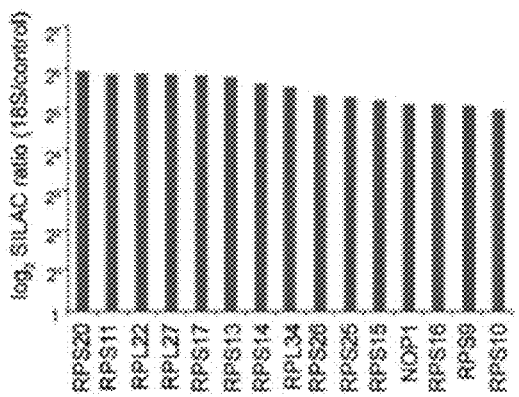
Figure 10A:
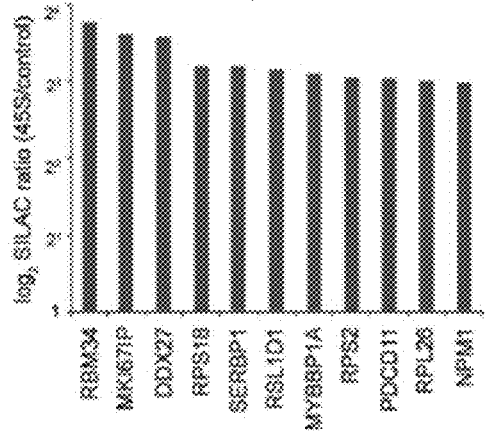
Figure 10B:
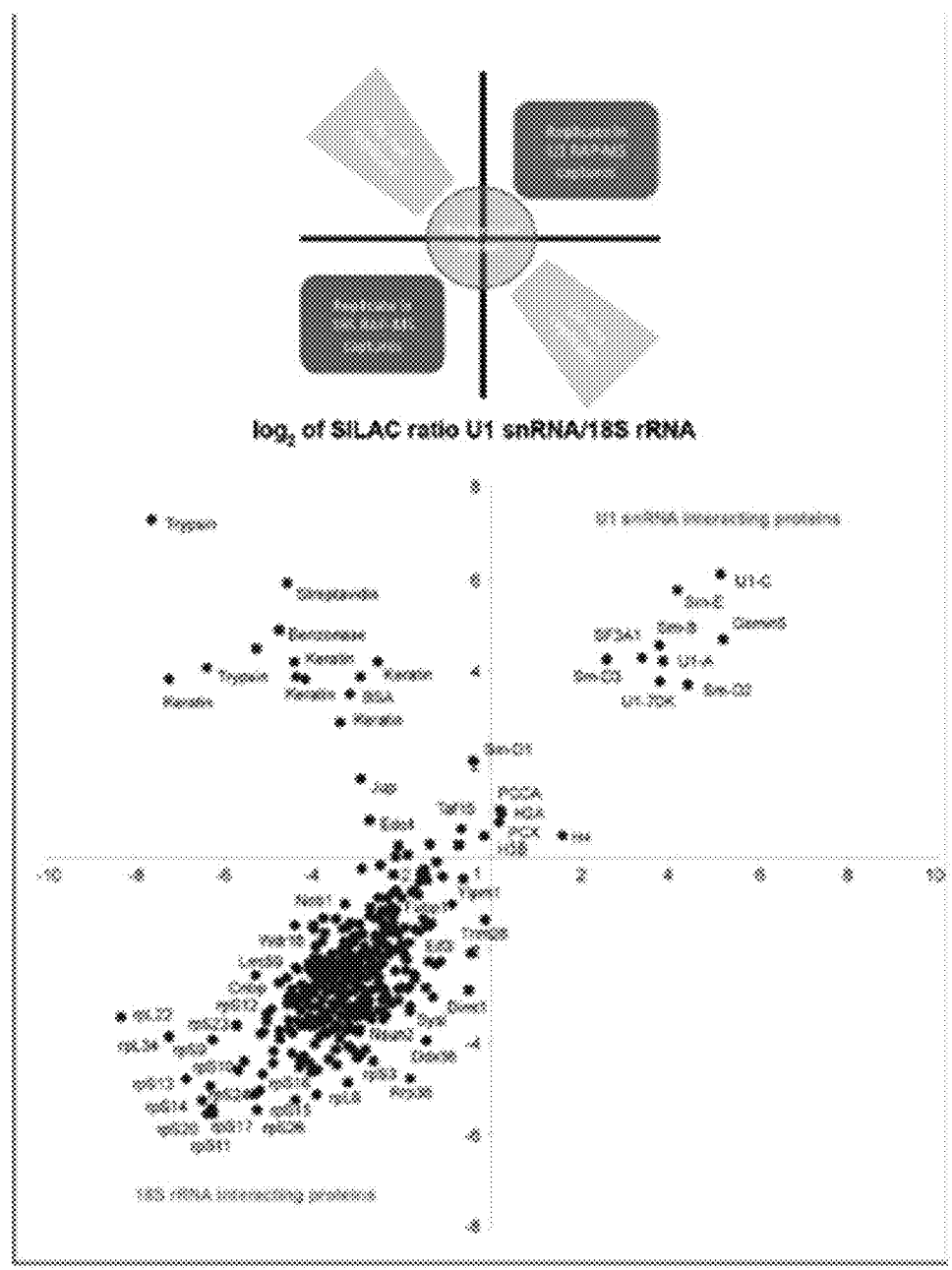
FIG. 10B is a SILAC ratio plot of replicate captures of U1 snRNA versus 18S rRNA from one of two biologically independent label-swap experiments, in which proteins associated with U1 are consistently found in U1 samples, both light and heavy labeled (top right quadrant), and proteins specifically associated with 18S are consistently identified in 18S, both light and heavy (lower left quadrant), in which background contaminant proteins have low enrichments (center of panel) or are consistently found in the light channel and do not replicate between experiments (i.e. keratin, streptavidin), according to embodiments of the present invention.
Figure 10C:
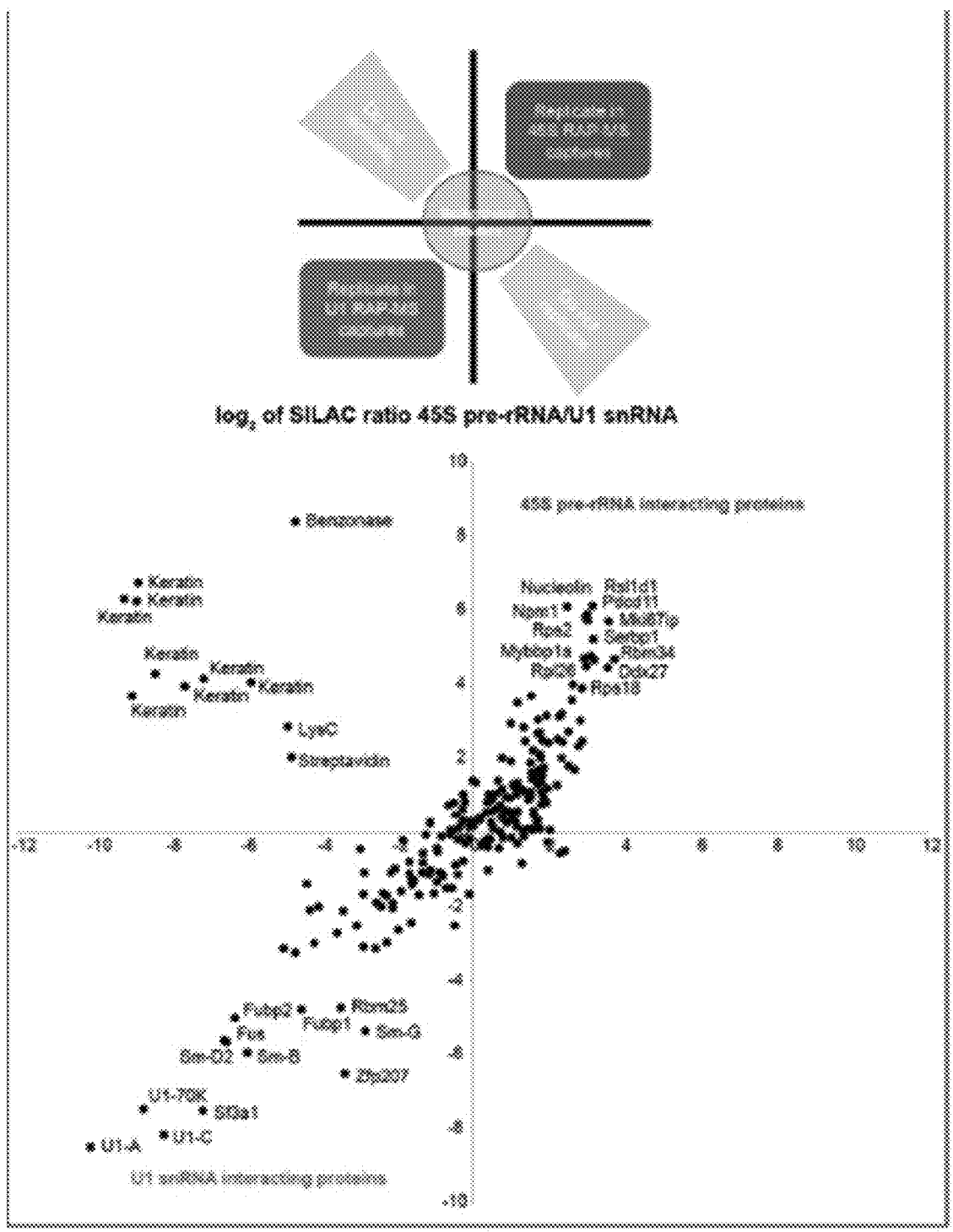
FIG. 10C is SILAC ratio plot of replicate captures of U1 snRNA versus 45S pre-rRNA from one label-swap experiment, for which proteins that are known to associate with 45S pre-rRNA are consistently identified in 45S captures, according to embodiments of the present invention.

The RAP-MS approach was validated by defining the proteins that interact with two well-characterized non-coding RNAs: U1 (a core component of the spliceosome) and 18S (a component of the small ribosomal subunit). In the U1 purifications, 9 enriched proteins were identified, all of which are known to interact with U1. In the 18S purification, 105 enriched proteins were identified, 98 of these (93%) were previously characterized as ribosomal proteins, ribosomal processing and assembly factors, translational regulators, or other known ribosome interactors (FIGS. 10A, 10B, 10C). In particular, 21 of the 31 known small ribosomal subunit proteins were identified. The few missing proteins appear to fall predominately into two categories: (i) proteins that make few direct contacts with the RNA and (ii) small proteins that contain few peptides that could be detected by mass spectrometry. These results demonstrate that the RAP-MS method identifies the majority of known RNA interacting proteins, and that the proteins identified by RAP-MS are highly specific for the purified ncRNA complex.

To define the proteins that interact with Xist during the initiation of XCI, the mouse embryonic stem (ES) cells were UV-crosslinked SILAC-labeled after Xist induction and purified Xist in nuclear extracts. To control for background proteins or non-specific proteins that might interact with any nuclear RNA, the abundant U1 snRNA was purified, which is not expected to interact with the same proteins as Xist. The proteins in each sample were identified using liquid chromatography-mass spectrometry and calculated a SILAC ratio for each protein based on the intensity of all heavy or light peptides originating from the Xist or U1 purification (FIG. 8).

Figure 11A:
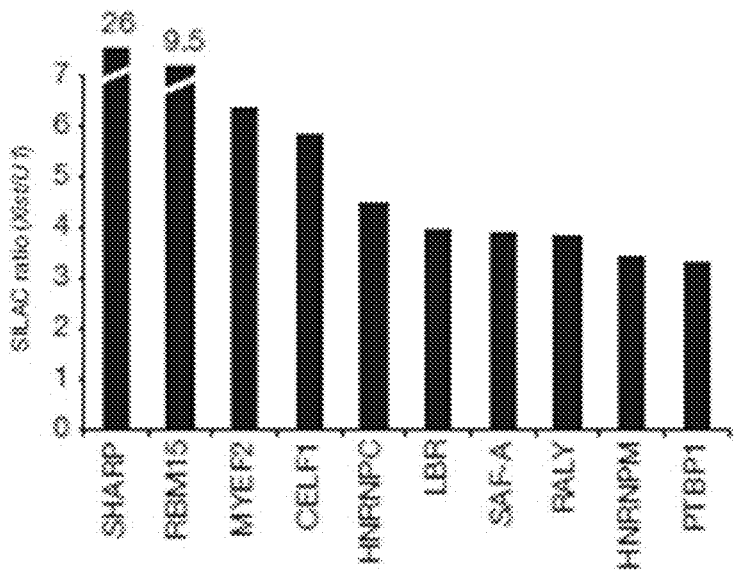
FIG. 11A is a graph plotting the SILAC ratio (Xist/U1) for each Xist-enriched protein identified by RAP-MS for one representative sample of four biological replicates, which for SHARP and RBM15, the enrichment values are indicated above their bars, according to embodiments of the present invention.
Figure 11B:
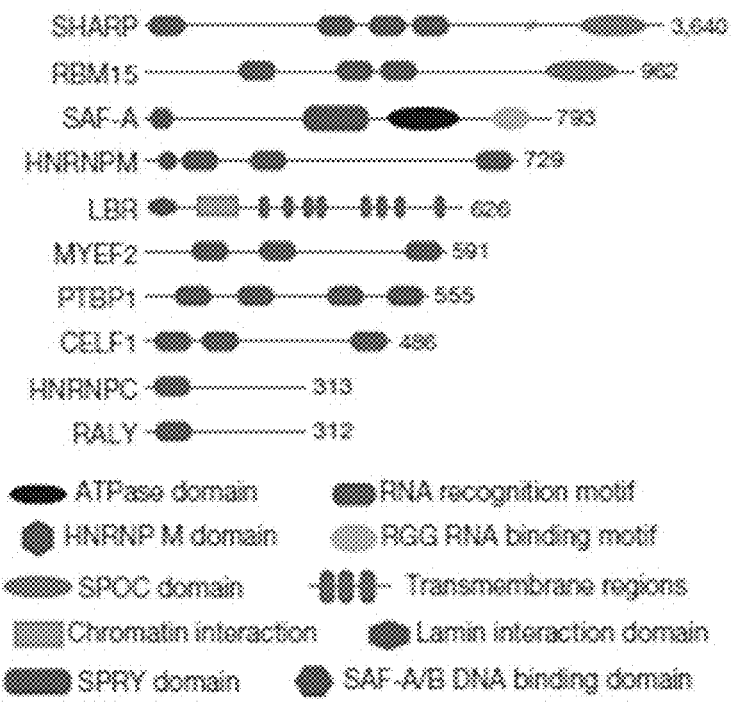
FIG. 11B is a schematic of each Xist-interacting protein is shown (scaled to protein length), with the locations of functional domains are shown, according to embodiments of the present invention.

Ten proteins were identified that were enriched for Xist relative to U1 (SILAC ratio >3-fold, FIG. 11A). All 10 proteins were reproducibly enriched in multiple Xist purifications from independent biological samples. Consistent with the notion that these proteins are direct Xist-interacting proteins, 9 proteins contain well-characterized RNA binding domains (FIG. 11B).

Example 2

Identification of Xist-Interacting Proteins

The identified Xist-interacting proteins are SHARP, Rbm15, Myef2, Celf1, hnRNPC, LBR, SAF-A, Raly, hnRNPM, and Ptbp1 (FIG. 11A). SAF-A (Scaffold Attachment Factor-A, also called hnRNPU) was previously shown to interact directly with Xist and is required for tethering Xist to the inactive X-chromosome in differentiated cells 10. In addition, 5 of these proteins have been previously implicated in transcriptional repression, chromatin regulation, and nuclear organization. These include SHARP (SMRT and HDAC Associated Repressor Protein, also called SPEN), a member of the SPEN family of transcriptional repressors, which directly interacts with the SMRT component (also called NCoR-2) of the nuclear co-repressor complex 16 that is known to interact with and activate HDAC3 deacetylation activity on chromatin7 (FIG. 11B). Interestingly, RBM15, another member of the SPEN family of transcriptional repressors, was also identified. RBM15 shares the same domain structure as SHARP, but appears to have a distinct functional role during development. Myef2 has been shown to function as a negative regulator of transcription in multiple cell types, although its mechanism of regulation is still unknown. hnRNPM is a paralog of Myef2. Finally, LBR (Lamin B receptor), a protein that is anchored in the inner nuclear membrane and interacts with repressive chromatin regulatory proteins and Lamin B19 (FIG. 11B) was also identified.

The specificity of the identified Xist-interacting proteins was confirmed as follows: (i) To ensure that they are not due to non-specific RNA or protein capture, RAP was performed in uninduced cells (no Xist) and identified no enriched proteins. (ii) To ensure that these proteins are crosslinked with Xist in cells and not merely associating in solution, RAP was performed in cells that were not crosslinked (no UV) and identified no enriched proteins. (iii) To ensure that these proteins do not merely interact with any nuclear-enriched long ncRNA, the Xist-purified proteins were compared to those purified with 45S (pre-ribosomal RNA) and found that all 10 Xist-interacting proteins were still enriched. (iv) To independently validate these interactions, high-quality affinity reagents were obtained for 8 of the 10 proteins (Ptbp1, hnRNPC, Celf1, Myef2, Rbm15, LBR, Raly, and SHARP) and immunoprecipitated the identified proteins in UV-crosslinked lysates. In all cases, a strong enrichment for the Xist RNA (>4-fold) was observed, but not control mRNAs or lncRNAs (FIGS. 12A, 12B, 12C, 12D and Table 1).

Together, these results identify a set of highly specific and reproducible proteins that directly interact with Xist during the initiation of XCI. Given the generality of the RAP-MS approach, it was expected that it will be broadly applicable for defining the proteins that directly interact with other lncRNAs.

TABLE 1

A list of all antibodies used for immunoprecipitation experiments.

| Protein | Epitope | Vendor | Catalog # |
| --- | --- | --- | --- |
| RALY | V5-tagged clone | Sigma | V8137 |
| LBR | V5-tagged clone | Sigma | V8137 |
| hnRNPC | V5-tagged clone | Sigma | V8137 |
| RBM15 | Endogenous | Santa Cruz | sc-366873 |
| PTBP1 | Endogenous | Abcam | ab5642 |
| CELF1 | Endogenous | Abcam | ab129115 |
| PUM1 | Endogenous | Santa Cruz | sc-135049 |
| MYEF2 | Endogenous | Santa Cruz | sc-102031 |
| hnRNPH | Endogenous | Bethyl | A300-511A |
| IgG | None | Cell Signaling | 2729S |
| SHARP | Endogenous | Novus | NBP1-82952 |

Example 3

Identification of the Required Xist Silencing Complex Components

To determine which proteins are required for Xist-mediated transcriptional silencing, each of the identified proteins was knocked down and assayed for the failure to silence gene expression on the X-chromosome upon induction of Xist expression (FIG. 2).

Specifically, two X-linked genes, Gpc4 and Atrx, were selected that are well expressed in the absence of Xist expression, but are normally silenced by 16 hours of Xist induction in our doxycycline-inducible system in male cells (FIG. 5B). siRNAs were used to knockdown the mRNA levels of each of the proteins identified by RAP-MS along with several negative controls (Table 2). To ensure that each cell examined showed both successful depletion of the siRNA-targeted mRNA (>70% reduction) as well as induction of Xist expression using single molecule RNA FISH (Methods). Within each of these cells, the mRNA level was quantified of each of the two X-linked genes prior to Xist induction (−dox) and after Xist induction (+dox).

Figure 13A:
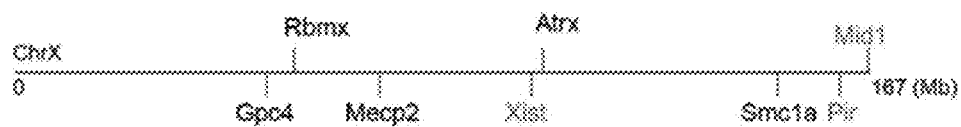
FIG. 13A is a diagram showing the locations of Xist (red), X-linked silenced genes (black), and X-linked escaped genes (green) along the X-chromosome, according to embodiments of the present invention.
Figure 13B:
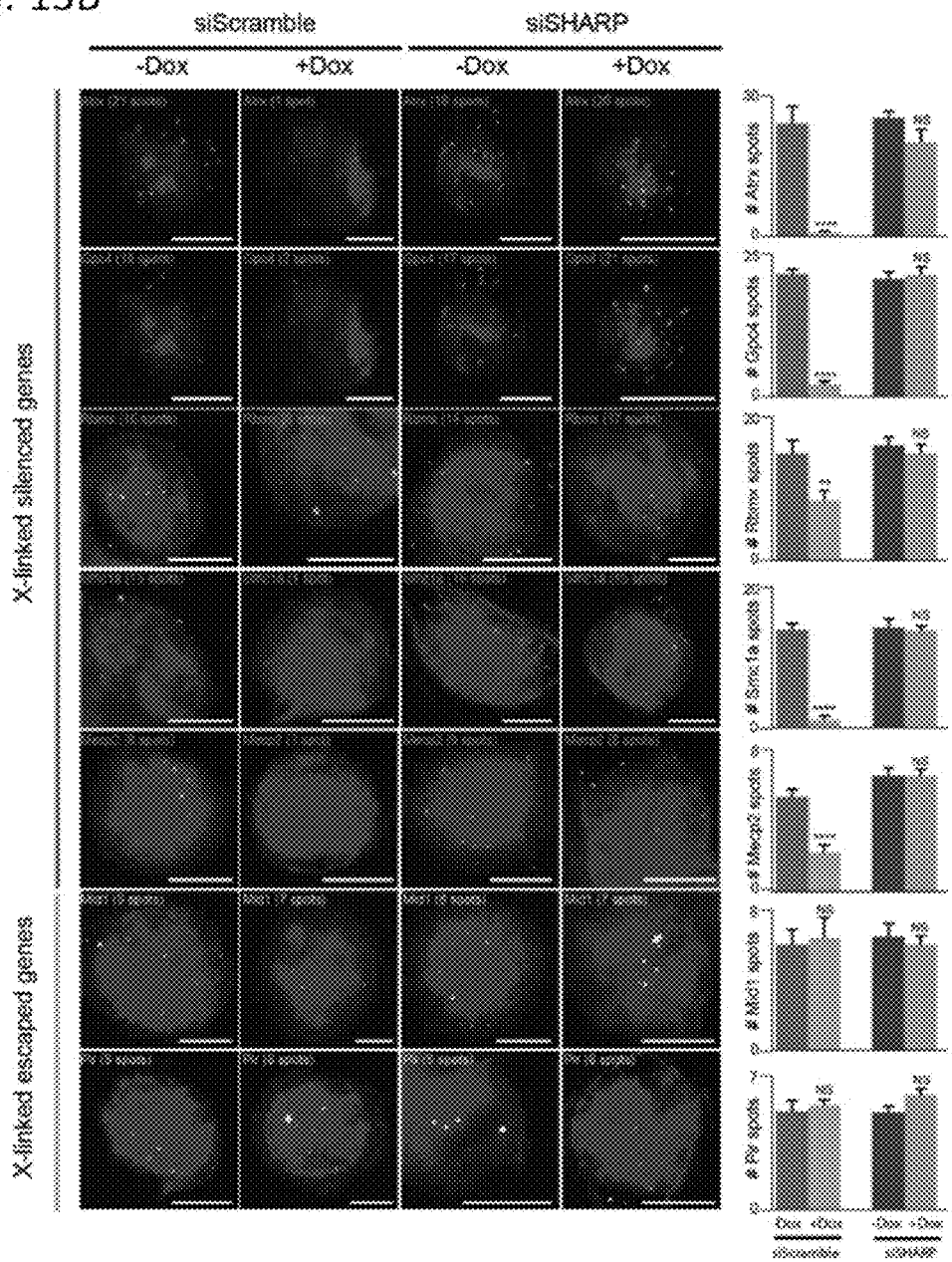
FIG. 13B shows representative images showing staining of DAPI (blue), Xist (red), X-linked silenced genes (green), and X-linked escaped genes (yellow) upon knockdown of SHARP or control male ES cells prior to Xist induction (−Dox) or after Xist induction for 16 hours (+Dox), in which knock of SHARP abolishes the silencing of Atrx, Gpc4, Rbmx, Smc1a and Mecp2, which are normally silenced upon Xist expression, but has no effect on Mid1 and Pir, which normally escape Xist-mediated silencing, according to embodiments of the present invention. The bar graphs show the quantification of the copy number of the mRNA for each gene for −Dox and +Dox cells upon transfection with SHARP siRNA or control siRNA; error bars represent the standard error of the mean across 50 individual cells from one experiment, NS: not significantly different, ** represents values with a p-value<0.001, and  represents values with a p-value<0.01 between +Dox and −Dox cells based on an unpaired two-sample t-test, with scale bars on the images represent 5 µm, according to embodiments of the present invention.
Figure 13C:
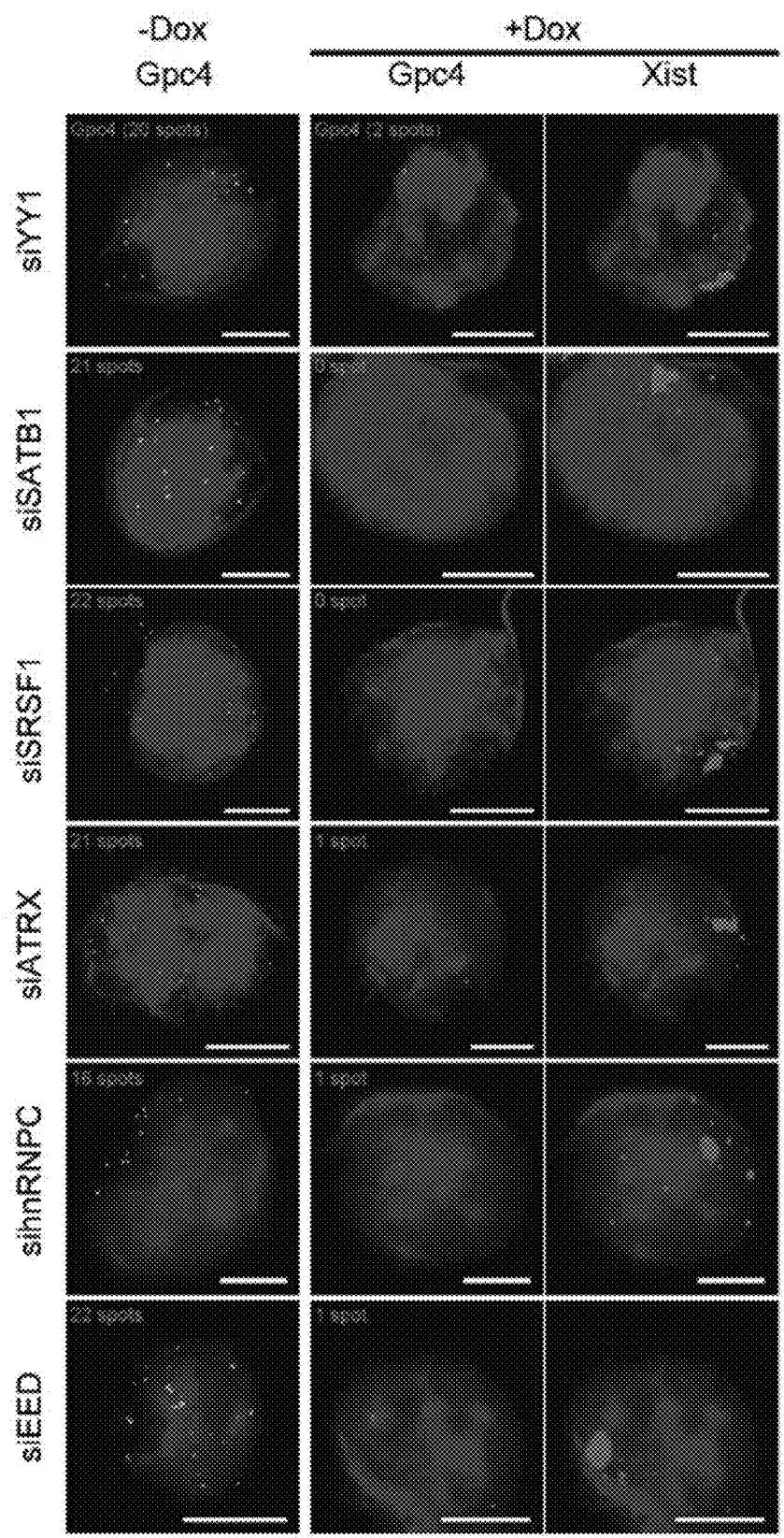
FIG. 13C shows representative images after knockdown of each protein—DAPI (blue), Xist (red), and Gpc4 (green) to test the function of several proteins that were previously identified to associate with Xist, but not to silence transcription, for their role in transcriptional silencing in our inducible male ES cells prior to Xist induction (−Dox; left) or after Xist induction for 16 hours (+Dox; middle and right), according to embodiments of the present invention.
Figure 13D:
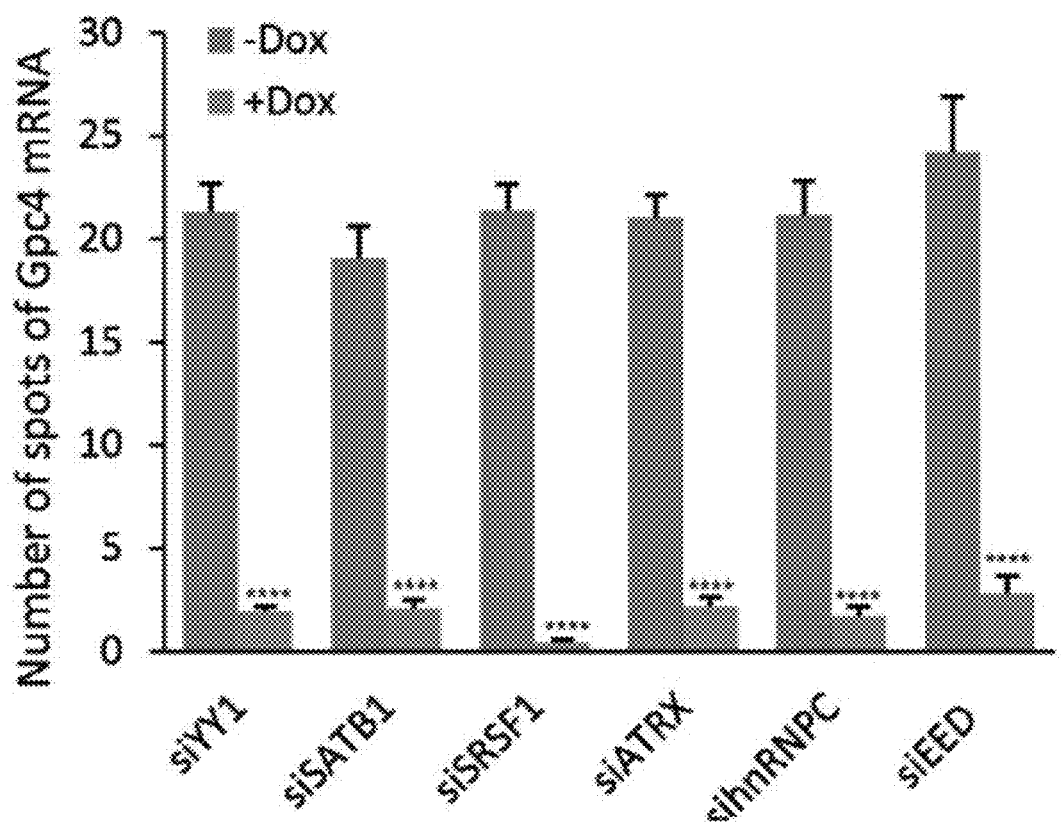
FIG. 13D is graph plotting the quantification of the copy number of Gpc4 before and after Xist induction upon treatment with different siRNAs, with error bars representing the standard error of the mean across 50 individual cells from one experiment, **** represents values with a p-value<0.001 between +Dox and −Dox cells based on an unpaired two-sample t-test, with scale bars on the images represent 5 µm, according to embodiments of the present invention.

As a control, several non-targeting siRNAs were transfected. In these negative controls, the expected silencing of the X-linked genes studied (Gpc4 expression decreased from an average of 20 copies (−dox) to 2 copies (+dox) per cell and Atrx expression decreased from 22 to 3 copies per cell; FIGS. 5A-5B) was observed. Consistent with previous observations, no effect was found on X-chromosome gene silencing upon knockdown of EED, a required component of PRC2 (FIG. 5A), or other proteins previously associated with Xist that do not appear to be required for transcriptional silencing (FIGS. 13C-13D). Similarly, knockdown of Rbm15, Myef2, Ptbp1, Celf1, hnRNPC, Raly, or hnRNPM did not alter gene silencing on the X-chromosome (FIG. 5A, FIGS. 6A-6B).

Figure 14A:
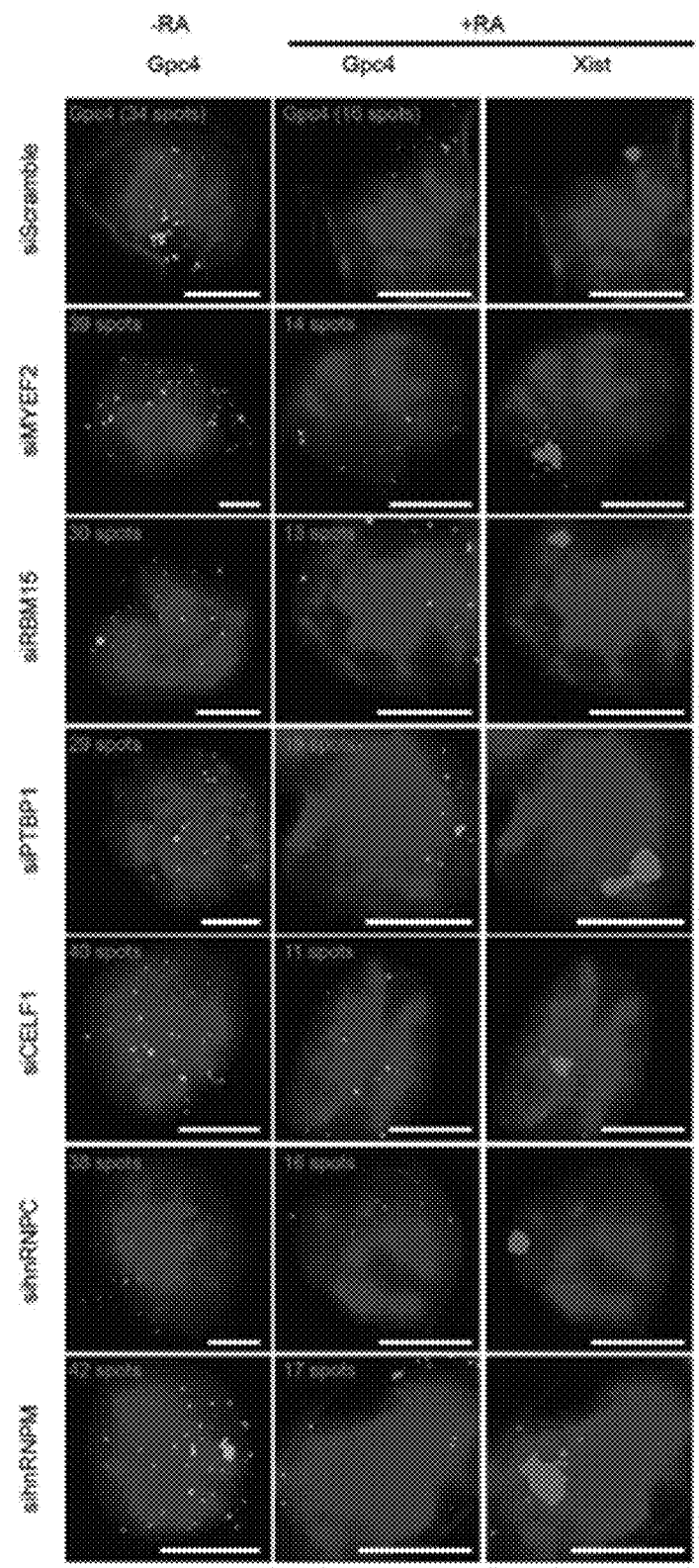
FIG. 14A shows representative images showing staining of DAPI (blue), Xist (red), and Gpc4 (green) upon knockdown of specific proteins using different siRNAs in female ES cells prior to differentiation (−RA; left) or after differentiation for 24 hours (+RA; middle and right), according to embodiments of the present invention.
Figure 14A:
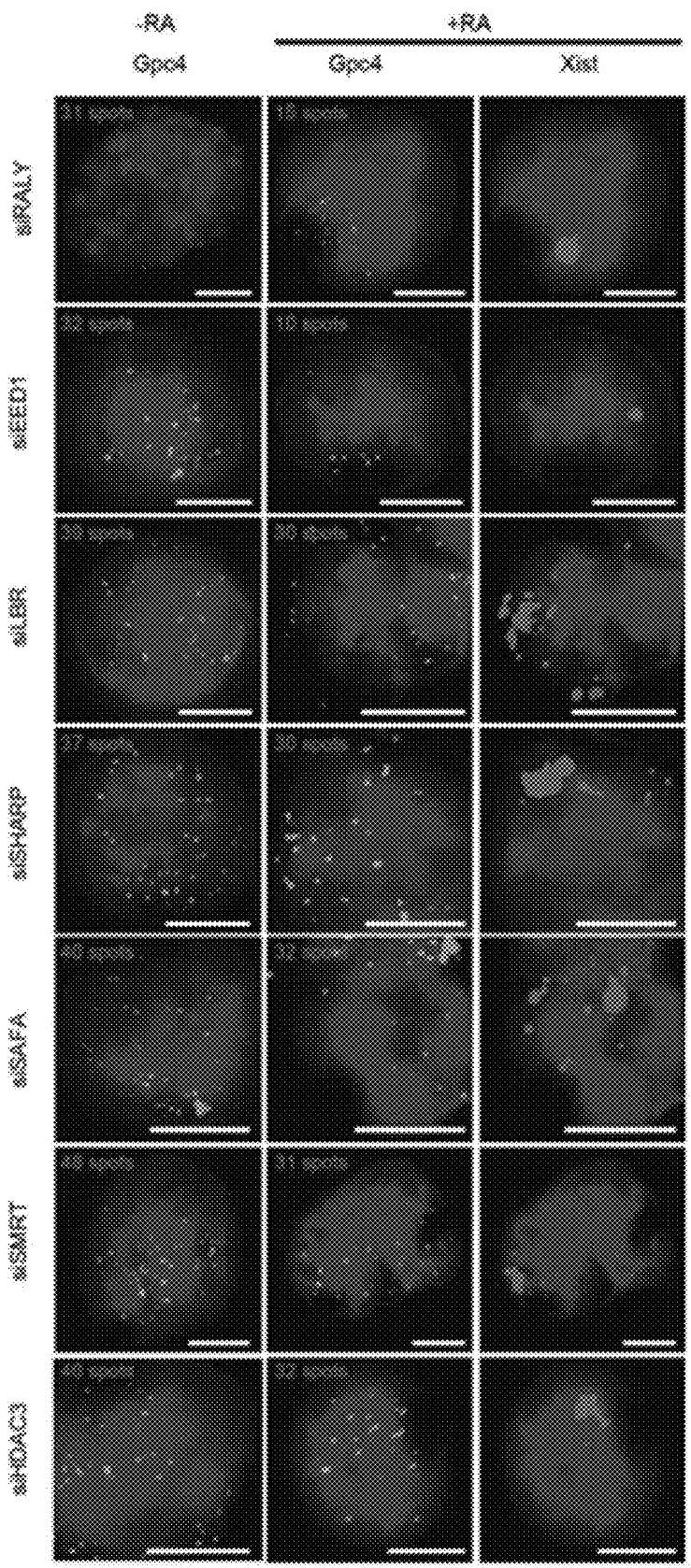
Figure 14B:
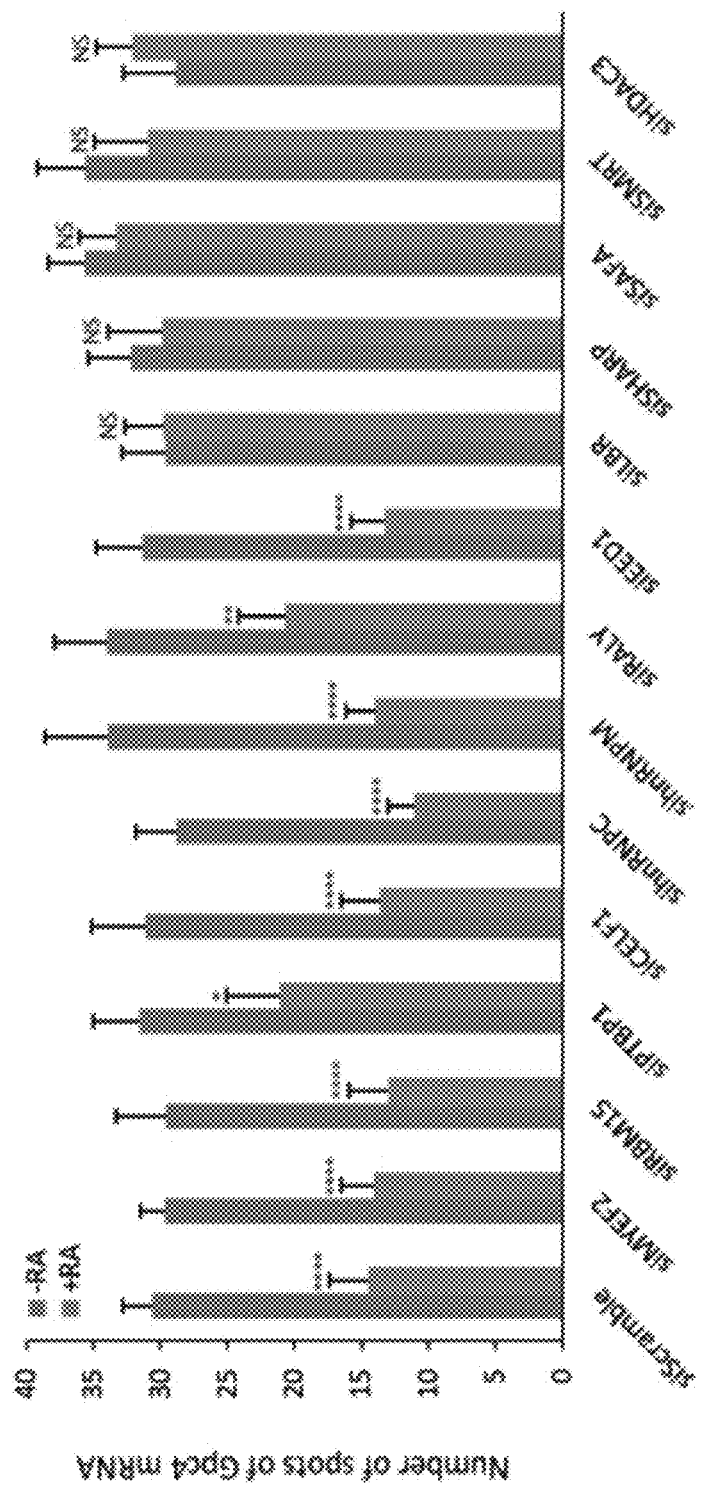
FIG. 14B shows quantification of the copy number of Gpc4 for −RA and +RA cells upon transfection with different siRNAs, with error bars representing the standard error across 50 individual cells from one experiment, NS: not significantly different between +RA and −RA cells; ** represents values with a p-value<0.001,  represents values with a p-value<0.01, and * represents values with a p-value<0.05 between +RA and −RA cells based on an unpaired two-sample t-test, with scale bars on the images represent 5 µm, according to embodiments of the present invention.

In contrast, knockdown of SHARP, LBR, or SAF-A largely abolished the silencing of X-chromosome genes following Xist induction (FIGS. 5A-5B, FIGS. 6A-6B, FIGS. 13A-13B). Indeed, the expression levels of the X-chromosome genes studied did not significantly change following Xist expression (FIG. 5B, FIGS. 6A-6B). These same silencing defects were observed with several independent siRNAs (FIGS. 6C-6D). Notably, the same X-chromosome silencing defects were observed upon knockdown of SHARP, LBR, or SAF-A in differentiating female ES cells (FIGS. 14A-14B).

These results demonstrate that SHARP, LBR, and SAF-A are required for Xist-mediated transcriptional silencing of the X-chromosome. Although the remaining seven Xist-interacting proteins showed no effect on X-chromosome gene silencing, they may still be important for Xist function: (i) some may have redundant functions (e.g. Myef2 and hnRNPM, which are known paralogs), (ii) in some of these cases, the small amount of protein remaining after knockdown may still be sufficient for Xist function, or (iii) some of these proteins may be important for alternative Xist-mediated roles, such as the maintenance of XCI, which would not be captured by this silencing assay.

Example 4

SAF-A Localization

Consistent with previous observations that SAF-A is required for Xist localization to chromatin in differentiated cells, a diffuse Xist localization pattern was observed in the nucleus upon knock down of SAF-A (FIG. 6A). This suggests that SAF-A is required for transcriptional silencing by localizing Xist, and its silencing proteins, to the X-chromosome during the initiation of XCI.

Example 5

Co-Localization of Xist and RNA Polymerase II

Figure 15A:
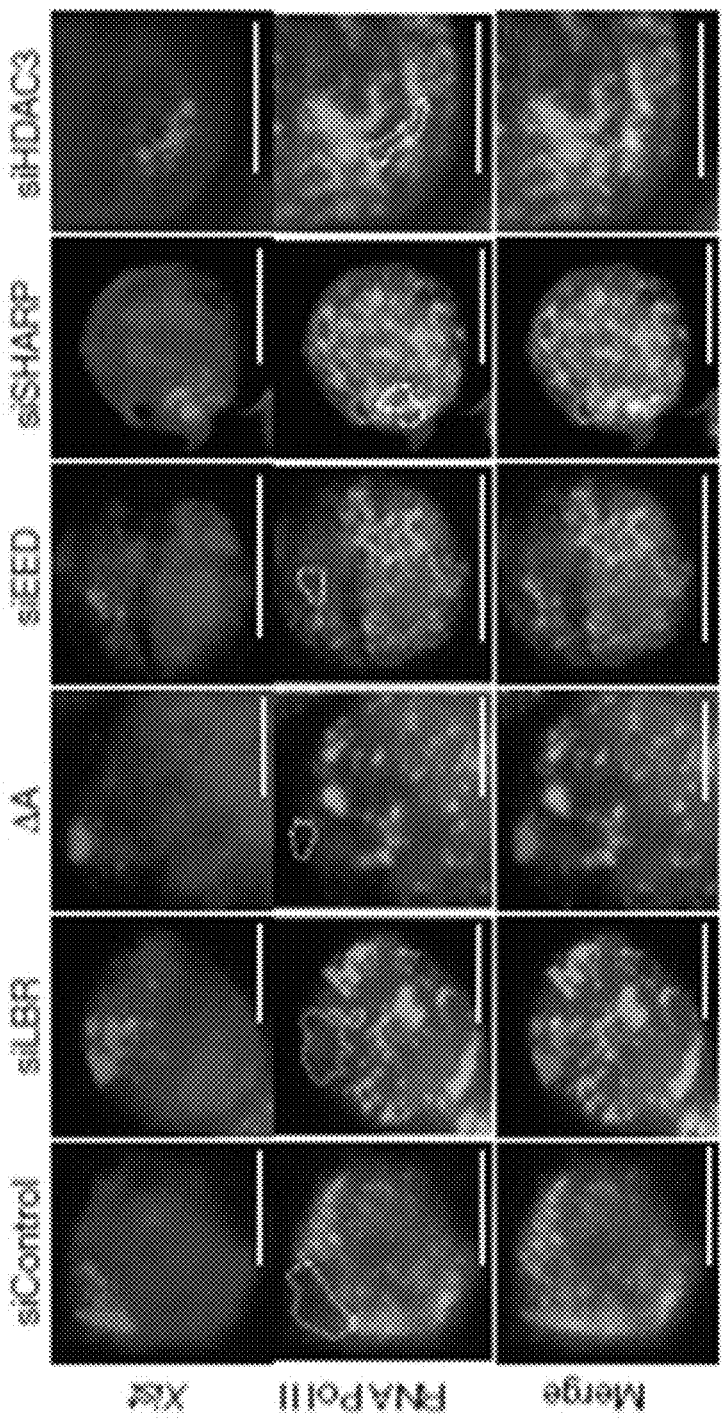
FIG. 15A shows representative fluorescent images of Xist (red), PolII (green), and DAPI (blue) across different siRNA conditions (rows), according to embodiments of the present invention.
Figure 15B:
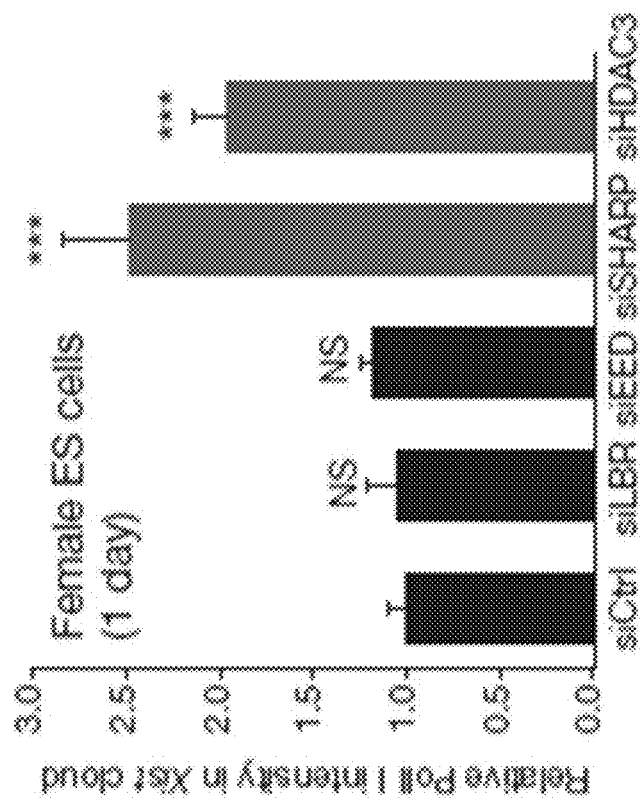
FIG. 15B is graph plotting quantification of fluorescence intensity of PolII within Xist territory as shown in FIG. 15A normalized to control siRNA levels, in male ES cells after 16 hours of doxycycline treatment, according to embodiments of the present invention.
Figure 15C:
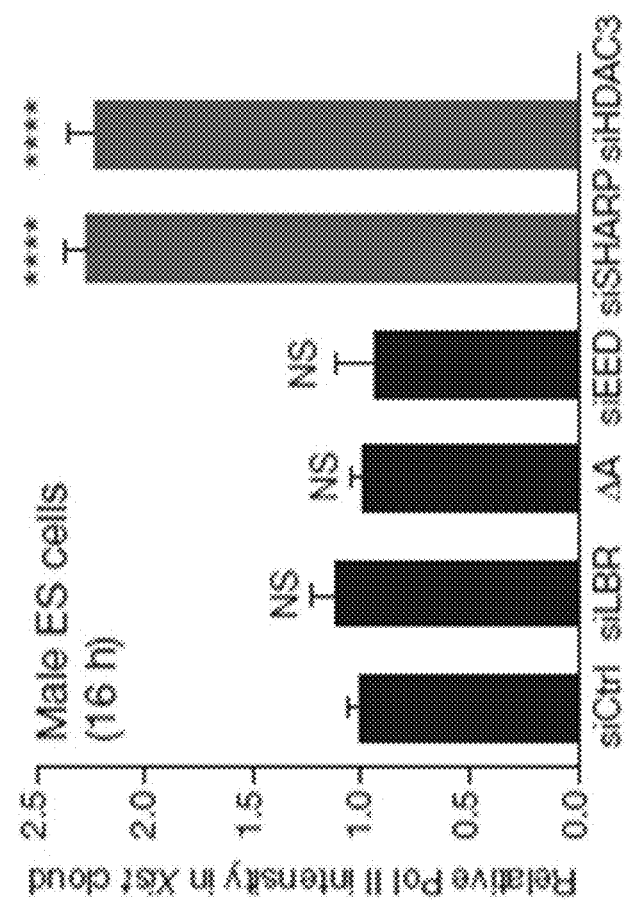
FIG. 15C is graph plotting quantification of fluorescence intensity of PolII within Xist territory as shown in FIG. 15A normalized to control siRNA levels, in female ES cells after 1 day of retinoic acid (RA) induced differentiation, according to embodiments of the present invention.
Figure 16:
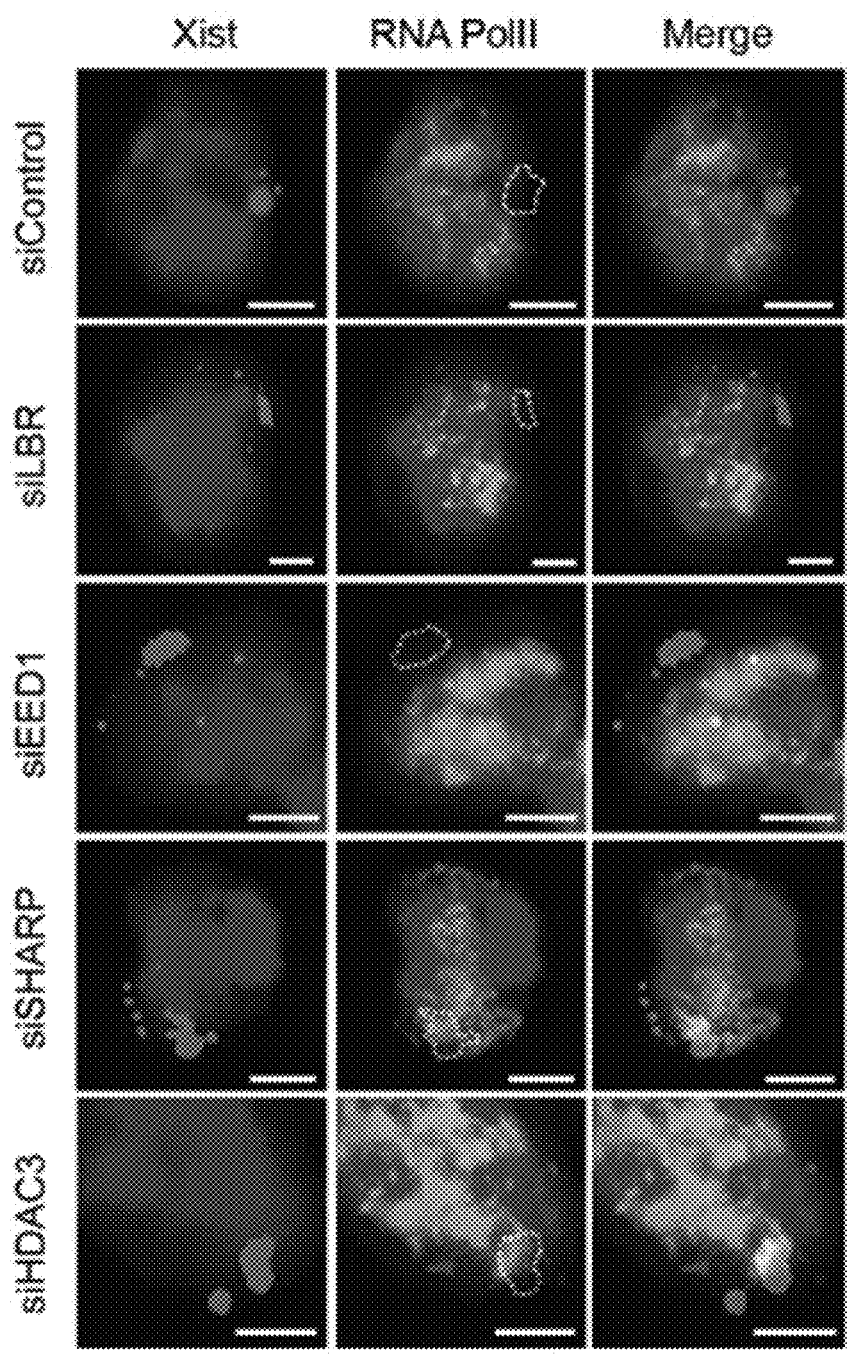
FIG. 16 show representative mages of individual cells that are labeled with Xist (red), RNA Polymerase II (green), and DAPI (blue) across different siRNA conditions (rows) in female ES cells after 24 hours of retinoic acid treatment, with the dashed white region representing the outlined Xist coated territory, according to embodiments of the present invention.

To determine the proteins responsible for establishing the initial silenced compartment on the X-chromosome, the requirement of SHARP or LBR was explored for the exclusion of PolII from the Xist-coated region. Specifically, the co-localization of Xist and PolII was measured in single cells. In wild-type cells after 16 hours of Xist induction, a depletion of PolII was observed over the Xist-coated territory (FIG. 15A). A similar exclusion of PolII from the Xist-coated region in the negative controls and upon knockdown of EED or LBR (FIGS. 15A-15B). In contrast, upon knockdown of SHARP, higher levels of PolII were observed over the Xist-coated territory relative to the control samples (FIG. 15B). It was confirmed that SHARP, but not LBR or EED, is similarly required for PolII exclusion in differentiating female ES cells (FIG. 15C, FIG. 16).

These results demonstrate that SHARP is required to exclude PolII on the inactive X-chromosome and may be required for creating the initial silenced compartment upon Xist localization.

Having identified SHARP as the direct Xist-interacting protein that is required for excluding PolII on the X-chromosome, the next step was to determine how it might carry out this role. SHARP is a direct RNA binding protein that was first identified in mammals based on its interaction with the SMRT co-repressor complex6, which is known to interact with HDAC3 and is required for activating its deacetylation and transcriptional silencing activity in vivo. Based on these previous observations, it was hypothesized that Xist-mediated transcriptional silencing through SHARP would occur through SMRT and the silencing function of HDAC3.

To test this hypothesis, either SMRT or HDAC3 was knocked down and the expression of X-chromosome genes was measured upon Xist induction. Knockdown of SMRT or HDAC3 in both male and female ES cells abrogated silencing of X-chromosome genes upon induction of Xist expression (FIG. 5A, FIGS. 6A-6D, FIGS. 14A-14B). To ensure that the observed silencing defect is specific for HDAC3 and not for other class I HDAC proteins, HDAC1 or HDAC2 was knocked down and no effect on gene silencing (FIGS. 6A-6B) was observed. To further confirm the specificity of these results, independent siRNAs were used to knock down SMRT or HDAC3 and in all cases identified a similar silencing defect (FIGS. 6C-6D).

To determine whether this effect is similar to the effect produced by knock down of SHARP or a distinct defect in transcriptional silencing, it was tested whether HDAC3, the silencing protein in this complex is required for the exclusion of RNA PolII from the Xist-coated territory. It was found that knock down of HDAC3 in both male and female ES cells eliminated the exclusion of RNA PolII from the Xist-coated compartment to a similar degree to that seen for knock down of SHARP (FIGS. 15A-15C, FIG. 16).

These results suggest that SHARP silences transcription through SMRT and the HDAC3 silencing protein. This role for HDAC3 in Xist-mediated silencing would explain the long-standing observation of global hypoacetylation on the entire X-chromosome as one of the very first events that occur upon initiation of XCI.

Example 6

Additional Characterization of SHARP

Figure 12A:
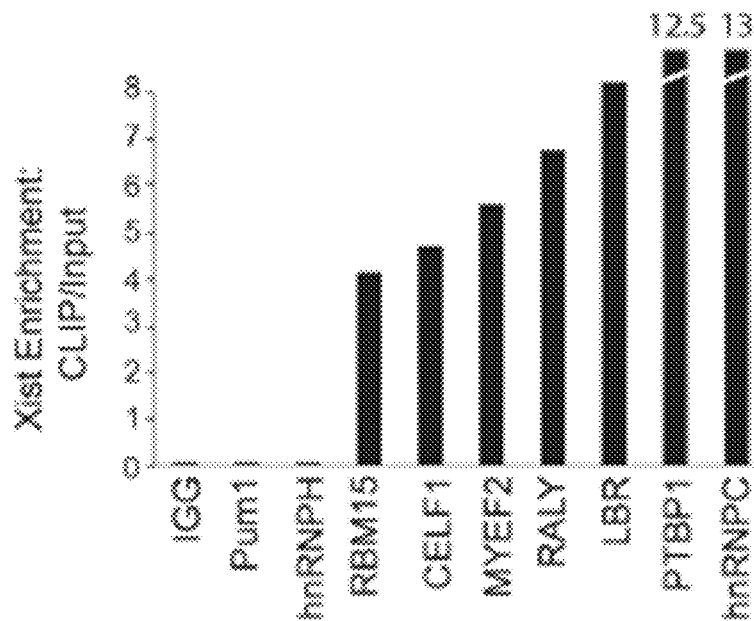
FIGS. 12A-12D show results from RNA immunoprecipitation experiments performed for seven Xist-interacting proteins (black bars), two control RNA binding proteins that were not identified by RAP-MS and IgG (gray bars) in UV-crosslinked cell lysate after 6 hours of Xist induction by doxycycline addition according to method described herein, in which the RNA associated with each protein was measured and enrichment levels were computed relative to the level of the RNA in total cellular input and normalized to the total efficiency of capture in each sample to allow for direct comparison across all IP experiments, according to embodiments of the present invention.
Figure 12B:
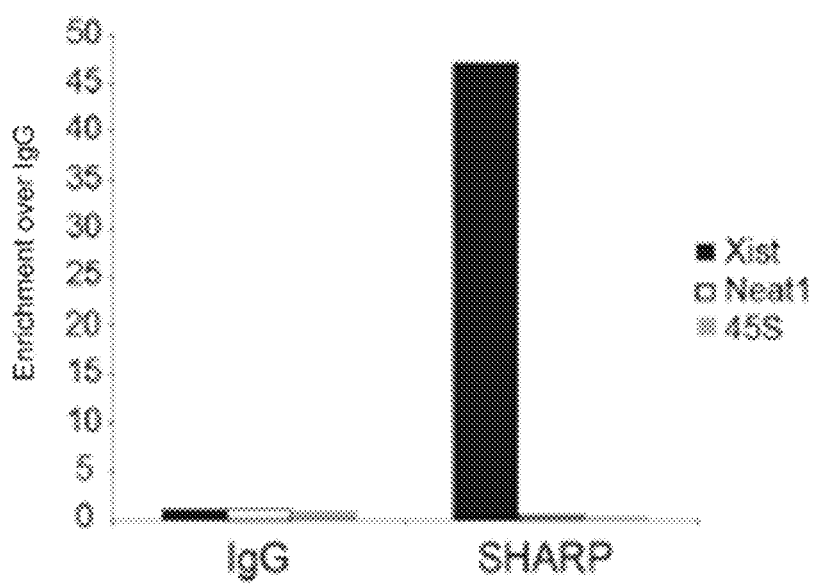
Figure 12C:
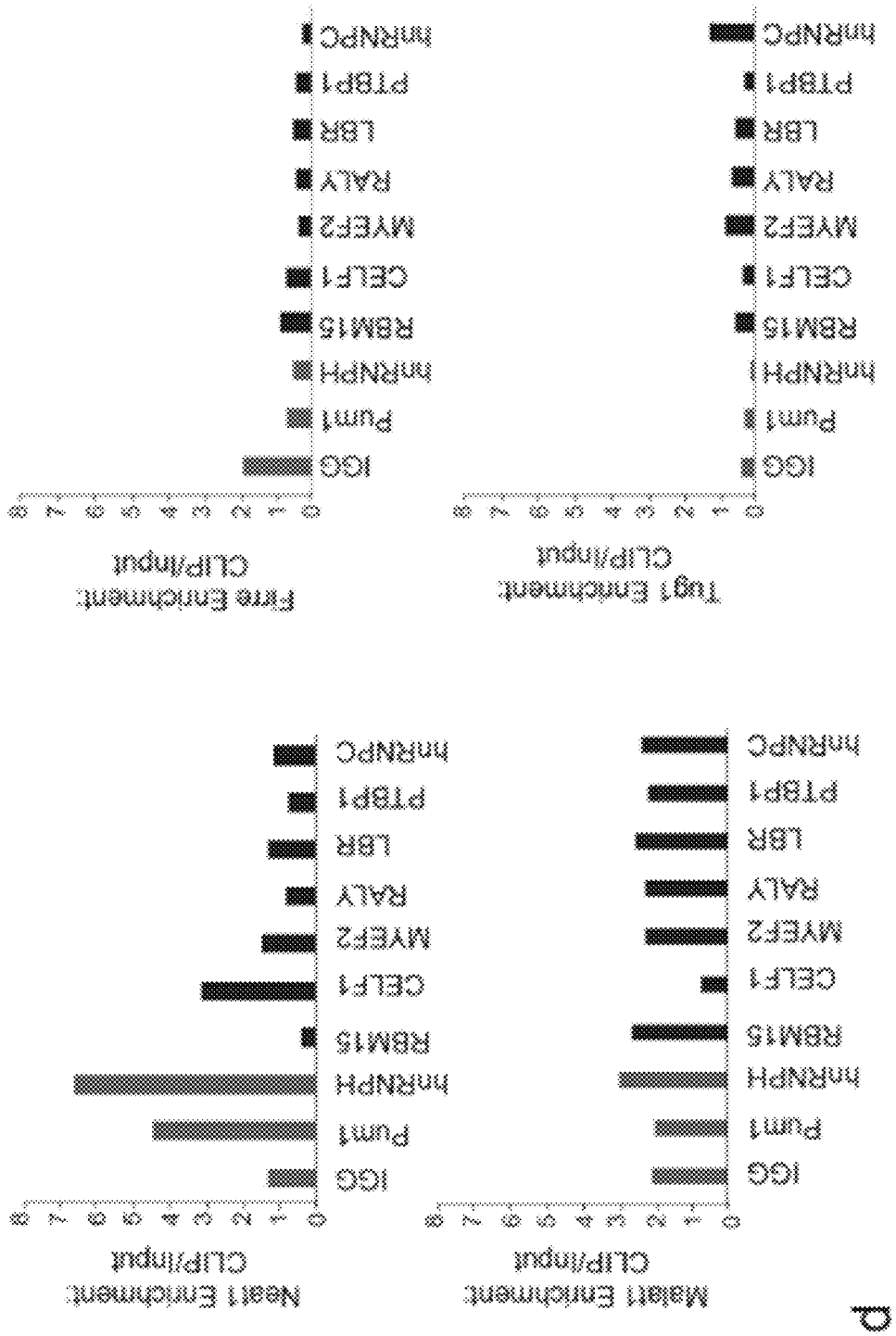
Figure 12D:
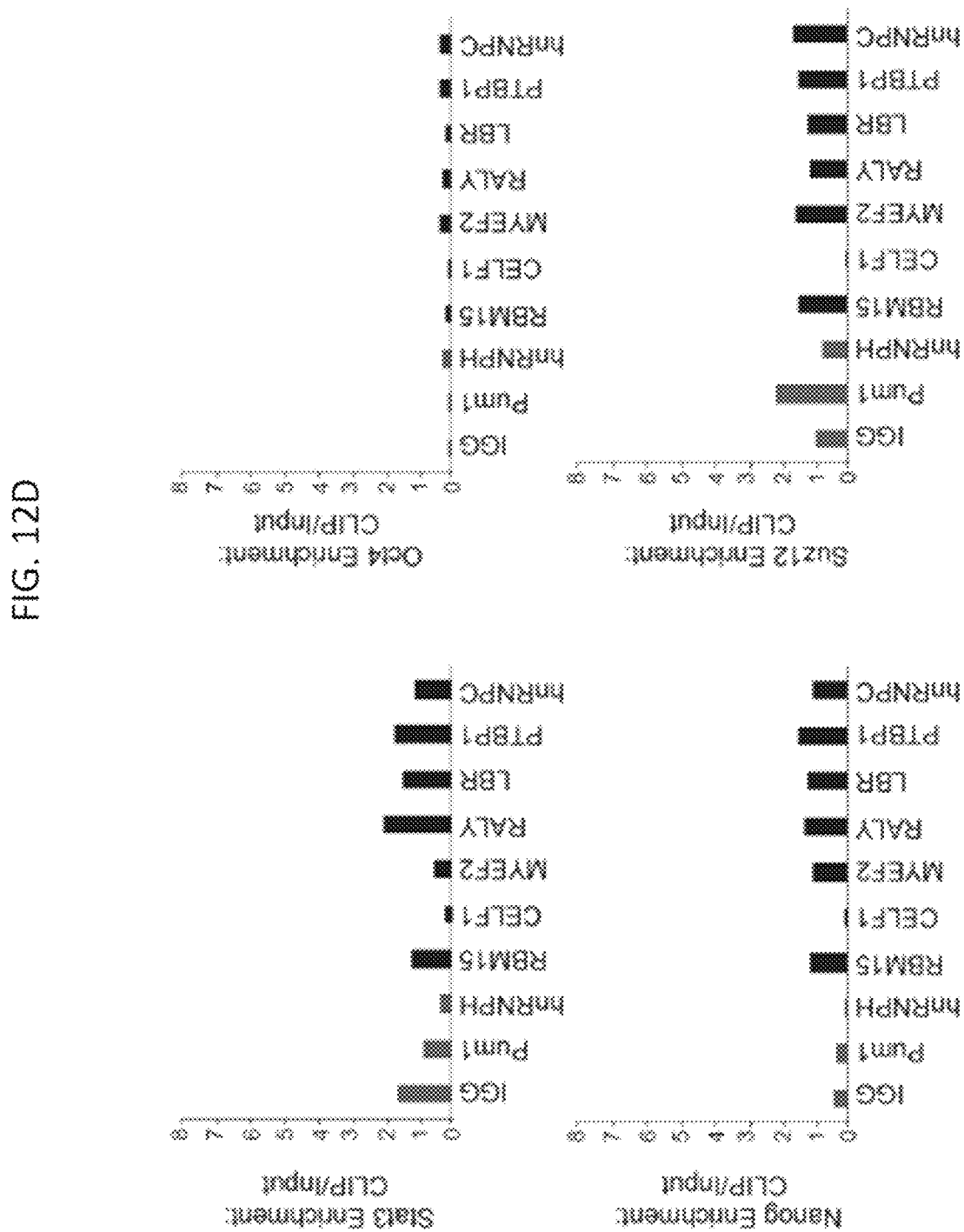

Having identified a critical role for SHARP in PolII exclusion, further confirmation of the functional importance of SHARP was investigated. (i) It was confirmed that SHARP is required for silencing additional X-chromosome genes by selecting three additional genes (Rbmx, Mecp2, and Smc1a) that are silenced at different times during the induction of XCI. Knockdown of SHARP abolished the silencing of all 3 additional X-chromosome genes. In contrast, knockdown of SHARP had no impact on the expression of two X-chromosome genes (Mid1 and Pir) that are known to escape XCI11 (FIGS. 13A-13B). (ii) It was confirmed that SHARP similarly interacts with Xist in differentiating female ES cells. To do this, SHARP was purified from lysates of UV-crosslinked retinoic acid (RA)-treated female ES cells and identified a strong enrichment for Xist (>45-fold) but not for Neat1 or 45S (<1-fold) relative to levels in IgG (FIG. 12B). (iii) It was confirmed that SHARP, but not LBR, is similarly required for PolII exclusion in differentiating female ES cells. SHARP, LBR, and several controls were knocked down in female ES cells and induced Xist expression through RA-treatment and identified higher levels of PolII localization over the Xist-coated territory upon knock down of SHARP, but not the other proteins (FIG. 15C, FIG. 16).

While it is clear that SHARP and HDAC3 are required for the recruitment of PRC2, whether this is due to direct recruitment or indirect recruitment remains unclear. Previous studies suggest several possible mechanisms: (i) PolII exclusion has been shown to be sufficient to trigger PRC2 recruitment in other contexts and because SHARP is required for PolII exclusion on the X-chromosome, this might indirectly lead to PRC2 recruitment. (ii) Previous studies have shown that the PRC2 complex can interact with various HDAC complexes and accordingly PRC2 might be recruited directly by Xist through the HDAC3 complex. (iii) Chromatin compaction has been shown to be sufficient to mediate PRC2 recruitment because HDAC3 can lead to chromatin compaction this may indirectly lead to PRC2 recruitment. (iv) SHARP has been shown to interact in vitro with RbAp4815, a component of several chromatin regulatory complexes including the PRC2 and HDAC3 complexes and therefore Xist might directly recruit PRC2 through an interaction between SHARP or HDAC3 and RbAp48 and the PRC2 complex.

Example 7

Recruitment of PRC2

One of the features of XCI is the recruitment of PRC2 and its associated H3K27me3 repressive chromatin modifications across the X-chromosome in an Xist-dependent manner. While PRC2 is not required for the initiation of XCI (FIG. 15B), it or its associated H3K27me3 repressive chromatin modifications may be involved in establishing an epigenetically silenced state. Yet, how Xist recruits the PRC2 complex across the X-chromosome is unknown. Since there were no identifications of any PRC2 components by RAP-MS, and various HDAC complexes are known to recruit PRC2, it was hypothesized that PRC2-recruitment is mediated by SHARP and HDAC3.

Figure 17A:
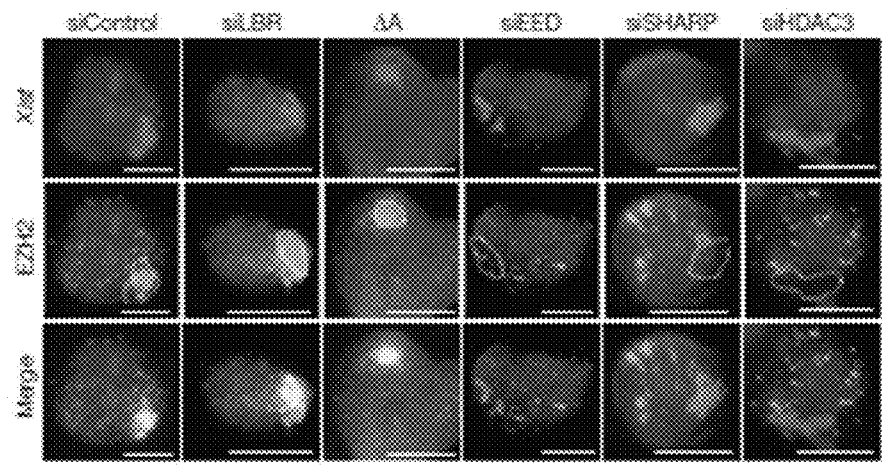
FIG. 17A show representative fluorescent imaging of ES cells labeled for Xist (red), Ezh2 (green) and DAPI (blue) across siRNA conditions (rows), according to embodiments of the present invention.
Figure 17B:
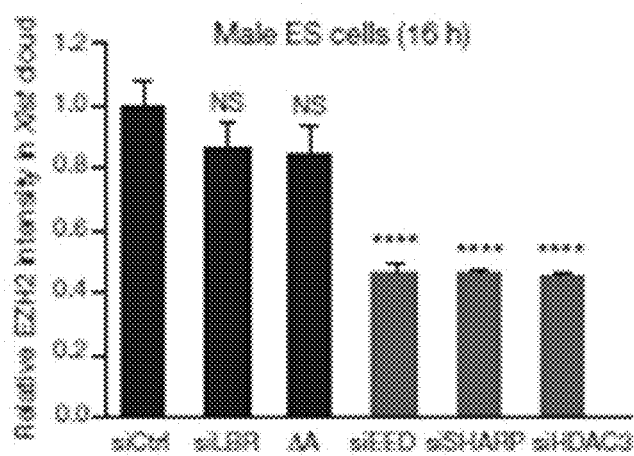
FIG. 17B is a graph of the quantification of fluorescence intensity of PolII within Xist territory normalized to control siRNA levels for male ES cells after 16 hours of doxycycline treatment, according to embodiments of the present invention.
Figure 17C:
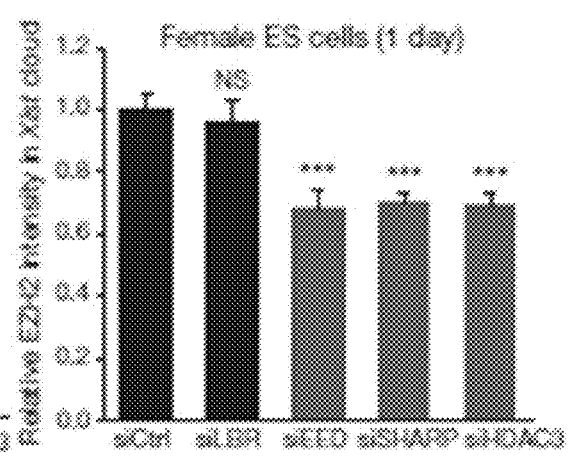
FIG. 17C is a graph of the quantification of fluorescence intensity of PolII within Xist territory normalized to control siRNA levels for female ES cells after 1 day of retinoic acid induced differentiation, according to embodiments of the present invention.
Figure 18:
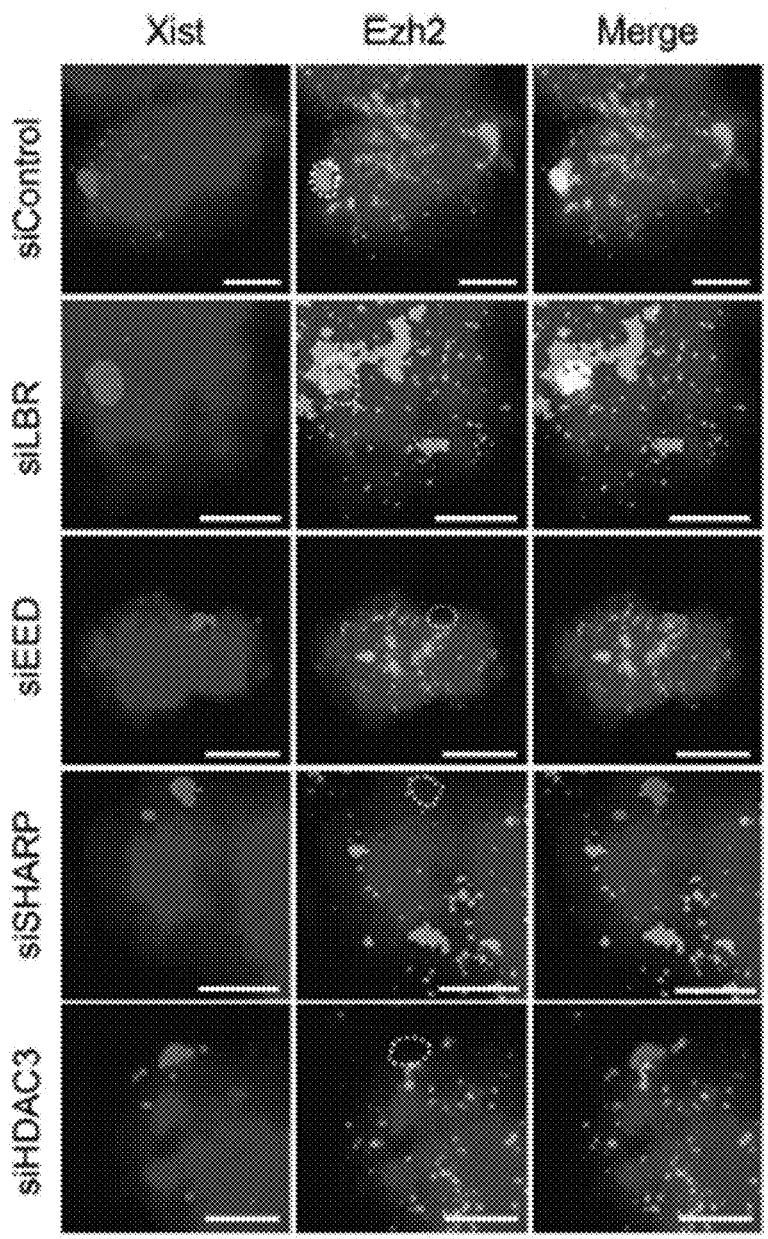
FIG. 18. shows representative images of individual cells that are labeled with Xist (red), Ezh2 (green) and DAPI (blue) across different siRNA conditions (rows) in female ES cells after 24 hours of differentiation with the dashed white region represents the outlined Xist coated territory, according to embodiments of the present invention.

To test this hypothesis, PRC2 recruitment to the Xist-coated territory was investigated. In wild-type cells, a strong enrichment of EZH2 (a component of PRC2) was observed over the Xist-coated territory after 16 hours of induction (FIG. 17A). Upon knock down of EED, a distinct component of the PRC2 complex that is required for its proper localization to chromatin, no enrichment of EZH2 over the Xist cloud was observed at this same time point (FIG. 17A). Similarly, upon knock down of SHARP, a loss of EZH2 was identified over the Xist coated territory, of comparable magnitude to that observed in the absence of EED (FIG. 17A). Conversely, upon knock down of LBR, a strong enrichment of EZH2 was observed over the Xist coated territory, of comparable magnitude to the levels of recruitment in wild-type conditions (FIG. 17B). To determine whether HDAC3 is required for PRC2 recruitment, HDAC3 was knocked down and a loss of PRC2 recruitment was observed (FIG. 17A), of comparable magnitude to that observed upon loss of SHARP (FIG. 17B). Knockdown of SHARP or HDAC3 led to the same PRC2-recruitment defect in female ES cells (FIG. 17C, FIG. 18).

These results argue that Xist-mediated recruitment of PRC2 across the X-chromosome is dependent on SHARP and HDAC3. Whether this occurs through an interaction with SHARP or HDAC3 (direct recruitment) or due to the HDAC3-induced silenced transcription state, chromatin modifications, or compact chromatin structure (indirect recruitment) remains unclear. Yet, the results are in contrast to a previous model that PRC2 is recruited through a direct interaction between EZH2 and the A-repeat of Xist. The evidence for this PRC2-Xist interaction is based on in vitro binding and purifications in non-denaturing conditions. Recently, the specificity of this interaction has been questioned because PRC2 appears to bind promiscuously to many RNAs, including bacterial RNAs, in these conditions. Instead, the results here are consistent with reports that deletion of the A-repeat, unlike knockdown of SHARP or HDAC3, has no significant effect on PRC2 recruitment to the Xist-coated territory (FIG. 17B).

Taken together, the data here suggest a model for how Xist can orchestrate transcriptional silencing on the X-chromosome (FIG. 1A). Upon initiation of Xist expression, Xist can localize to sites on the X-chromosome by binding to the SAF-A protein, which is known to interact directly with chromatin. Xist directly interacts with SHARP to recruit SMRT to these DNA sites across the inactive X-chromosome. This Xist-SHARP-SMRT complex either directly recruits HDAC3 to the X-chromosome or may act to induce the enzymatic activity of HDAC3 that may already be present at active genes across the X-chromosome. Through HDAC3, Xist can direct the removal of activating histone acetylation marks on chromatin thereby compacting chromatin and silencing transcription. Upon initiating the silenced state, Xist recruits PRC2 across the X-chromosome in an HDAC3-dependent manner, either through a direct interaction between PRC2 and HDAC3 or indirectly through HDAC3-induced transcriptional silencing or chromatin compaction. In this way, the same Xist interacting protein might achieve two essential roles in XCI—initiating the inactive state by recruiting transcriptional silencers (HDAC3) and maintaining the inactive state by recruiting stable epigenetic silencers (PRC2). Beyond Xist, RAP-MS provides a critical tool that will accelerate the discovery of novel lncRNA mechanisms that have thus far proved elusive.

Example 8

Materials and Methods for Examples 1-7

Mouse ES Cell Culture.

All mouse ES cell lines were cultured in serum-free 2i/LIF medium as previously described 13. The following cell lines were used: (i) Wild-type male ES cells (V6.5 line); (ii) Male ES cells expressing Xist from the endogenous locus under control of a tet-inducible promoter (pSM33 ES cell line) as described in Engreitz et al., supra. (iii) Male ES cells carrying a cDNA Xist transgene without the A-repeat integrated into the Hprt locus under control of the tet-inducible promoter (A-repeat deletion: kindly provided by A. Wutz). (iv) Female ES cells (F1 2-1 line). This wild-type female mouse ES cell line is derived from a 129× castaneous F1 mouse cross as previously described in Engreitz et al., supra.

Xist Induction.

For Dox inducible cells (pSM33 and A-repeat deletion), Xist expression was induced by treating cells with 2 μg/ml doxycycline (Sigma) for 6 hours, 16 hours, or 24 hours based on the application. For female ES cells (F1 2-1 line), Xist expression was induced by inducing differentiation; 2i was replaced with MEF media (DMEM, 10% Gemini Benchmark FBS, 1×L-glutamine, 1×NEAA, 1× Pen/Strep; Life Technologies unless otherwise indicated) for 24 hours followed by treatment with 1 μM retinoic acid (RA) (Sigma) for an additional 24 hours.

The amount of Xist RNA was measured in both the doxycycline-inducible cells (6 hours induction) and differentiating female ES cells (24 hour induction) by qRT-PCR. This level was normalized to various RNA housekeeping controls, 18S, 28S, and U6, in both cell populations and calculated the fold expression difference between male and female cells using the comparative Ct method. A range of expression was observed, with the male inducible system expressing from 5-20 fold (12-fold average) more Xist than the female cells. It is noted that this estimate likely represents an upper limit of the actual differences because the female ES cell system is known to be heterogeneous in Xist-induction, such that not every cell will induce Xist to the same level after 24 hours of retinoic acid treatment. Accordingly, the actual differences that are expected between the male inducible system and differentiating female ES cells are actually significantly lower. While the precise levels are hard to compare by single molecule FISH, the size and intensity of each Xist RNA cloud is similar in both systems at the time points used.

The male-inducible system is more sensitive for identifying proteins that affect silencing compared to a female system because Xist-mediated silencing in males will lead to loss of 100% of X-chromosome transcripts rather than only 50% in a female system, which still retains one active X.

UV Crosslinking.

Cells were washed once with PBS and then crosslinked on ice using 0.8 Joules/cm2 (UV8k) of UV at 254 nm in a Spectrolinker UV Crosslinker. Cells were then scraped from culture dishes, washed once with PBS, pelleted by centrifugation at 1500×g for 4 minutes, and flash frozen in liquid nitrogen for storage at −80° C.

SILAC ES Cell Culture.

For SILAC experiments, the ES cell culture procedures were adapted to incorporate either light or heavy lysine and arginine amino acids. The 2i/LIF SILAC medium was composed as follows: custom DMEM/F-12 without lysine or arginine (Dundee Cell Products) was supplemented with either 0.398 mM heavy Arg10 (Sigma) or unlabeled arginine (Sigma) and either 0.798 mM heavy Lys8 (Cambridge Isotope Labs) or unlabeled lysine (Sigma), 0.5×B-27 (Gibco), 2 mg/mL bovine insulin (Sigma), 1.37 g/mL progesterone (Sigma), 5 mg/mL BSA Fraction V (Gibco), 0.1 mM 2-mercaptoethanol (Sigma), 5 ng/mL murine LIF (GlobalStem), 0.1 μM PD0325901 (SelleckChem) and 0.3 μM CHIR99021 (SelleckChem). Cells in both heavy and light 2i/LIF SILAC medium were also supplemented with 0.2 mg/mL of unlabeled proline (Sigma) to prevent conversion of labeled arginine to proline. 2i inhibitors were added fresh with each medium change.

Adapting Cells to SILAC Conditions.

Prior to mass spectrometry, ES cells were adapted to SILAC conditions over three passages. The heavy or light culture medium was replaced every 24-48 hours depending on cell density, and cells were passaged every 72 hours using 0.025% trypsin (Gibco), rinsing dissociated cells from the plates with DMEM/F12 containing 0.038% BSA Fraction V (Gibco). Cells were grown in two different types of medium: (i) 2i/LIF SILAC medium with light (unlabeled) lysine and arginine, or (ii) 2i/LIF SILAC medium with heavy isotope labeled lysine and arginine.

Measuring SILAC Incorporation.

Figure 9B:
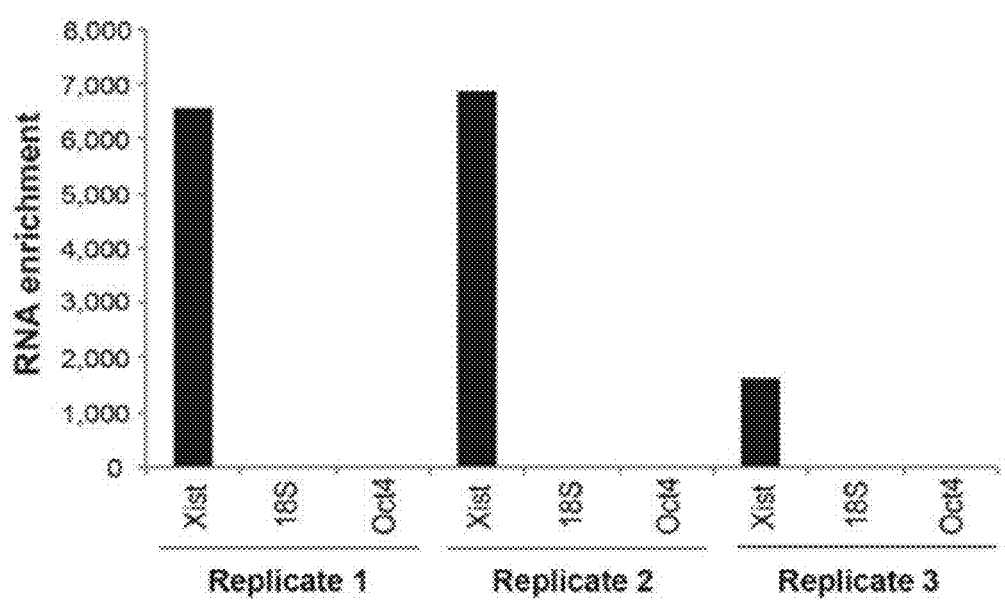
FIG. 9B is graph plotting enrichment of Xist after RAP-MS captures from pSM33 cells as measured by qPCR, with bars indicating RNA levels of Xist, 18S, and Oct4 after purification of Xist, normalized to RNA in input sample, and each bar represents the RNA levels of Xist, 18S, and Oct4 after purification of Xist, normalized to RNA in input sample, from 3 biological replicates, according to embodiments of the present invention.
Figure 9C:
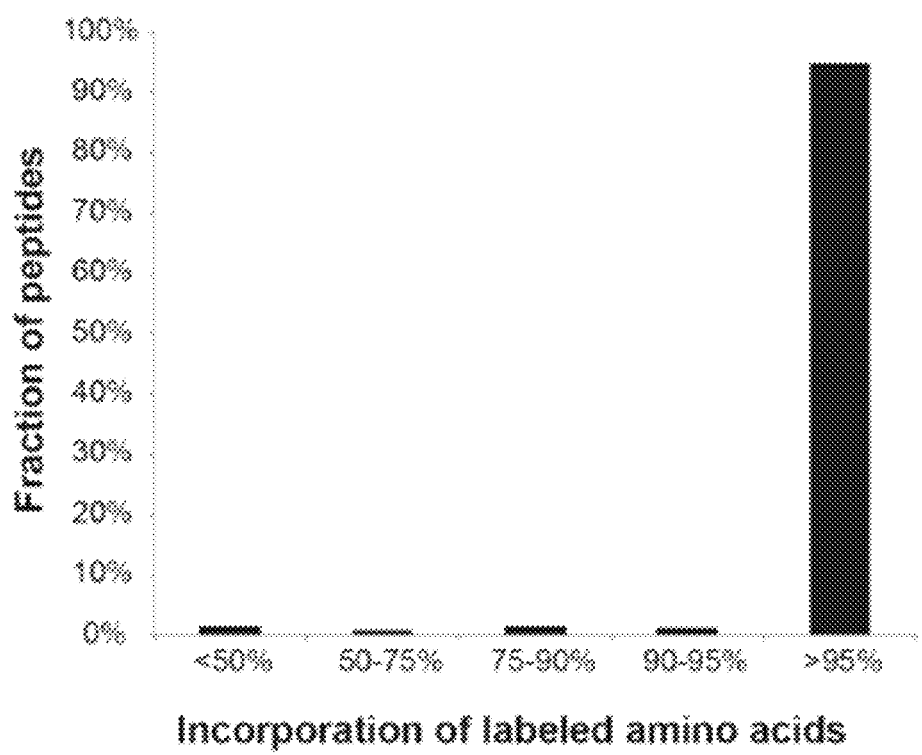
FIG. 9C is graph plotting SILAC labeling efficiency of a representative culture of pSM33 mouse ES cells after 10 days of growth (3 cell passages) in SILAC medium, in which peptides were analyzed by mass spectrometry, and values indicate the fraction of identified peptides with heavy-label incorporation with different levels of peptide labeling (shown in bins), according to embodiments of the present invention.

To examine the efficiency of SILAC labeling in pSM33 cells, the incorporation of labeled amino acids was tested after 10 days of growth (3 cell passages) in heavy 2i/LIF SILAC medium. Pellets of 2 million cells were boiled for 10 minutes in LDS Sample Loading Buffer (Invitrogen) and then proteins were separated by SDS-PAGE on a 4-12% Tris-Glycine polyacrylamide gel (Invitrogen). Total protein was stained with Colloidal Coomassie (Invitrogen) and gel slices were excised with a clean scalpel and transferred to microcentrifuge tubes for in-gel tryptic digest. Protein disulfide bonds were reduced with DTT then alkylated with iodoacetamide. Proteins were digested with trypsin overnight and then extracted using successive washes with 1% formic acid/2% acetonitrile, 1:1 acetonitrile/water, and 1% formic acid in acetonitrile. Peptides were collected, lyophilized, then resuspended in 1% formic acid for mass spectrometry analysis (described below in Mass Spectrum Measurements). Peptides were identified from mass spectra using MaxQuant (described below in MS data analysis). The incorporation rate of labeled amino acids was calculated based on the ratio of the intensity of heavy and light versions of each peptide identified. In cells used for subsequent assays, it was confirmed that over 95% of peptides from cellular proteins showed >95% incorporation of labeled amino acids (FIG. 9B).

RNA Affinity Purification-Mass Spectrometry (RAP-MS).

Probe Design and Generation.

To create the probes used to capture target RNAs, 90-mer DNA oligonucleotides (Eurofins Operon) were designed and synthesized that spanned the entire length of the target RNA. The sequence of each DNA oligonucleotide probes was antisense to the complementary target RNA sequence. Each DNA oligonucleotide probe was also modified with a 5' biotin in order to enable capture of DNA-RNA hybrids on streptavidin coated magnetic beads (described below). While 120-mer probes were previously used, it was found that 90-mer probes provided comparable stringency and yield in the conditions used. For Xist, 142 probes were used that covered the entire mature RNA sequence, with the exception of regions that match to other transcripts or genomic regions as previously described.

Total Cell Lysate Preparation.

For the 18S and U1 experiments total cellular lysates were used that were prepared in the following manner. Batches of 20 million cells were lysed by completely resuspending frozen cell pellets in ice cold detergent-based Cell Lysis Buffer (10 mM Tris pH 7.5, 500 mM LiCl, 0.5% dodecyl maltoside (DDM, Sigma), 0.2% sodium dodecyl sulfate (SDS, Ambion), 0.1% sodium deoxycholate (Sigma)). Next, 1× Protease Inhibitor Cocktail (Set III, EDTA-free, Calbiochem) and 920 U of Murine RNase Inhibitor (New England Biolabs) were added and the sample was incubated for 10 minutes on ice to allow lysis to proceed. During this incubation period, the cell sample was passed 3-5× through a 26-gauge needle attached to a 1 mL syringe in order to disrupt the pellet and shear genomic DNA. Each sample was then sonicated using a Branson Digital Sonifier with a microtip set at 5 watts power for a total of 30 seconds in intermittent pulses (0.7 seconds on, 1.3 seconds off). During sonication the samples were chilled to prevent overheating of the lysate. The samples were then treated for 10 minutes at 37° C. with 2.5 mM MgCl2, 0.5 mM CaCl2, and 20 U of TURBO DNase (Ambion) to digest DNA. Samples were returned to ice and the reaction was immediately terminated by the addition of 10 mM EDTA and 5 mM EGTA. Disulfide bonds were reduced by addition of 2.5 mM Tris-(2-carboxyethyl) phosphine (TCEP) and samples were then mixed with twice the lysate volume of 1.5×LiCl/Urea Buffer (the final 1× Buffer contains 10 mM Tris pH 7.5, 5 mM EDTA, 500 mM LiCl, 0.5% DDM, 0.2% SDS, 0.1% deoxycholate, 4M urea, 2.5 mM TCEP). Lysates were incubated on ice for 10 minutes then cleared by centrifugation in an Eppendorf 5424R centrifuge for 10 minutes at 16,000×g. Supernatants were pooled and flash frozen in liquid nitrogen for storage at −80° C.

Nuclear Lysate Preparation.

For the Xist versus U1 and 45S versus U1 comparisons, used nuclear lysates were prepared in the following manner. Batches of 50 million cells were lysed by resuspending frozen pellets in 1 mL Lysis Buffer 1 (10 mM HEPES pH7.2, 20 mM KCl, 1.5 mM MgCl2, 0.5 mM EDTA, 1 mM Tris(2-carboxyethyl)phosphine (TCEP), 0.5 mM PMSF). Then the samples were centrifuged at 3,300×g for 10 minutes to pellet cells. The cell pellets were resuspended in 1 mL Lysis Buffer 1 with 0.1% dodecyl maltoside (DDM) and dounced 20 times using a glass dounce homogenizer with the small clearance pestle (Kontes). Nuclei released from the cells after douncing were pelleted by centrifugation at 3,300×g then resuspended in 550 μl Lysis Buffer 2 (20 mM Tris pH 7.5, 50 mM KCl, 1.5 mM MgCl2, 2 mM TCEP, 0.5 mM PMSF, 0.4% sodium deoxycholate, 1% DDM, and 0.1% N-lauroylsarcosine (NLS)). Samples were incubated on ice for 10 minutes, then each sample was sonicated using a Branson Sonifier at 5 watts power for a total of 1 minute in intermittent pulses (0.7 seconds on, 3.3 seconds off) to lyse nuclei and solubilize chromatin. During sonication the samples were chilled to prevent overheating of the nuclear lysate. Samples were then treated with 2.5 mM MgCl2, 0.5 mM CaCl2, and 330 U TURBO DNase (Ambion) for 12 minutes at 37° C. to further solubilize chromatin. After DNase treatment, lysates were mixed with equal volume of 2× Hybridization Buffer (the final 1× Buffer contains 10 mM Tris pH 7.5, 5 mM EDTA, 500 mM LiCl, 0.5% DDM, 0.2% SDS, 0.1% deoxycholate, 4M urea, 2.5 mM TCEP). Finally, lysates were cleared by centrifugation for 10 minutes at 16,000×g in an Eppendorf 5424R centrifuge and the resulting supernatants were pooled and flash frozen in liquid nitrogen for storage at −80° C.

RNA Affinity Purification of Crosslinked Complexes.

Lysates from 200 million or 800 million cells were used for each capture. For 200 million cells the following protocol was used, and scaled appropriately for larger cell numbers. For each capture, a sample of heavy or light SILAC labeled frozen lysate was warmed to 37° C. For each sample, 1.2 mL of Streptavidin Dynabeads MyOne C1 magnetic beads (Invitrogen) were washed 6 times with equal volume of hybridization buffer (10 mM Tris pH 7.5, 5 mM EDTA, 500 mM LiCl, 0.5% DDM, 0.2% SDS, 0.1% deoxycholate, 4M urea, 2.5 mM TCEP). Lysate samples were pre-cleared by incubation with the washed Streptavidin C1 magnetic beads at 37° C. for 30 minutes with intermittent shaking at 1100 rpm on a Eppendorf Thermomixer C (30 seconds mixing, 30 seconds off). Streptavidin beads were then magnetically separated from lysate samples using a Dynamag magnet (Life Technologies). The beads used for pre-clearing lysate were discarded and the lysate sample was transferred to fresh tubes twice to remove all traces of magnetic beads. Biotinylated 90-mer DNA oligonucleotide probes specific for the RNA target of interest (20 µg per sample, in water) were heat-denatured at 85° C. for 3 minutes and then snap-cooled on ice. Probes and pre-cleared lysate were mixed and incubated at 67° C. using an Eppendorf thermomixer with intermittent shaking (30 seconds shaking, 30 seconds off) for 2 hours to hybridize probes to the capture target RNA. Hybrids of biotinylated DNA probes and target RNA were then bound to streptavidin beads by incubating each sample with 1.2 mL of washed Streptavidin coated magnetic beads at 67° C. for 30 minutes on an Eppendorf Thermomixer C with intermittent shaking as above. Beads with captured hybrids were washed 6 times with LiCl/Urea Hybridization Buffer at 67° C. for 5 minutes to remove non-specifically associated proteins. Between 0.5-1% of the total beads were removed and transferred to a fresh tube after the final wash to examine RNA captures by qPCR (see "Elution and analysis of RNA samples"). The remaining beads were resuspended in Benzonase Elution Buffer (20 mM Tris pH 8.0, 2 mM MgCl2, 0.05% NLS, 0.5 mM TCEP) for subsequent processing of the protein samples.

Elution of Protein Samples.

Elution of captured proteins from streptavidin beads was achieved by digesting all nucleic acids (both RNA and DNA, double-stranded and single-stranded) using 125 U of Benzonase nonspecific RNA/DNA nuclease for 2 hours at 37° C. (Millipore, #71206-3). Beads were then magnetically separated from the sample using a DynaMag magnet (Life Technologies) and the supernatant containing eluted Xist-specific proteins were precipitated overnight at 4° C. with 10% trichloroacetic acid (TCA). TCA treated protein elution samples were pelleted by centrifugation for 30 minutes at >20,000×g, then washed with 1 mL cold acetone and recentrifuged. Final protein elution pellets were air dried to remove acetone and stored at −20° C. until processing for mass spectrometry.

Elution and Analysis of RNA Samples.

Beads with hybrids were magnetically separated using a 96-well DynaMag (Life Technologies) and the supernatant was discarded. Beads were then resuspended by pipetting in 20 µL NLS RNA Elution Buffer (20 mM Tris pH 8.0, 10 mM EDTA, 2% NLS, 2.5 mM TCEP). To release the target RNA, beads were heated for 2 minutes at 95° C. in an Eppendorf Thermomixer C. Beads were then magnetically separated using a 96-well DynaMag (Life Technologies) and the supernatants containing eluted target RNA were digested by the addition of 1 mg/mL Proteinase K for 1 hour at 55° C. to remove all proteins. The remaining nucleic acids were then purified by ethanol precipitation onto SILANE beads (Invitrogen) as previously described13,32. DNA probes were removed by digestion with TURBO DNase (Ambion). To quantify RNA yield and enrichment, qPCR was performed as previously described in Engreitz et al., supra.

Mass Spectrometry Analysis

Preparation of Proteins for Mass Spectrometry.

Proteins from RAP-MS captures were resuspended in fresh 8 M urea dissolved in 40 µL of 100 mM Tris-HCl pH 8.5. Disulfide bonds were reduced by incubation with 3 mM TCEP for 20 minutes at room temperature, followed by alkylation with 11 mM iodoacetamide for 15 minutes at room temperature in the dark. Samples were then digested with 0.1 µg endoproteinase Lys-C for 4 hours at room temperature. After Lys-C digestion the samples were diluted to a final concentration of 2M urea by the addition of 100 mM Tris-HCl pH 8.5, and CaCl2 was added to a final concentration of 1 mM. Tryptic peptides were generated by treatment with 0.1 to 0.5 µg of trypsin overnight at room temperature. Contaminating detergents were removed from peptides using HiPPR detergent removal columns (Thermo), and peptides were protonated by the addition of 5%/o formic acid before desalting on a Microm Bioresources C8 peptide MicroTrap column. Peptide fractions were collected and lyophilized, and dried peptides were resuspended in 0.2% formic acid with 5% acetonitrile.

Mass Spectrum Measurements.

Liquid chromatography-mass spectrometry and data analyses of the digested samples were carried out as previously described in Wutz et al., 2014, Nature Genet. 30:167-174, the entire content of which is herein incorporated by reference, with the following modifications. All experiments were performed on a nanoflow LC system, EASY-nLC 1000 coupled to a hybrid linear ion trap Orbitrap Elite mass spectrometer (Thermo Fisher Scientific, Bremen, Germany) equipped with a nanoelectrospray ion source (Thermo Fisher Scientific). For the EASY-nLC II system, solvent A consisted of 97.8% H2O, 2%/o ACN, and 0.2% formic acid and solvent B consisted of 19.8% H2O, 80% ACN, and 0.2% formic acid. For the LC-MS/MS experiments, 200 ng of digested peptides were directly loaded at a flow rate of 500 nL/min onto a 16-cm analytical HPLC column (75 µm ID) packed in-house with ReproSil-Pur C18AQ 3 µm resin (120 Å pore size, Dr. Maisch, Ammerbuch, Germany). The column was enclosed in a column heater operating at 30° C. After 30 min of loading time, the peptides were separated with a 75 min gradient at a flow rate of 350 nL/min. The gradient was as follows: 0-2% Solvent B (5 min), 2-30% B (60 min), and 100% B (10 min). The Elite was operated in data-dependent acquisition mode to automatically alternate between a full scan (m/z=400-1600) in the Orbitrap and subsequent rapid 20 CID MS/MS scans in the linear ion trap. CID was performed with helium as collision gas at a normalized collision energy of 35% and 10 ms of activation time.

MS Data Analysis.

Thermo RAW files were searched with MaxQuant (v 1.5.0.30)34,35. Spectra were searched against all UniProt mouse entries (43,565 entries, downloaded 2 Oct. 2014) and MaxQuant contaminant database (245 entries). Decoy sequences (reversed peptide sequences) were generated in MaxQuant to estimate the false discovery rate36. Search parameters included multiplicity of 2 with heavy Arg (+10.0083) and heavy Lys (+8.0142) as heavy peptide modifications. Variable modifications included oxidation of Met (+15.9949) and protein N-terminal acetylation (+42.0106). Carboxyamidomethylation of Cys (+57.0215) was specified as a fixed modification. Protein and peptide false discovery rates were thresholded at 1%. Precursor mass tolerance was 7 ppm (or less for individual peptides). Fragment mass tolerance was 0.5 Da. Requantify and match between runs were both enabled. Trypsin was specified as the digestion enzyme with up to 2 missed cleavages.

Identification of RNA Interacting Proteins.

Proteins of interest from RAP-MS captures were identified based on several criteria. First, proteins were considered identified only if 2 or more unique peptides were found in the mass spectrum. Then proteins of interest were selected based on the SILAC ratio of capture versus control samples. SILAC ratios for each peptide were calculated based on the intensity ratios of heavy and light SILAC pairs. The protein ratio is the median of all calculated peptide ratios, with a minimum of two SILAC pairs required for a SILAC ratio to be assigned to a given protein. A SILAC ratio cutoff of ≥3.0 (fold enrichment over control sample) was used as a cutoff for further analysis. Known contaminants were excluded, including human keratin and proteins introduced during the sample purification and preparation process (such as streptavidin, Benzonase, and trypsin), as well as naturally biotinylated proteins that contaminate the preparation by binding to streptavidin beads.

RAP-MS Experiments and Controls

The RAP-MS approach was validated by defining the proteins that interact with two well-characterized non-coding RNAs: (i) U small nuclear RNA, a core component of the spliceosome1 and (ii) 18S ribosomal RNA, a component of the small ribosomal subunit2. In the U1 purifications, 9 enriched proteins were identified, all of which are known to interact with the U1 snRNA. The list includes 7 of the 10 proteins that comprise the core U1 snRNP complex (U1-A, U1-C, U1-70K, Sm-B, Sm-D2, Sm-D3, Sm-E)3 as well as the Gemin5 processing factor involved in U1 snRNP biogenesis4 (FIGS. 10A-10C). The ninth enriched protein, SF3a1, had not previously been identified as a U1-interacting protein but was recently shown to interact directly with the U1 snRNA in vivo.

18S rRNA Versus U1 snRNA.

To validate the RAP-MS method and identify proteins specifically interacting with 18S ribosomal RNA or U1 snRNA, captures of each target RNA were performed in parallel samples from heavy and light labeled lysates from wild-type V6.5 ES cells. The total protein quantity in elution samples from each RAP-MS capture was measured by comparing the median intensity of peptides identified in a single quantitation MS run for each sample. The heavy and light label swapped samples were then mixed equally based on total protein quantity and analyzed by mass spectrometry to identify the SILAC enrichment ratio of proteins originating from 18S rRNA or U1 snRNA captures. The experiment was performed twice and each experimental set contained two biological replicates of 18S and U1 captures (heavy and light labeling states).

Xist lncRNA Versus U1 snRNA Captures.

To identify proteins specifically interacting with Xist lncRNA, captures were performed as described above with either 200M cells or 800M pSM33 cells treated with doxycycline for 6 hours. The total protein quantity in elution samples from each RAP-MS capture was measured by a single quantitation MS run for each sample. Heavy and light label swapped samples were mixed equally based on total protein quantity, and analyzed by mass spectrometry. SILAC ratios of Xist enriched proteins versus U1 enriched proteins were calculated and used to identify Xist-specific interacting proteins for further analysis. The experiment was performed twice and each experimental set contained two biological replicates of Xist and U1 captures, from heavy and light labeled samples. Proteins replicated well between samples, with a sole exception (LBR) that was missed only because its enrichment level (2-fold) fell below our enrichment cutoff (3-fold) in some replicate samples.

Validation of the Xist Interacting Proteins Identified by RAP-MS.

To confirm that the identified proteins reflect specific interactions with Xist, and are not due to background proteins or non-specific purification of other RNAs, RAP was performed using the same Xist probes in uninduced cells in which Xist is not expressed. Furthermore, to confirm that the identified interactions represent proteins that are crosslinked to Xist in vivo rather than interactions that form in solution, Xist was purified from cells that were not crosslinked (no UV light). In both cases, none of these 10 Xist-interacting proteins were identified, nor any other specifically enriched proteins in either of these control samples. Together, these results demonstrate that the identified proteins are direct RNA binding proteins that are covalently crosslinked with Xist in cells.

To confirm that these proteins do not merely associate non-specifically with any nuclear long ncRNA, Xist was compared to the 45S pre-ribosomal RNA, which is of comparable length to Xist (~13,000 vs. ~17,000 nucleotides, respectively) (FIG. 10A-10C). Notably, each of the 10 proteins that were enriched when comparing Xist to U1 was still enriched when comparing Xist to 45S. In three cases (hnRNPC, RALY, and LBR) the enrichment level was only ~2-fold because these proteins had higher levels in the 45S purification, consistent with the fact that they are known to be present in the nucleolus6. These results demonstrate that these 10 proteins associate with Xist specifically and not merely with any long RNA in the nucleus.

Figure 19:
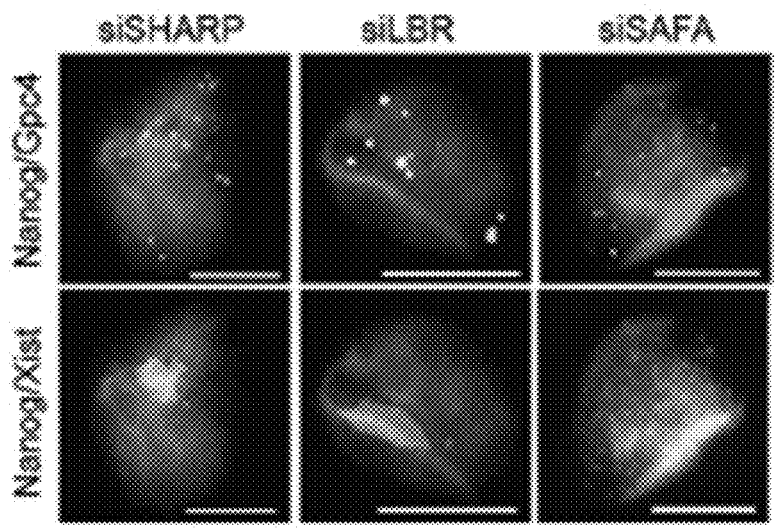
FIG. 19 shows representative images of staining of Nanog (cyan), Xist (red), and Gpc4 (green) upon knockdown of SHARP, LBR or SAF-A in ES cells after 16 hours of Xist induction with doxycycline with scale bars on the images represent 5 μm, according to embodiments of the present invention.

Since previous studies have shown that Xist can no longer initiate transcriptional silencing after a certain critical window during differentiation, it was confirmed that the loss of Xist silencing upon knock down of SHARP, LBR, and SAF-A was not merely due to cellular differentiation. To address this, single molecule FISH for Gpc4 mRNA was performed along with immunofluorescence for Nanog, a marker of the pluripotent state that is rapidly lost upon differentiation. It was confirmed that the knockdown of SHARP, LBR, or SAF-A also abolished gene silencing on the X-chromosome in Nanog-positive cells (FIG. 19).

Finally, these interactions were validated independently by testing whether the Xist RNA could be enriched upon immunoprecipitation of the identified proteins. To do this, high-quality IP-grade antibodies or epitope-tagged proteins were obtained for 8 of the 10 proteins (Ptbp1, hnRNPC, CELF1, Myef2, Rbm15, LBR, RALY, and SHARP) and purified protein-RNA complexes from UV-crosslinked lysate (Methods). In all cases, a strong enrichment for the Xist RNA relative to total input RNA levels (>4-fold, FIGS. 12A-12D) was observed. In contrast, a similar enrichment for other control RNAs—including mRNAs (i.e. Oct4, Nanog, or Stat3) or lncRNAs (i.e. Neat1, Malat1, Tug1, or Firre) (FIGS. 12A-12D) was not observed. For the remaining 2 proteins, it was not possible to identify antibodies or generate affinity reagents that could be used to independently validate their interactions. In one case (SAF-A), the protein has been previously shown to directly interact with Xist in human cells as described in You et al., 2013, *Nature Struct. Mol. Biol.*, 20:182-187, the entire content of which is herein incorporated by reference—providing independent confirmation.

Xist lncRNA Capture from Non-Crosslinked Cells.

As a control to ensure that purified proteins are not non-specifically associated or binding in vitro with target RNAs during capture, RAP-MS captures of Xist were performed from non-crosslinked cells otherwise treated in the same manner (i.e. doxycycline treated for 6 hours).

Xist lncRNA Capture from Cells where Xist is not Expressed.

To confirm that the identified proteins are not resulting from background proteins or probe association with other RNAs or proteins in the pSM33 cells, RAP captures of Xist from pSM33 cells were performed that were not treated with doxycycline, but which were otherwise treated identically.

45S Pre-rRNA Capture Versus U1 Capture.

To ensure that the proteins enriched in Xist captures using RAP-MS are not simply due to increased protein capture as a consequence of long target RNA transcripts, additional captures were performed of the 13,000 nucleotide long 45S pre-ribosomal RNA as a control. To ensure specific capture only of the 45S, and not the mature 18S and 28S, probes were designed that specifically targeted the internal transcribed spacer regions (ITS1 and ITS2) that are only present in the 45S pre-ribosomal RNA. The experiment was performed in the same manner and with the same conditions as the Xist lncRNA captures described above. To compare Xist protein enrichment to 45S protein enrichment, a SILAC approach was used based on direct comparison of two samples that share a common denominator (called spike-in SILAC37). Specifically, an overall Xist/45S SILAC ratio as calculated by multiplying the Xist/U1 ratio by the U1/45S ratio for each identified protein.

Protein Domain Classification.

The conserved domain structures of proteins were defined using the Protein Families database (Pfam38).

RNA Immunoprecipitation in UV-Crosslinked Cells.

pSM33 cells were cross-linked after 6 hours of doxycycline-treatment with 0.4 Joules/cm2 of UV254. Cells were lysed and RNA was digested with RNase I to achieve a size range of 100-500 nucleotides in length. Lysate preparations were precleared by mixing with Protein G beads for 1 hour at 4° C. For each sample, target proteins were immunoprecipitated from 20 million cells with 10 µg of antibody (Table 1) and 60 µl of Protein G magnetic beads (Invitrogen). The antibodies were pre-coupled to the beads for 1 hour at room temperature with mixing before incubating the precleared lysate to the antibody-bead complexes for 2 hours at 4° C. After the immunoprecipitation, the beads were rinsed with a wash buffer of 1×PBS with detergents. After a dephosphorylation treatment, the RNA in each sample was ligated to a mixture of barcoded adapters in which each adapter had a unique barcode identifier. After ligation, beads were rinsed with 1×PBS and detergents and then 5×PBS (750 mM NaCl) and detergents prior to pooling 3-4 antibodies in a new tube. The proteins and RNA were then eluted from the Protein G beads with 6 M urea and 40 mM DTT at 60° C. Protein-RNA complexes were separated away from free RNA by covalently coupling proteins to NHS-magnetic beads (Pierce) and washing 3 times in 6 M GuSCN (Qiagen RLT buffer) and heating in 1% NLS at 98° C. for 10 minutes. The proteins were then digested with Proteinase K and RNA was purified for subsequent analysis. From the barcoded RNA in each pool, Illumina sequencing libraries were generated as previously described in Kuo et al., 1998, *Bioessays*, 20:615-626, the entire content of which in herein incorporated by reference. A small percentage (~1%) was saved of starting material prior to immunoprecipitation and processed and sequenced this sample in parallel.

Analysis of Crosslinked RNA Immunoprecipitation Data.

The enrichment was computed for any RNA upon immunoprecipitation with a specific protein relative to its total levels in the cell. To do this, the total number of reads overlapping the RNA was counted in either the immunoprecipitation sample or the input control. To account for differences in read coverage between samples, each of these numbers was normalized to the total number of reads within the same experiment. This generates a normalized score, per RNA, within each sample. An enrichment metric was then computed by taking the ratio of these normalized values (IP/Input). These enrichment levels were then compared across different proteins and controls (i.e. IgG). To enable direct comparison across proteins for a given gene, it was necessary to account for differences in the protein specific background level, which may occur to differences in IP efficiency or non-specific binding of each antibody. To do this, a normalized enrichment ratio was computed by dividing the ratio for each gene by the average ratio across all genes for a given protein, as previously described 1.

To exclude the possibility of promiscuous binding to all RNAs, various mRNA controls were considered which are not expected to bind to these proteins, including Oct4, Nanog, Stat3, and Suz12. These mRNAs were selected as examples because they are expressed in ES cells, although many mRNAs show similar results. To account for the possibility that the Xist RNA non-specifically binds to any RBP, Xist with other RBPs that were not identified as interacting with Xist by RAP-MS (Pum1 and hnRNP-H) were evaluated. To ensure that a negative result (i.e. no enrichment for Xist) is meaningful and does not reflect a failed immunoprecipitation experiment, Neat1-1 was evaluated, which it was previously found immunoprecipitates with hnRNPH1. To further evaluate the level of enrichment on other lncRNAs, several lncRNAs were evaluated including Malat1, Firre, and Tug1. These lncRNAs were selected as examples because they are well-known and expressed in ES cells, although many ES lncRNAs show similar results.

Immunoprecipitation and RT-qPCR

Female ES cells were differentiated then crosslinked with UV4k as described above. Pellets of 20M cells were lysed and treated with TURBO DNase (Ambion) to destroy DNA by incubation for 10 minutes at 37° C. in an Eppendorf Thermomixer C. The lysate was pre-cleared by incubation with 180 µL of Dynabeads Protein G magnetic beads (Life Technologies). Meanwhile, 10 µg of antibody for immunoprecipitation (SHARP antibody, Novus NBP1-82952 or IgG antibody, Cell Signaling 2729S) was coupled to 60 µl Protein G magnetic beads. After pre-clearing was completed, the lysate was then mixed with the appropriate antibody-coupled Protein G magnetic beads and incubated for 2 hours at 4° C. on a Hulamixer sample mixer (Life Technologies) for protein capture. After immunoprecipitation, beads were washed with a wash buffer of 1×PBS with detergents and then captured nucleic acids were eluted by digesting all proteins with 5.6 U proteinase K (New England Biolabs). Eluted RNA was purified using the RNA Clean and Concentrator-5 Kit (Zima Research) and RT-qPCR was performed as described previously 13 to evaluate RNA enrichment.

V5-Epitope Tagged Protein Expression.

For V5-tagged protein expression and immunoprecipitation, mouse ES cells were electroporated using the Neon transfection system (Invitrogen) with an episomally-replicating vector (pCAG-GW-V5-Hygro) encoding expression of a C-terminal V5 tagged ORF driven by a CAG promoter. ORFs were obtained from the DNASU plasmid repository as Gateway entry clones and inserted into pCAG-GW-V5-Hygro using an LR recombination reaction (Invitrogen). Transfected cells were selected on 125 ug/mL Hygromycin B (Invitrogen) to generate stably expressing lines.

siRNA Transfections.

For siRNA knockdown experiments, 20 nM siRNAs were transfected using the Neon transfection system (settings: 1200V, 40 ms width, 1 pulse). For each transfection, two 10 µL transfections with the same siRNA were carried out in succession using 100,000 cells each, mixed, and plated equally between two poly-L-lysine or poly-D-lysine (Sigma) and 0.2% gelatin (Sigma)-coated #1.5 coverslips placed into wells of a 24-well plate containing 2i media.

After 48 hours, 2i media was replaced and cells on one coverslip of each pair were treated with 2 g/mL doxycycline (Sigma) for 16 hr to induce Xist expression. Coverslips were then fixed in Histochoice (Sigma) for 5 min, washed thoroughly in PBS, and dehydrated in ethanol for storage until FISH staining.

For all proteins siRNAs pool from Dharmacon (ON-TARGETplus SMARTpool siRNAs) was used. For each of these, it was tested whether the siRNA successfully reduced the targeted mRNA expression by >70%. For SAF-A and SMRT, the siRNAs failed to achieve this level of mRNA reduction, so additional siRNAs were purchased (and their associated controls) for SAF-A and SMRT from Qiagen and Ambion respectively, and selected siRNAs that successfully reduced on-target mRNA levels. siRNA against GFP was purchased from Qiagen. For additional independent siRNAs, the siRNAs were purchased as a pool from Dharmacon, Qiagen, and Ambion, or as each individual siRNA deconvoluted from the pool from Dharmacon and Qiagen as shown in Table 2.

TABLE 2

A list of all SiRNAs used for knockdown experiments.

| Description | Company | Catalog number |
|---|---|---|
| SMARTpool: ON-TARGETplus Hnrnpc siRNA | Dharmacon | L-044147-01-0005 |
| SMARTpool: ON-TARGETplus Ncor2 siRNA | Dharmacon | L-044147-01-0005 |
| SMARTpool: ON-TARGETplus Hdac3 siRNA | Dharmacon | L-043553-02-0005 |
| SMARTpool: ON-TARGETplus Spen siRNA | Dharmacon | L-062019-01-0005 |
| SMARTpool: ON-TARGETplus Rbm15 siRNA | Dharmacon | L-048728-01-0005 |
| SMARTpool: ON-TARGETplus Lbr siRNA | Dharmacon | L-051330-01-0005 |
| SMARTpool: ON-TARGETplus Ptbp1 siRNA | Dharmacon | L-042865-01-0005 |
| SMARTpool: ON-TARGETplus Hnrnpu siRNA | Dharmacon | L-051574-01-0005 |
| SMARTpool: ON-TARGETplus Myef2 siRNA | Dharmacon | L-058553-01-0005 |
| SMARTpool: ON-TARGETplus YY1 siRNA | Dharmacon | L-050273-00-0005 |
| SMARTpool: ON-TARGETplus Celf1 siRNA | Dharmacon | L-064577-01-0005 |
| SMARTpool: ON-TARGETplus Raly siRNA | Dharmacon | L-044852-02-0005 |
| SMARTpool: ON-TARGETplus Hnrnpm siRNA | Dharmacon | L-044465-01-0005 |
| SMARTpool: ON-TARGETplus Atrx siRNA | Dharmacon | L-046292-01-0005 |
| SMARTpool: ON-TARGETplus Satb1 siRNA | Dharmacon | L-045547-01-0005 |
| SMARTpool: ON-TARGETplus Eed siRNA | Dharmacon | L-049898-00-0005 |
| SMARTpool: ON-TARGETplus Srsf1 siRNA | Dharmacon | L-040886-01-0005 |
| ON-TARGETplus Non-targeting Pool | Dharmacon | D-001810-10-05 |
| Silencer Select Pre-Designed siRNA: Ncor2 | Ambion/Life Technologies | Assay ID s74030 |
| Silencer Select Pre-Designed siRNA: Spen | Ambion/Life Technologies | Assay Id s80456 |
| FlexiTube GeneSolution GS56381 for Spen | Qiagen | GS56381 |
| FlexiTube GeneSolution GS98386 for Lbr | Qiagen | GS98386 |
| FlexiTube GeneSolution GS51810 for Hnrnpu | Qiagen | GS51810 |
| FlexiTube GeneSolution GS20602 for Ncor2 | Qiagen | GS20602 |
| GFP siRNA (1 nmol) | Qiagen | SI04380467 |

Individual siRNA Deconvoluted from the Pool

| Description | Company | Catalog number |
|---|---|---|
| SMARTpool: ON-TARGETplus Spen siRNA Upgrade | Dharmacon | LU-062019-01-0002 |
| D1: CGAGAGGGAGAGACGAAUA SEQ ID NO: 1 | | |
| D2: CUAAAGAGCCGGAGCCGAA SEQ ID NO: 2 | | |
| D3: CCUAAAAUCACGUCGGUUA SEQ ID NO: 3 | | |
| D4: GGAAACACCUCAAGGCCGA SEQ ID NO: 4 | | |
| SMARTpool: ON-TARGETplus Lbr siRNA Upgrade | Dharmacon | LU-051330-01-0002 |
| D1: UGUUGAAGCCGUUCGGAAA SEQ ID NO: 5 | | |
| D2: AUACAAAGAUGGCACCGAA SEQ ID NO: 6 | | |
| D3: AUAAACACAUAGACGACUU SEQ ID NO: 7 | | |

In addition to the proteins identified by RAP-MS, several proteins were knocked down to associate with Xist—including EED (a component of PRC2), YY139, Satb140, SRSF141, hnRNPC42, and Atrx43.

siRNA Experiments in Female ES Cells.

Female ES F1 2-1 cells were similarly transfected. To initiate differentiation and Xist expression for these cells, 2i was replaced with MEF media (DMEM, 10% Gemini Benchmark FBS, 1×L-glutamine, 1×NEAA, 1× Pen/Strep; Life Technologies unless otherwise indicated) at 12 hours post-transfection. Forty-eight hours after transfection, 1 uM retinoic acid (Sigma) was administered for 24 hours and cells were fixed as described above. For cells not undergoing differentiation, 2i was replaced 12 hr and 48 hr after transfection.

Single Molecule RNA FISH.

Single molecule RNA Fluorescence in situ hybridization (FISH) experiments were done using QuantiGene ViewRNA ISH Cell Assay (Affymetrix) and QuantiGene ViewRNA ISH Cell 740 Module (Affymetrix) according to manufacturer's protocol. Cells fixed on coverslips were first permeabilized with Detergent Solution QC at room temperature for 5 min, and then incubated with desired mixture of probe set (Affymetrix) in Probe Set Diluent QF at 40° C. for 3 h, followed by incubated with PreAmplifier Mix at 40° C. for 30 min, Amplifier Mix at 40° C. for 30 min, and Label Probe Mix at 40° C. for 30 min sequentially. For DAPI staining, coverslips were incubated in 30 nM DAPI in PBS at room temperature for 15-20 min. Probe set and conjugated fluorophore for FISH were TYPE 1-XIST (550 nm), TYPE 4-GPC4, RBMX, SMC1A, MECP2 (488 nm), TYPE 10-ATRX (740 nm), and TYPE 6-EED1, SHARP, LBR, SAFA, RBM15, MYEF2, PTBP1, HNRNPC, HNRNPM, CELF1, RALY, HDAC3, NCOR2, MIDI, PIR (650 nm).

Immunofluorescence and RNA FISH.

For immunofluorescence (IF), cells were fixed on coverslips and permeabilized with 0.1% Triton-X in PBS at room temperature for 10 min, and blocked with 5% normal goat serum in PBS at room temperature for 10 min. Cells were then incubated with primary antibodies at room temperature for 1 h, followed by incubating with secondary antibodies at room temperature for 1 h. The samples were then processed using the RNA FISH protocol, as described above. Primary antibodies and the dilution used for IF were anti-RNA polymerase II CTD repeat YSPTSPS (phospho S2) (Abcam; ab5095) (1:100), anti-Nanog (Abcam; ab80892) (1:100), and anti-EZH2 (Active Motif; 39933) (1:100). Secondary antibodies and the dilution used for IF were Alexa Fluor® 405 goat anti-rabbit IgG (H+L) (Life Technology; 1575534) (1:100) and Alexa Fluor® 488 F(ab')2 fragment of goat anti-rabbit IgG (H+L) (Life Technology; 1618692) (1:100).

Microscopic Imaging.

FISH and IF/FISH samples were imaged using a Leica DMI 6000 Deconvolution Microscope with the Leica HC PL APO 63×/1.30 GLYC CORR CS2 objective. Samples stained with TYPE 10-ATRX (740 nm) were imaged using Nikon Ti Eclipse with the Nikon CFI Plan Apochromat λ DM 60×/1.40 oil objective. Images were projected with maximum projection (3 µm; step size, 0.5 µm).

X-chromosome Silencing Assay.

Cells were stained for Xist RNA, Gpc4 mRNA, Atrx mRNA and siRNA-targeted mRNA by FISH and imaged. In addition, in some siScramble and siSHARP samples, probes against Rbm1S5, Mecp2, Smc1a, Mid1 or Pir mRNA were used. Images were then analyzed using Matlab R2013b (described below). Cells were selected if the copy number of the targeted mRNA was less than 30% of the level of the no siRNA treated cells and if they induced Xist expression. Within these cells, the copy number of Gpc4 mRNA and Atrx mRNA were quantified using a peak finding method (described below) and compared across conditions. mRNA levels were quantified for 50 individual cells. Xist expression was also evaluated in siRNA-treated cells, and no difference was observed in the percentage of cells that induced Xist expression in any of the siRNA conditions relative to untreated cells.

Quantifying mRNAs by Single Molecule FISH.

All image analysis was carried out using Matlab (version R2013b) utilizing built-in functions from the Image Processing toolbox. Images were first filtered using a two-dimensional median filter to remove background. Cell boundaries were outlined manually, guided by DAPI staining, to create a binary mask and applied to the various channels from the same field of view. Top-hat morphological filtering, a background subtraction method that enhances the individual focal spots, was applied to the images as described in Theodosiou et al., 2007, *Cytometry*, 71:439-450, the entire content of which is herein incorporated by reference. The spots were then identified using a 2D peak finding algorithm that identifies local maximal signals within the cell. Once regional maxima were identified, the number of spots was counted for each cell.

Ezh2 Recruitment and PolII Exclusion.

Cells were stained for Xist RNA and the siRNA-targeted mRNA (FISH) along with Ezh2 or PolII (IF) as described above. For image acquisition, the exposure time for each individual channel was kept the same across all samples. Images were then analyzed and selected for XIST-induced and cells showing knock down of the target mRNA, as described above. Specifically, the nuclei of individual cells were identified manually using the DAPI staining. The Xist cloud was identified by using an intensity-based threshold to partition the image within the nucleus and find contiguous 2-dimensional regions of high intensity. The threshold was determined based on Otsu method as previously described 45, which splits the image into 2 bins—high and low—and identifies a threshold that minimizes the variance within the partition. This creates a binary mask on the image. It was visually confirmed that this binary mask accurately reflected the Xist cloud. This binary mask was then applied to all other images in that field of view (PolII or Ezh2) for all images. The intensity of fluorescence signal was then quantified by taking the average intensity of all the pixels within the region (i.e. PolII or Ezh2, respectively). This average intensity (1 number per cell) was computed across all conditions and compared them using a 2-same unpaired t-test relative to the scramble sample across 50 single cells.

Example 9

The Xist-LBR Interaction

One of the proteins identified in the Xist silencing complex is the Lamin B Receptor (LBR), a transmembrane protein that is anchored in the inner nuclear membrane, interacts with Lamin B, and is required for anchoring chromatin to the nuclear lamina—a nuclear compartment that helps shape the 3-dimensional structure of DNA and is enriched for silencing proteins. Based on these observations, along with the observation that induction of XCI leads to recruitment of the inactive X-chromosome to the nuclear lamina, it was hypothesized that the Xist-LBR interaction might be important both for shaping nuclear organization and regulating gene expression during XCI.

Figure 20A:
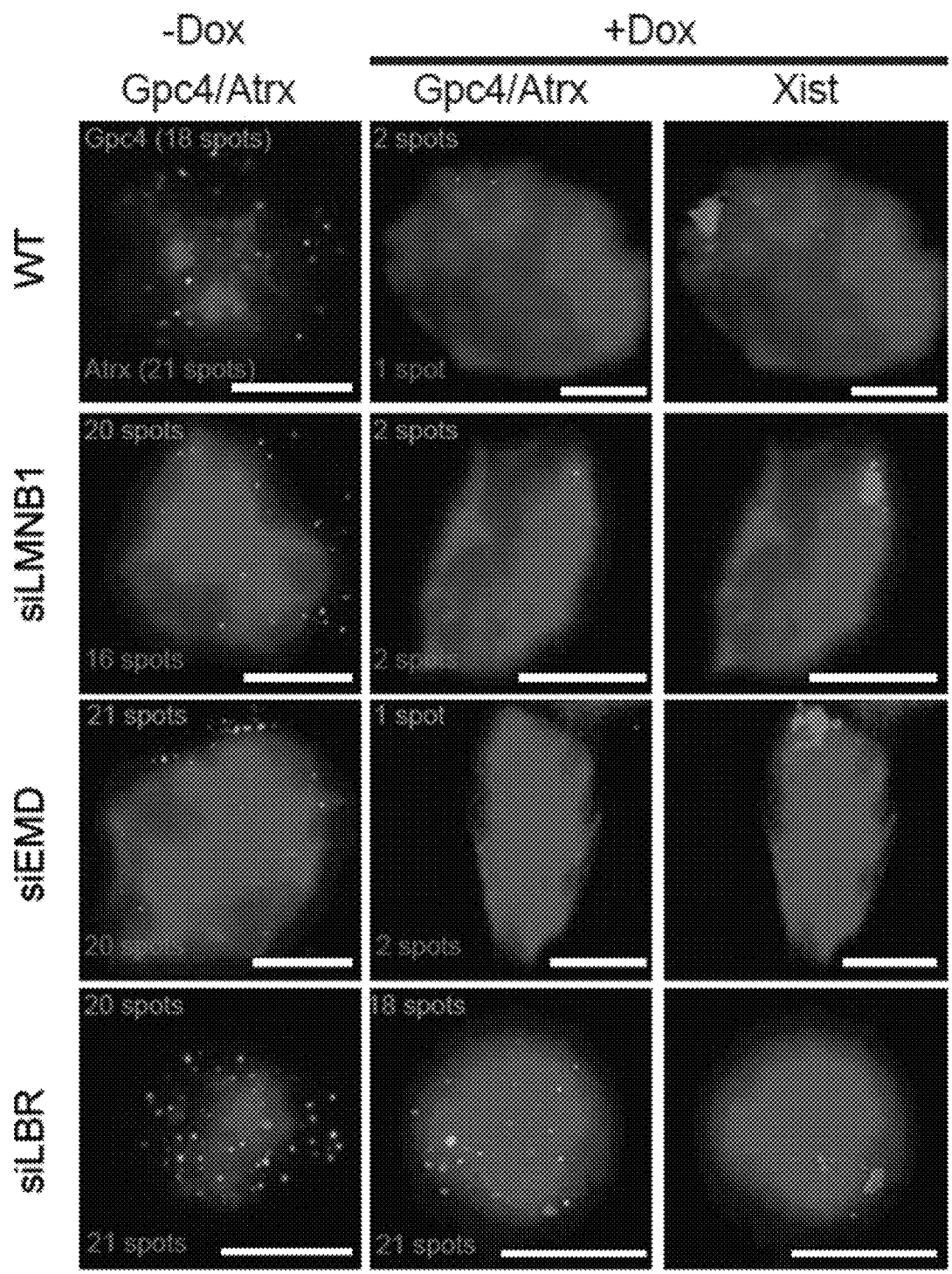
FIG. 20A shows representative mages of individual cells showing two X-linked mRNAs, Gpc4 (green) and Atrx (red) along with Xist (red) and DAPI (blue) after treatment with different siRNAs (rows), the number of identified mRNAs is shown, with scale bars: 5 micrometers, according to embodiments of the present invention.
Figure 20B:
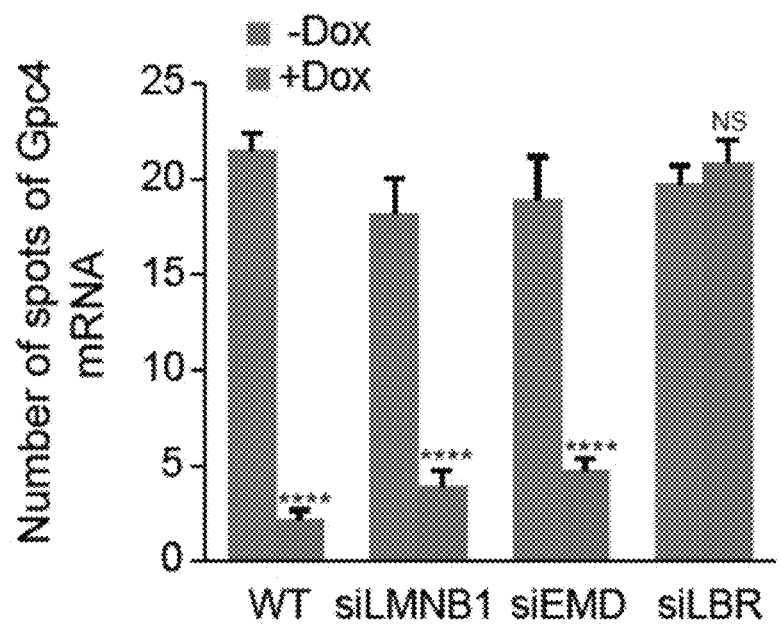
FIGS. 20B-20C are graphs plotting the quantification of the copy number of Gpc4 (FIG. 20B) and Atrx (FIG. 20C) mRNA before Xist induction (−Dox) and after Xist induction (+Dox) after treatment with different siRNAs. Error bars represent the SEM across 50 individual cells, NS: not significant, **** p-value<0.001 relative to −Dox cells by an unpaired two-sample t-test, according to embodiments of the present invention.
Figure 20C:
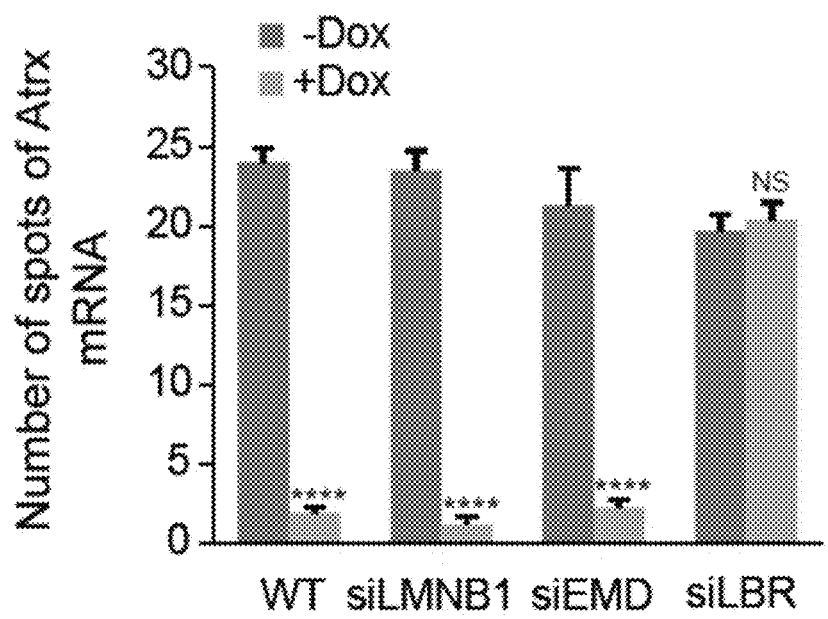

To test this, LBR expression was knocked down and the expression of two X chromosome genes, Atrx and Gpc4, was measured before and after Xist induction using single molecule RNA FISH. Knockdown of LBR led to a defect in Xist-mediated silencing of these X chromosome genes (FIG. 4), with cells demonstrating comparable expression before and after Xist induction (FIGS. 20A, 20B, 20C). To ensure that the observed silencing defect is not merely caused by disruption of the nuclear lamina, Lamin B1 or Emerin, two additional components of the nuclear lamina, were knocked down and no defect was observed in Xist-mediated silencing (FIG. 4, FIGS. 20A, 20B, 20C).

Example 10

The Role of LBR-Mediated Silencing

Figure 21A:
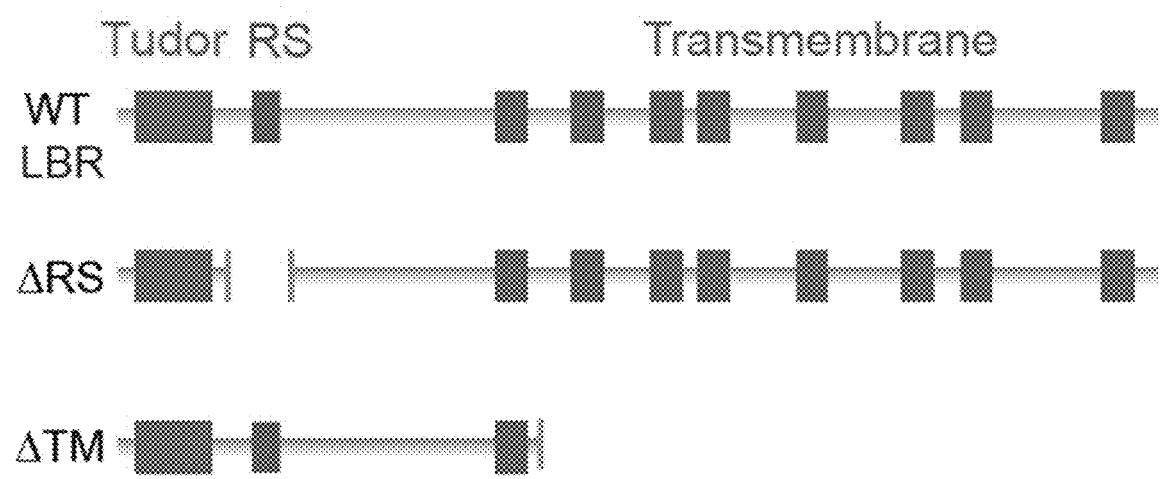
FIG. 21A is a schematic of the domain structure of the LBR protein showing the regions deleted in ΔRS-LBR (amino acids 71-90) and ΔTM-LBR (amino acids 237-615), according to embodiments of the present invention.
Figure 21D:
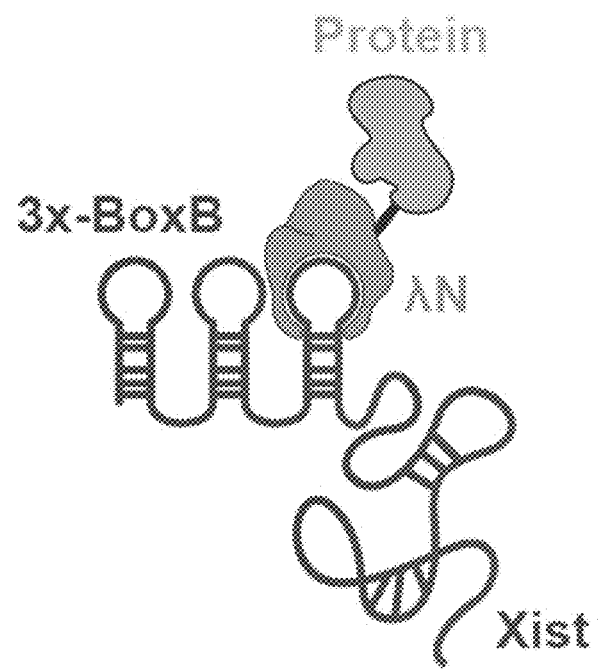
FIG. 21D is a schematic of the interaction between λN-fusion protein and Xist containing 3×-BoxB, according to embodiments of the present invention.

To determine whether LBR-mediated silencing is due to its interaction with Xist, it was thought to disrupt its RNA binding region. However, among the Xist-interacting proteins identified by RAP-MS, LBR is the only protein that does not contain a canonical RNA binding domain. It was hypothesized that the Arginine-Serine (RS) motif of LBR might be required for interacting with Xist (FIG. 21) because this motif is known to be involved in RNA binding. To test this, a truncated LBR protein was generated containing a deletion of the RS motif (ΔRS-LBR, FIG. 21A). As a control, seven of the eight transmembrane domains in LBR (ΔTM-LBR, FIG. 21A) were deleted. Consistent with previous observations, it was found that both ΔRS-LBR and ΔTM-LBR localize properly in the nuclear envelope (FIG.

Figure 22A:
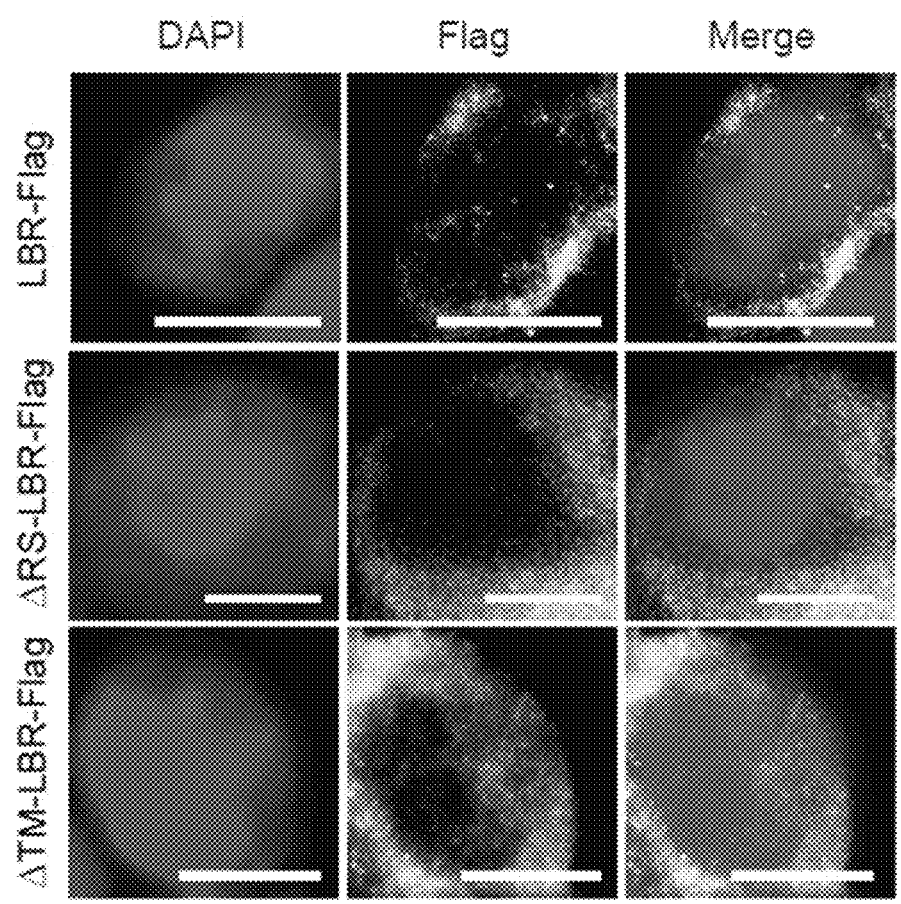
FIG. 22A shows representative images of individual cells for full-length LBR, ΔRS-LBR or ΔTM-LBR (yellow) along with DAPI (blue), with scale bars: 5 micrometers, according to embodiments of the present invention.
Figure 22B:
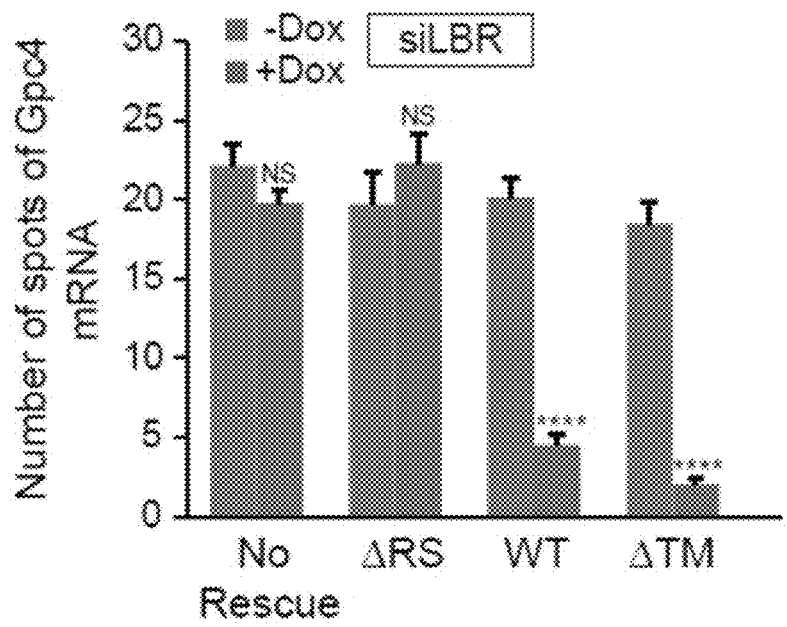
FIGS. 22B-22C are graphs plotting the quantification of the copy number of Gpc4 (FIG. 22B) and Atrx (FIG. 22C) mRNA for −Dox and +Dox cells expressing ΔRS-LBR or ΔTM-LBR upon LBR knock down with error bars representing the SEM across 50 individual cells, NS: not significant, **** p-value<0.001 relative to −Dox cells by an unpaired two-sample t-test, according to embodiments of the present invention.
Figure 22C:
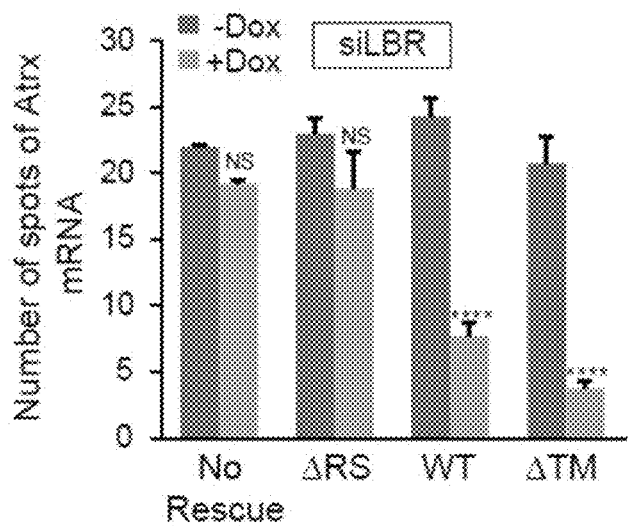

22A). Notably, ΔRS-LBR did not interact with Xist (~97% reduced binding, FIG. 21B), and failed to rescue the silencing defect upon knock down of LBR (FIG. 21C, FIGS. 22B-22C). In contrast, ΔTM-LBR did not impact Xist binding (FIG. 21B) and was able to rescue the silencing defect upon knock down of LBR (FIG. 21C, FIGS. 22B-22C).

Figure 21E:
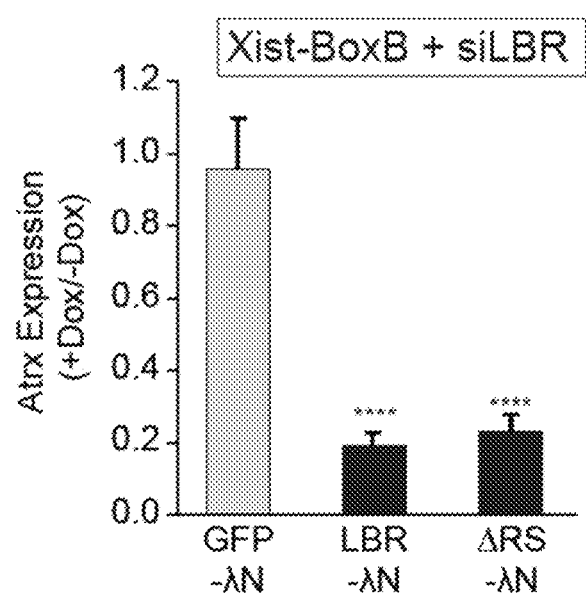
FIG. 21E is a graph plotting the relative Atrx mRNA expression in Xist-BoxB cells after siRNA knockdown of the endogenous LBR and expression of GFP-λN (control), LBR-λN, or ΔRS-LBR-N, according to embodiments of the present invention.
Figure 21F:
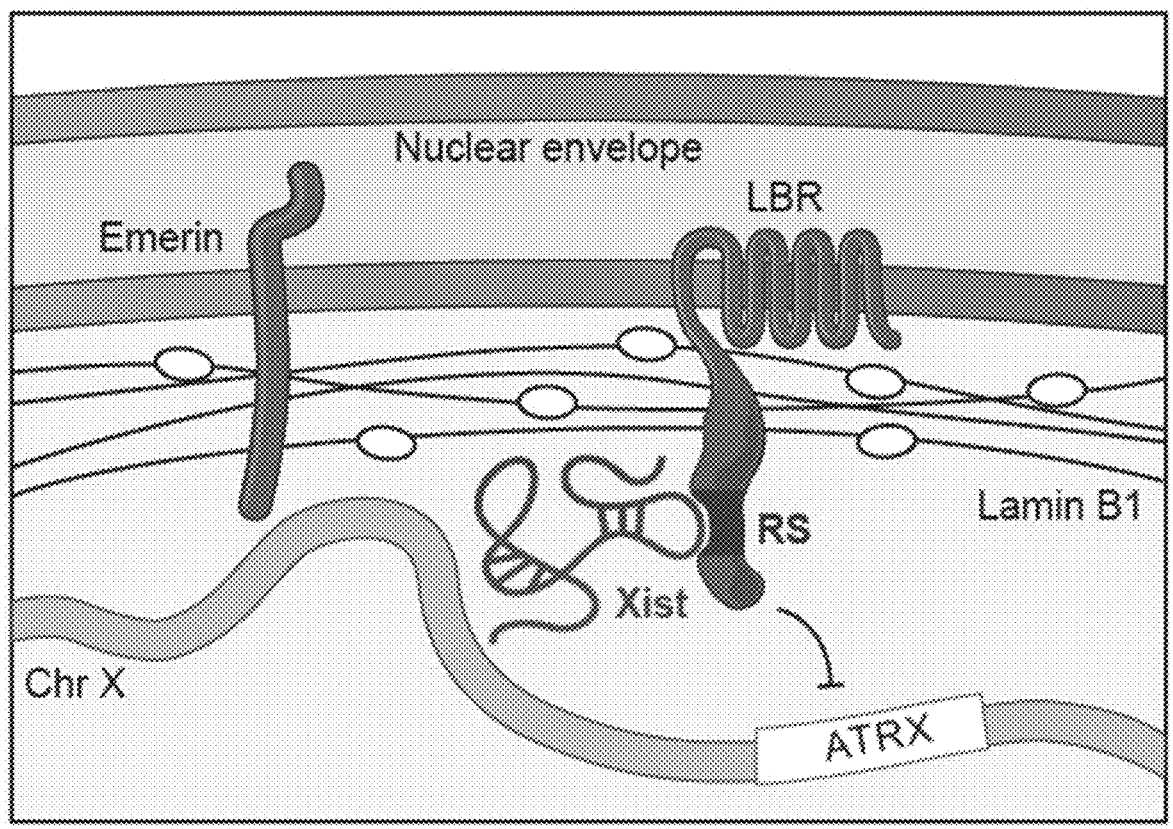
FIG. 21F is a schematic of the nuclear lamina and the interaction between LBR and Xist, according to embodiments of the present invention.
Figure 23B:
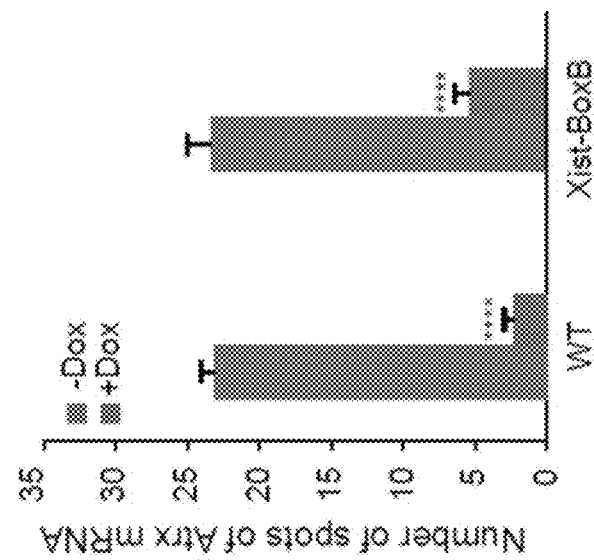
FIG. 23B is a graph plotting the quantification of the copy number of Atrx mRNA for −Dox and +Dox cells expressing Xist-BoxB with error bars representing the SEM across 50 individual cells, NS: not significant, **** p-value<0.001 relative to −Dox cells by an unpaired two-sample t-test, according to embodiments of the present invention.
Figure 23A:
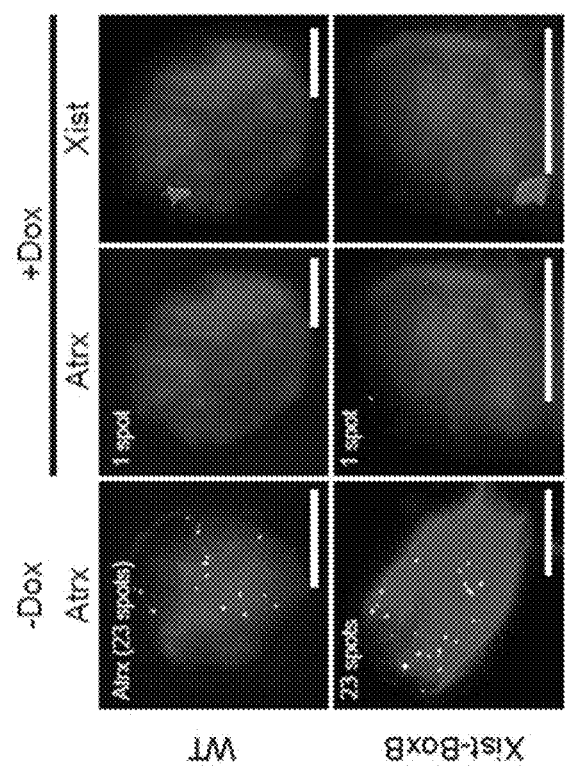
FIG. 23A shows representative images of individual cells for Atrx mRNA (yellow) along with Xist (red) and DAPI (blue) in cells expressing Xist fused with 3×-BoxB cells, with scale bars: 5 micrometers, according to embodiments of the present invention.

To ensure that ΔRS-LBR fails to silence X chromosome genes because of its RNA binding ability and specifically its interaction with Xist, it was tested whether artificially tethering ΔRS-LBR to the Xist RNA can re-establish Xist-mediated silencing. To do this, 3 copies were fused of the viral BoxB RNA aptamer, which binds tightly to the viral λN coat protein, to the 3' end of the endogenous Xist RNA (Xist-BoxB, FIG. 21D) and ensured that Xist-BoxB still silences X chromosome genes (FIGS. 23A-23B). Expression of ΔRS-LBR-λN in Xist-BoxB cells rescued the silencing defect observed upon LBR knock down (FIG. 21E). Together, these results demonstrate that the Xist-LBR interaction is required for Xist-mediated transcriptional silencing (FIG. 21F).

It was hypothesized that the RS-motif of LBR might be required for interacting with Xist because the RS motif is present within a class of mRNA binding proteins involved in splicing (SR proteins), is overrepresented in RNA binding proteins that lack canonical RNA binding domains, and the RS motif of LBR was previously shown to interact with RNA in vitro.

Example 11

Cross-Linking and Immunoprecipitation (CLIP) of LBR

Figure 24A:
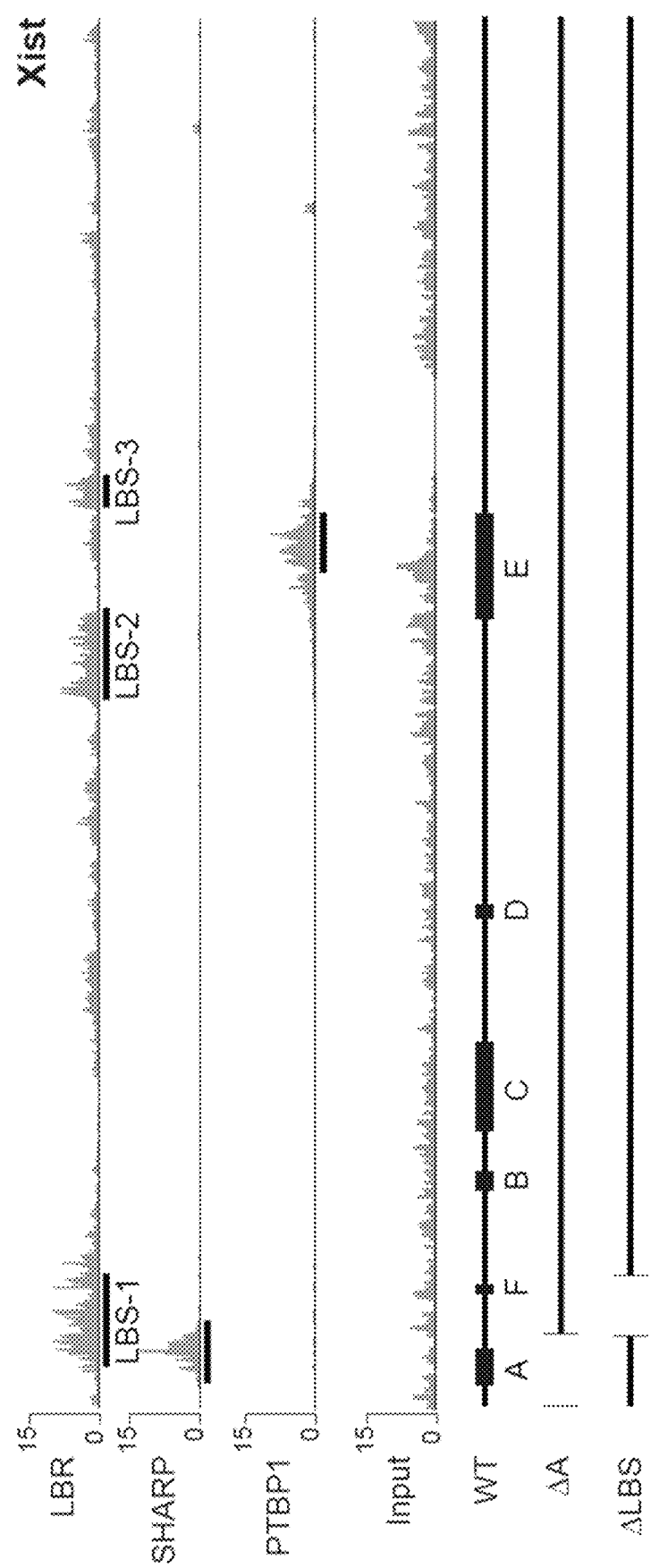
FIG. 24A shows CLIP data plotted across the Xist RNA for LBR, SHARP, and PTBP1 proteins, with the values representing fold-enrichment at each position on Xist normalized to a size-matched input RNA control, according to methods described herein, where Input represents the total RNA control for the LBR CLIP sample; Bottom: A schematic of the annotated repeat regions on the Xist RNA (WT) and the locations of the deleted regions in the ΔA (nucleotides 1-937) and ΔLBS (nucleotides 898-1682) Xist RNA, according to embodiments of the present invention.

To determine where LBR binds to Xist, RNA-protein complexes were UV crosslinked in cells, digested RNA into short fragments, immunoprecipitated LBR, gel extracted crosslinked RNA-protein complexes, and sequenced the Xist RNA. Three discrete LBR binding sites (LBS) were identified that are spread across >10,000 nucleotides of the Xist RNA (FIG. 24A). These LBR binding sites are distinct from the binding sites of other Xist interacting proteins, including SHARP and PTBP1 (FIG. 24A). Interestingly, one of these LBR binding sites (LBS-1) overlaps the ~900 nucleotide region of Xist that was previously shown to be required for Xist-mediated silencing (ΔA-repeat region) (20) (FIG. 24A).

Example 12

Binding Domains of LBR

Figure 25:
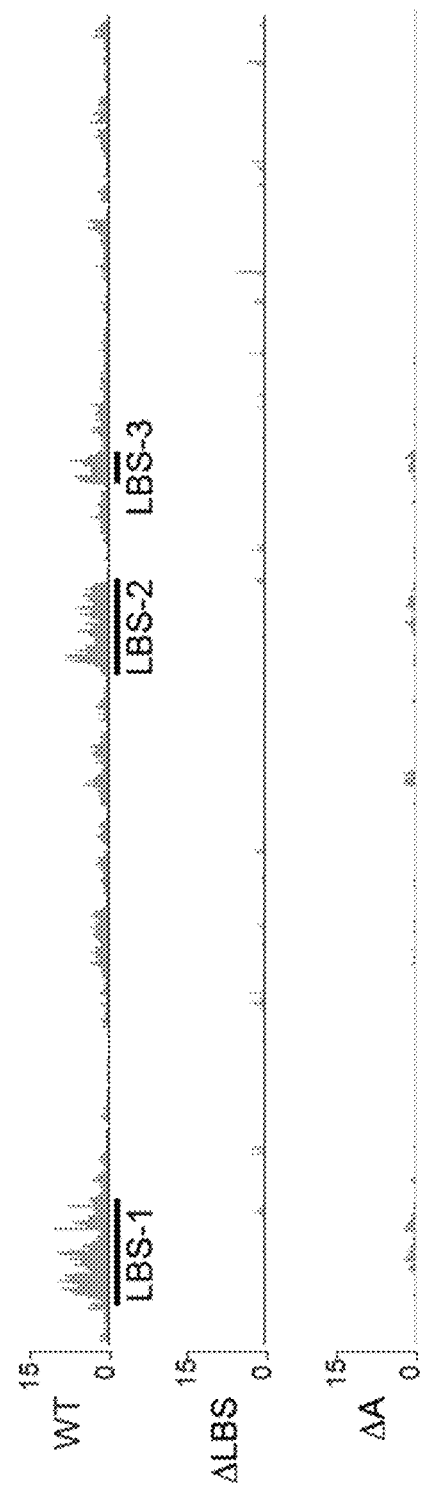
FIG. 25 shows CLIP result for LBR across the Xist RNA for wild type sample, ΔLBS, and ΔA cells, with the values representing the fold-enrichment of each sample at each position on Xist RNA normalized to the input RNA from each sample, according to embodiments of the present invention.
Figure 26A:
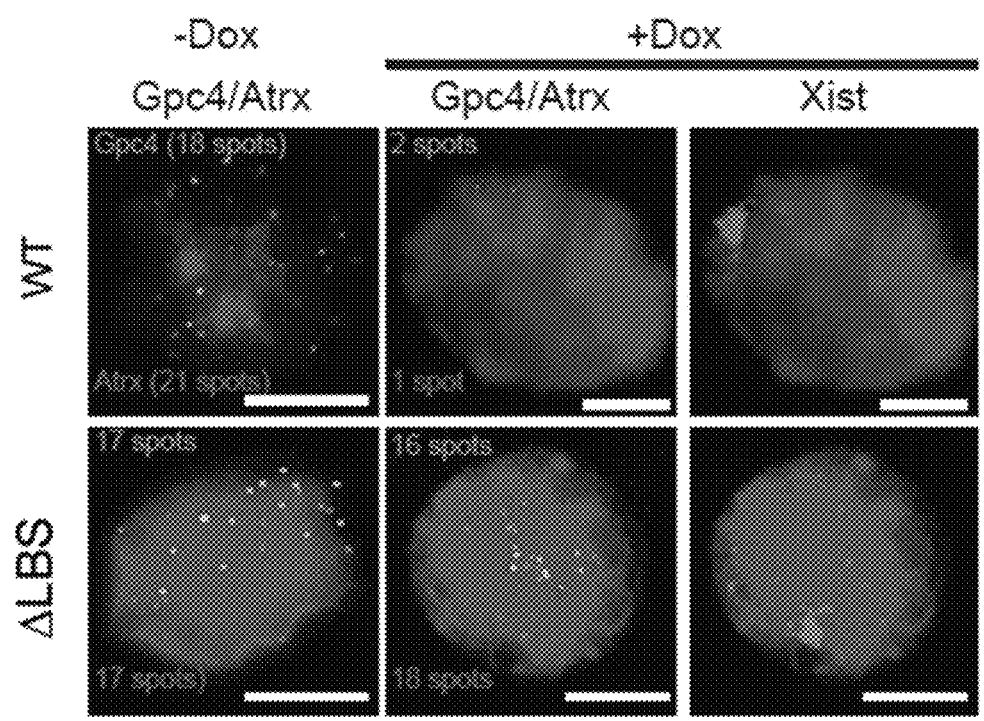
FIG. 26A shows representative images of individual cells for two X-linked mRNAs, Gpc4 (green) and Atrx (red) along with Xist (red) and DAPI (blue) in ΔLBS cells, with the number of identified mRNAs is shown, scale bars: 5 micrometers, according to embodiments of the present invention.
Figure 26B:
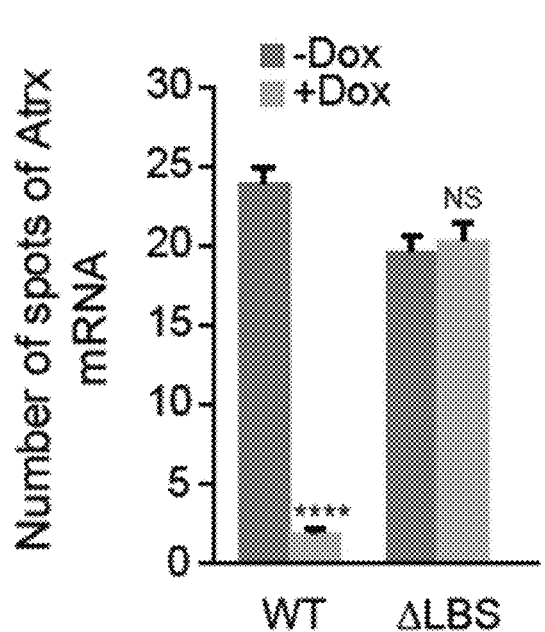
FIGS. 26B-26C are graphs plotting the quantification of the copy number of Gpc4 (FIG. 26B) and Atrx (FIG. 26C) mRNA for −Dox and +Dox cells expressing ΔLBS Xist, with error bars representing the SEM across 50 individual cells, NS: not significant, **** p-value<0.001 relative to −Dox cells by an unpaired two-sample t-test, according to embodiments of the present invention.
Figure 26C:
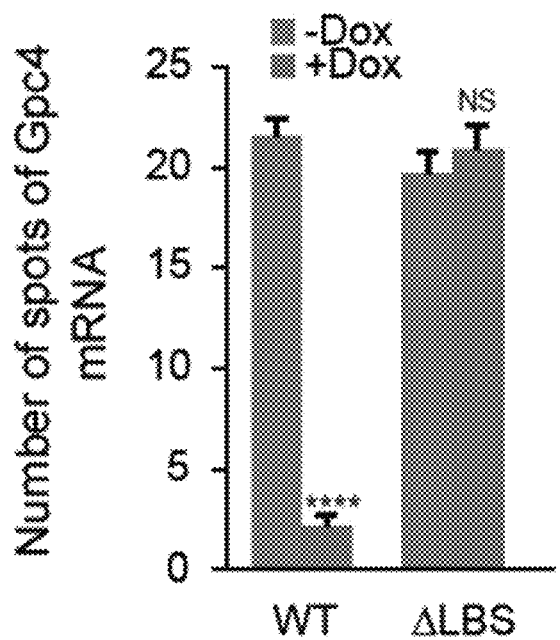

LBR binding as tested within a previously generated ΔA-repeat cell line (20) and found that LBR binding is disrupted across the entire Xist RNA (FIG. 24B), including the LBR binding sites that do not overlap the ΔA-repeat region (Supplemental FIG. 4). Because SHARP also binds within the ΔA-repeat region (FIG. 24A) and its binding is also disrupted in ΔA-Xist (FIG. 24B), a mutant Xist was generated that precisely deletes a region within the LBR binding site that is not within the SHARP binding site (ΔLBS, FIG. 24A). In ΔLBS-Xist, LBR binding was lost across the entire Xist RNA without impacting SHARP binding (FIG. 24B, FIG. 25). Notably, ΔLBS-Xist fails to silence X chromosome transcription to a similar level as observed in the ΔA-Xist (FIG. 24C, FIGS. 26A, 26B, 26C). The observation that deletion of a single LBR binding site leads to loss of LBR binding across Xist (FIG. 25) suggests that these sites might be involved in a long range structural interaction that is required for LBR binding.

Figure 27A:
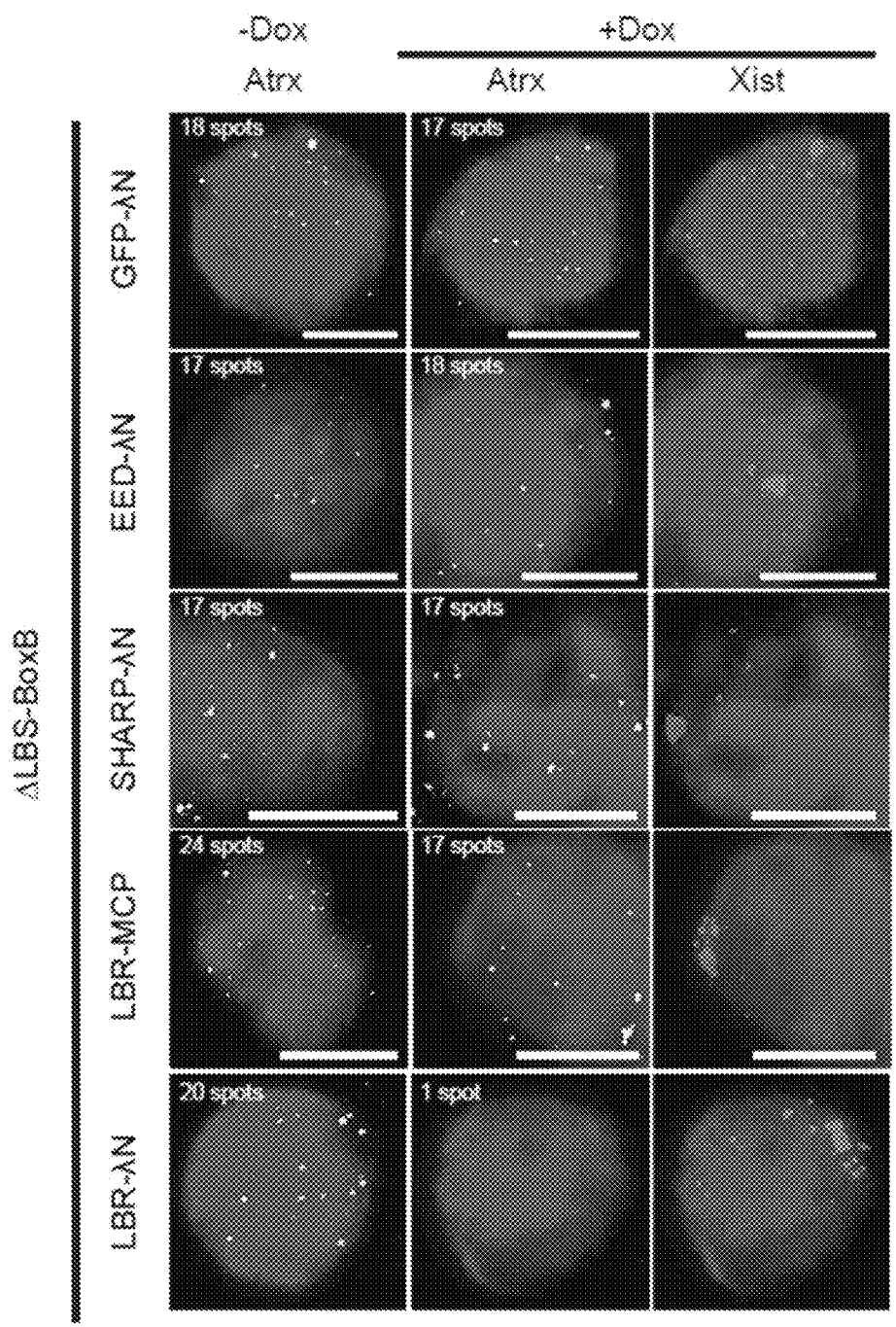
FIG. 27A shows representative images of individual cells for Atrx mRNA (yellow) and Xist (red) along with DAPI (blue) in cells expressing ΔLBS-BoxB Xist after transfecting with different fusion proteins, the number of identified mRNAs is shown, scale bars: 5 micrometers, according to embodiments of the present invention.
Figure 27B:
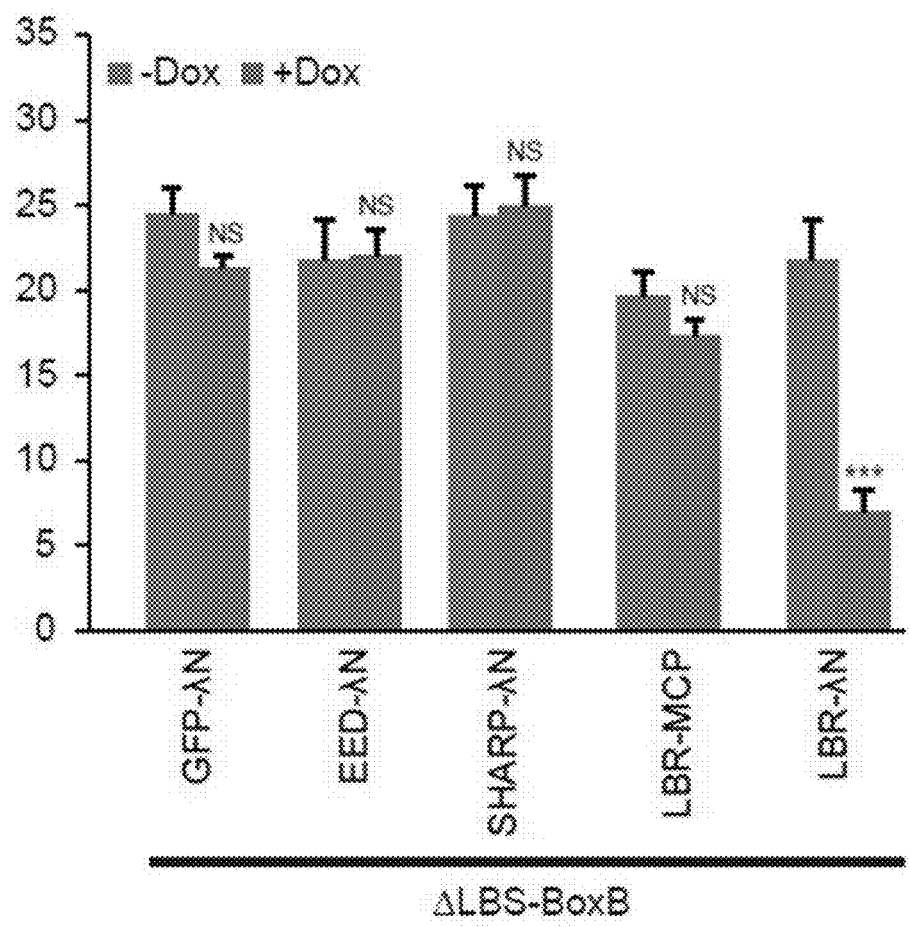
FIG. 27B is a graph plotting the quantification of the copy number of Atrx mRNA for −Dox and +Dox cells expressing ΔLBS-BoxB Xist after transfecting with different fusion proteins, with error bars representing the SEM across 50 individual cells, NS: not significant. *** p-value<0.005 relative to −Dox cells by an unpaired two-sample t-test, according to embodiments of the present invention.

To ensure that the observed silencing defect in ΔLBS-Xist cells is due to LBR binding alone and not due to disruption of another unknown protein interaction, it was tested whether the observed silencing defect could be rescued by re-establishing the ΔLBS-LBR interaction. To do this, an endogenous ΔLBS-BoxB Xist RNA was generated and it was confirmed that expression of LBR-λN fusion protein, but not LBR fused to a different RNA binding domain (MS2-coat protein), was able to rescue the silencing defect observed in ΔLBS-BoxB cells (FIG. 24D, FIGS. 27A-27B). In contrast, expression of other silencing proteins fused to λN, such as SHARP and EED, did not rescue the observed silencing defect (FIG. 24D, FIGS. 27A-27B). Together, these results demonstrate that the LBR binding site that overlaps the ΔA-repeat region of Xist is required for silencing.

Example 13

Recruitment of Inactive X Chromosome Through LBR

Figure 28A:
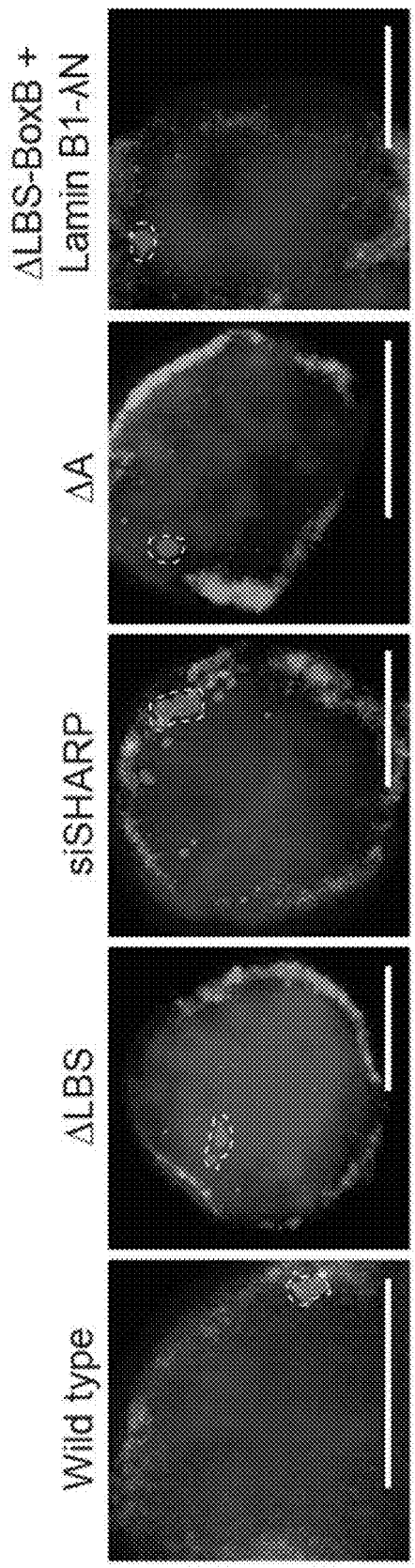
FIG. 28A shows representative images of individual cell that are labeled with Xist (red), Lamin B1 (green) and DAPI (blue) across different conditions, scale bars: 5 micrometers, according to embodiments of the present invention.
Figure 28B:
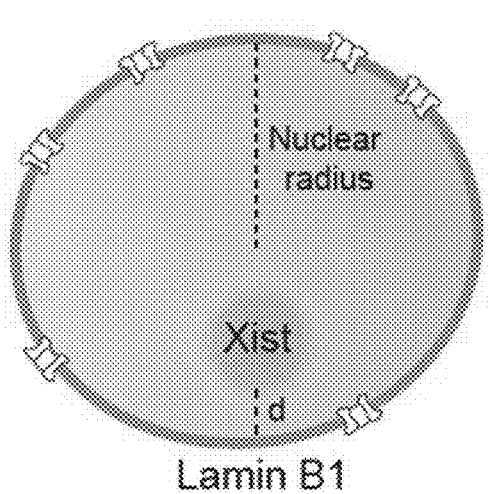
FIG. 28B is a schematic illustrating the normalized distance calculation between Xist and Lamin B1, according to embodiments of the present invention.
Figure 28C:
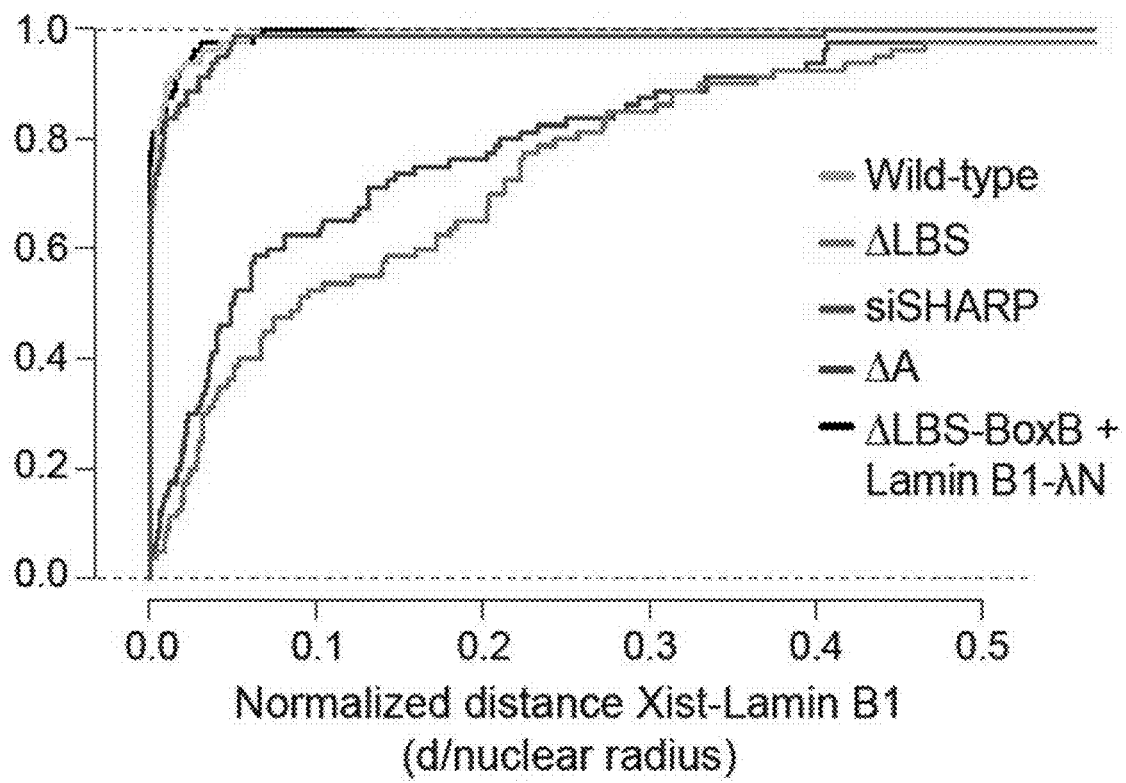
FIG. 28C is a graph plotting the cumulative frequency distribution of normalized distances between Xist and Lamin B1 across 80 individual cells across different conditions, according to embodiments of the present invention.

Because induction of XCI is known to lead to recruitment of the inactive X chromosome to the nuclear lamina, it was hypothesized that the Xist-LBR interaction might be required for mediating these structural changes. To test this, the distance between the Xist-coated nuclear compartment and Lamin B1 in the nucleus was measured using RNA FISH and immunofluorescence (FIGS. 28A-28B). Upon Xist induction in wild-type cells, it was found that the Xist compartment overlaps Lamin B1 signal in the vast majority of wild-type cells (~90%, FIG. 28C). In contrast, in ΔLBS-Xist and ΔA-Xist cells, the vast majority of cells displayed a clear separation between the Xist-coated compartment and Lamin B1 (~91% and ~85%, respectively, FIG. 28C), demonstrating a >20-fold increase in distance relative to wild-type Xist (FIG. 28C). These results demonstrate that recruitment of the inactive X chromosome to the nuclear lamina is directly mediated by the Xist RNA through its interaction with LBR.

The Gpc4 locus was selected to measure the distance between the Xist compartment and actively transcribed genes by RNA FISH because it is located >50 megabase pairs (Mbs) away from the Xist transcription locus. It was previously found that regions that are close to the Xist locus (within 5 Mbs) show higher levels of Xist localization simply because of its close linear distance. Although Atrx is also strongly depleted for Xist RNA localization by RAP-DNA, Artx was excluded from the imaging analysis because it is in close linear proximity to Xist (within 2.5 Mbs) and may therefore show higher levels of signal overlap simply because of the more limited resolution of these imaging experiments.

Figure 28D:
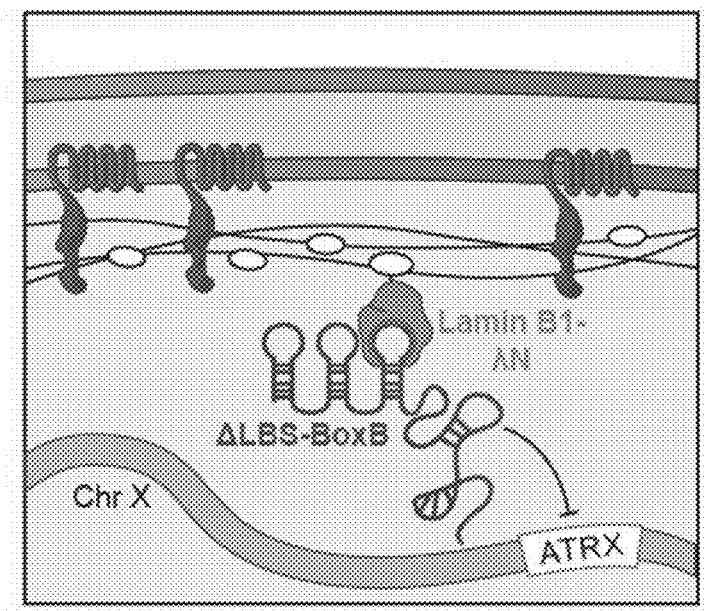
FIG. 28D A schematic illustrating the tethering of ΔLBS-BoxB to the nuclear lamina using the LaminB1-λN fusion protein, according to embodiments of the present invention.

Because LBR is required for Xist-mediated silencing and also leads to recruitment of Xist-coated DNA to the nuclear lamina, it was hypothesized that the function of LBR is to mediate recruitment of the X chromosome to the nuclear lamina and in this way leads to Xist-mediated transcriptional silencing. To test this, the Xist-LBR interaction was replaced with another protein that is also known to interact with the nuclear lamina. Specifically, the endogenous ΔLBS-BoxB Xist was used, which fails to interact with LBR, to create an interaction between Xist and Lamin B1 (FIG. 28D)—a distinct nuclear lamina protein that is not normally required for X chromosome silencing (FIG. 4). A Lamin B1-λN fusion protein was expressed and it was confirmed that in cells expressing ΔLBS-BoxB Xist, the Xist-compartment was recruited to the nuclear lamina to a similar extent as that observed in wild-type conditions (FIGS. 28A, 28C).

Figure 28E:
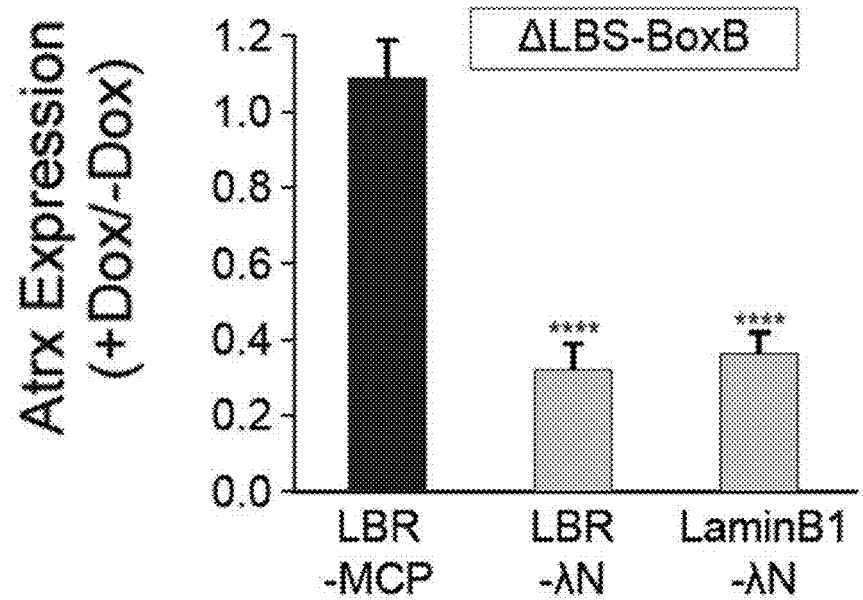
FIG. 28E is a graph plotting the expression of ΔLBS-BoxB along with expression of LBR-MCP (control), LBR-λN, or LaminB1-λN, with error bars represent the SEM across 50 individual cells, NS: not significant, **** p-value<0.001 relative to cells transfected with LBR-MCP by an unpaired two-sample t-test, according to embodiments of the present invention.
Figure 29A:
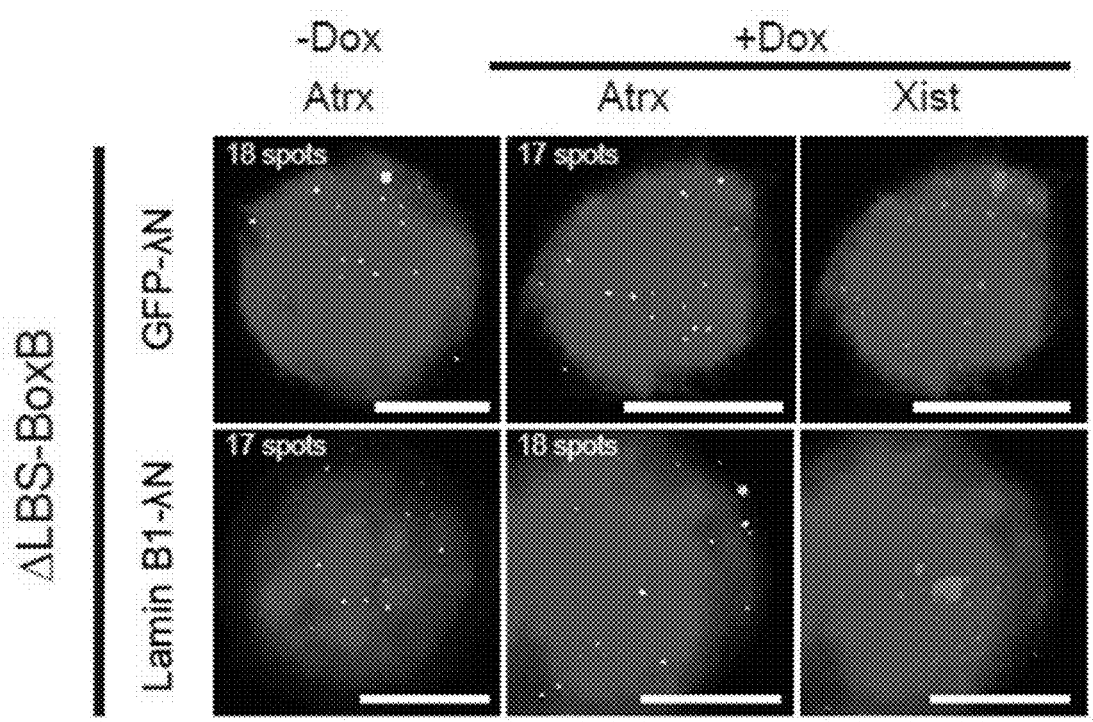
FIG. 29A shows representative images of individual cells for Atrx mRNAs (yellow) and Xist (red) along with DAPI (blue) in cells expressing ΔLBS-BoxB Xist transfected with LMNB1-λN fusion protein, with the number of identified mRNAs shown, scale bars: 5 micrometers, according to embodiments of the present invention.
Figure 29B:
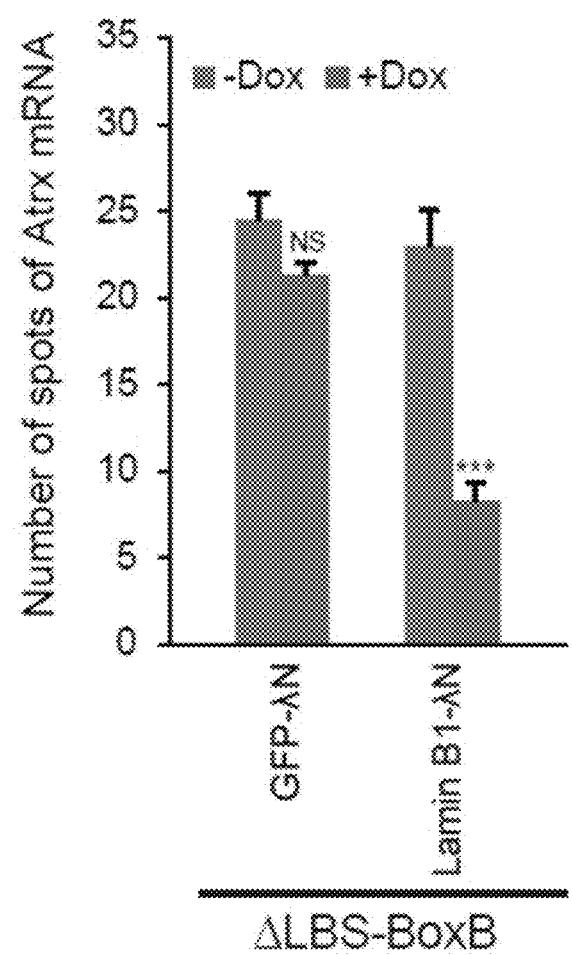
FIG. 29B is a graph plotting quantification of the copy number of Atrx mRNA for −Dox and +Dox cells expressing ΔLBS-BoxB Xist transfecting with LMNB1-λN fusion protein, with error bars representing the SEM across 50 individual cells, NS: not significant, *** p-value<0.005 relative to −Dox cells by an unpaired two-sample t-test, according to embodiments of the present invention.

Having synthetically recruited Xist to the nuclear lamina, it was tested whether Xist can silence transcription on the X chromosome. Indeed, tethering Xist to the nuclear lamina rescues the Xist silencing defect observed in ΔLBS cells to the same extent as that observed after rescuing directly with LBR-λN (FIG. 28E, FIGS. 29A-29B). Together, these results demonstrate that Xist-mediated recruitment of the X chromosome to the nuclear lamina is required for Xist-mediated transcriptional silencing. Furthermore, these results demonstrate that the function of LBR in Xist-mediated silencing is due to its ability to recruit the X chromosome to the nuclear lamina.

To explore why Xist-mediated recruitment to the nuclear lamina is required for transcriptional silencing, the possibility that recruitment to the nuclear lamina, a nuclear territory enriched for silenced DNA and repressive chromatin regulators, acts to directly silence transcription on the X chromosome was considered. Consistent with this notion, recruitment of actively transcribed genes to the nuclear lamina has been shown, in some cases, to be sufficient to silence transcription. To test this hypothesis, the nuclear lamina association of the Xist-coated territory upon knock down of SHARP was investigated, which also fails to silence transcription on the X chromosome. In the absence of SHARP, the Xist-coated compartment is still localized at the nuclear lamina, demonstrating a comparable distance distribution between Xist and Lamin B1 to that observed for wild-type Xist (FIGS. 28A, 28C). These results demonstrate that Xist-mediated recruitment of the X chromosome to the nuclear lamina does not directly lead to transcriptional silencing.

Example 14

Localization of Xist Mediated by LBR

Figure 30A:
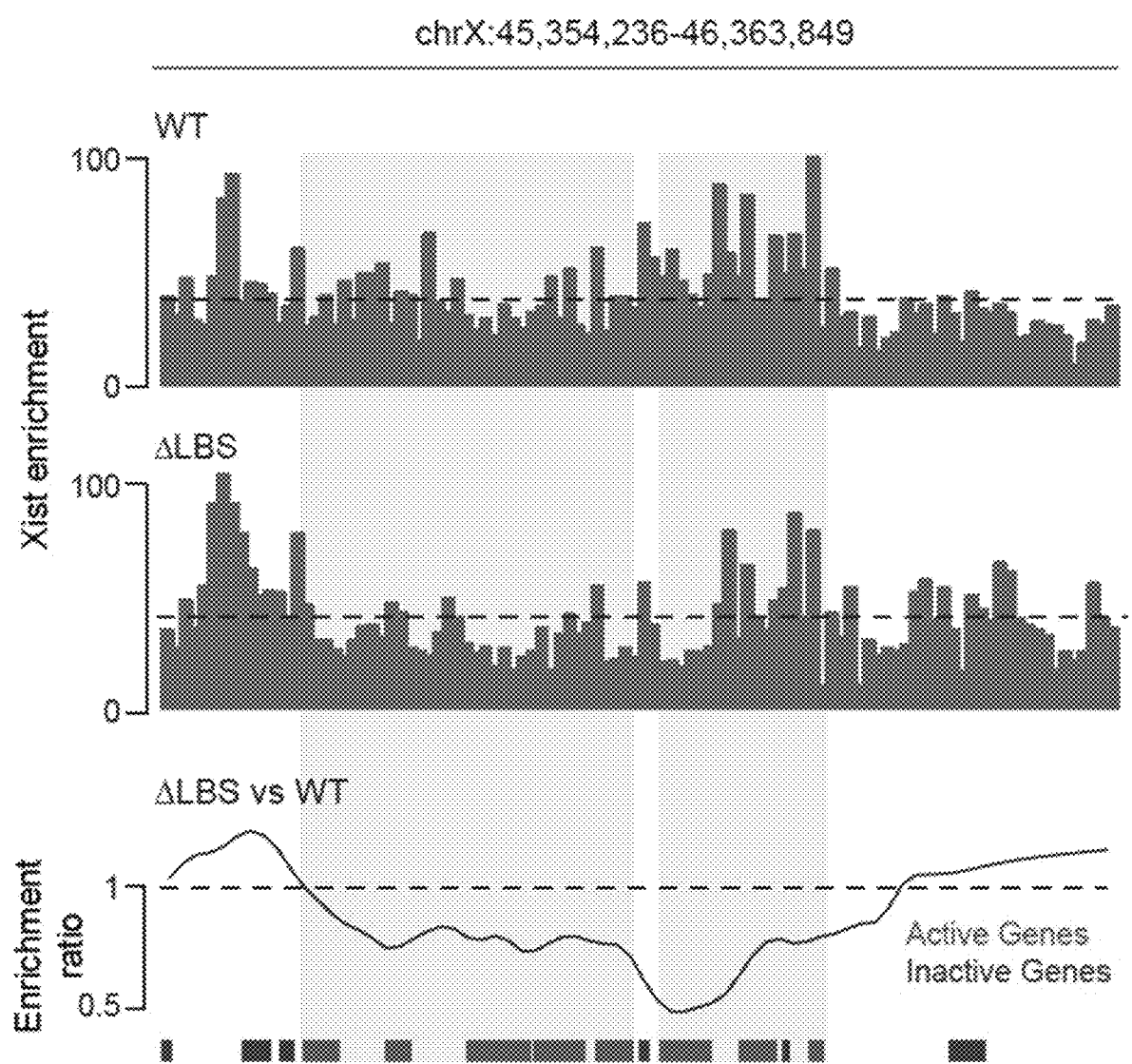
FIG. 30A is graph plotting Xist RNA localization as measured by RAP-DNA for wild type (top), ΔLBS-Xist (middle), and the fold change (bottom) across a representative region of the X chromosome that contains a cluster of actively transcribed genes (red) and inactive genes (blue), with dashed lines represent the average Xist enrichment over this region in wild type cells, according to embodiments of the present invention.
Figure 30B:
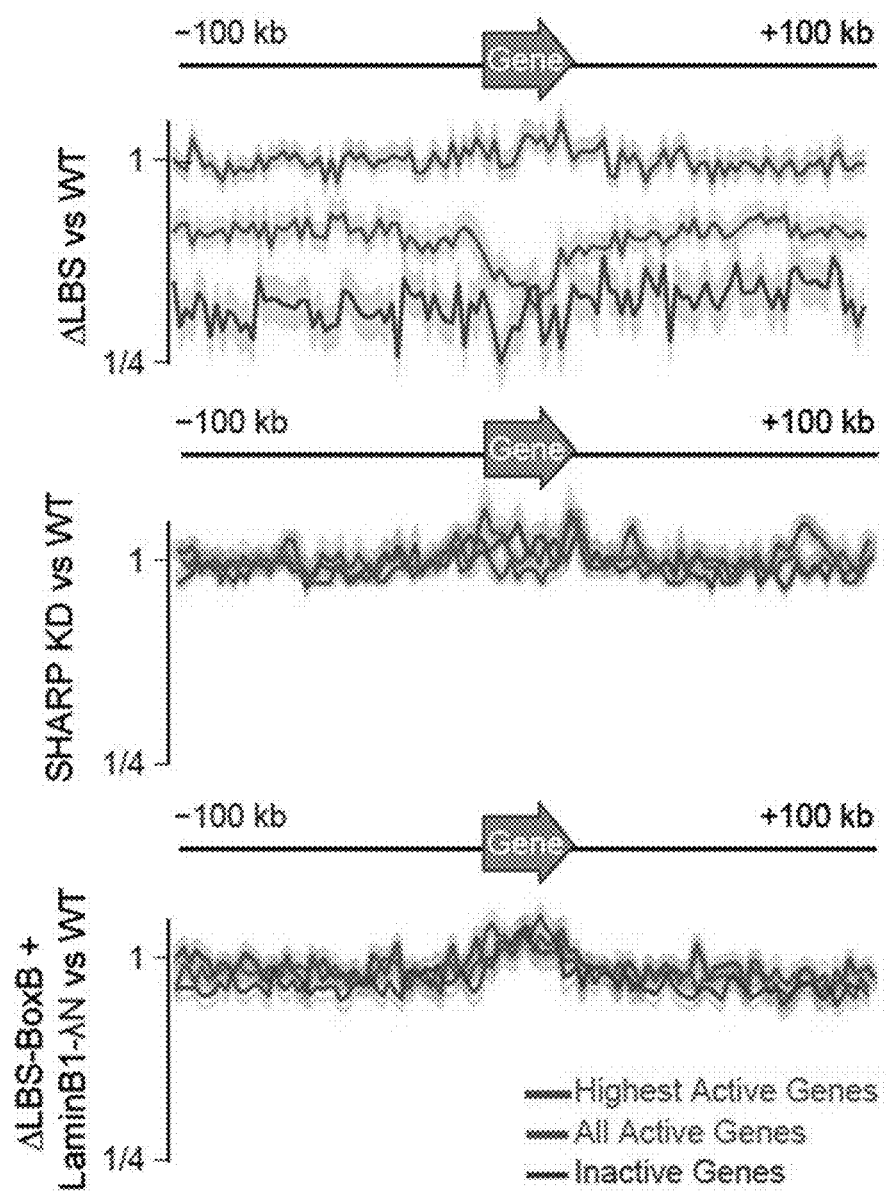
FIG. 30B shows graphs depicted the average Xist enrichment across the most highly actively transcribed genes (dark red, RPKM >5), all actively transcribed genes (red, RPKM >1), and inactive genes (blue) on the X-chromosome for ΔLBS, knockdown of SHARP, and ΔLBS-BoxB+LMNB1-λN cells compared to wild type cells, with shaded areas represent 95% confidence interval, in which enrichment levels are normalized to the average enrichment level across the entire X-chromosome, according to embodiments of the present invention.
Figure 31:
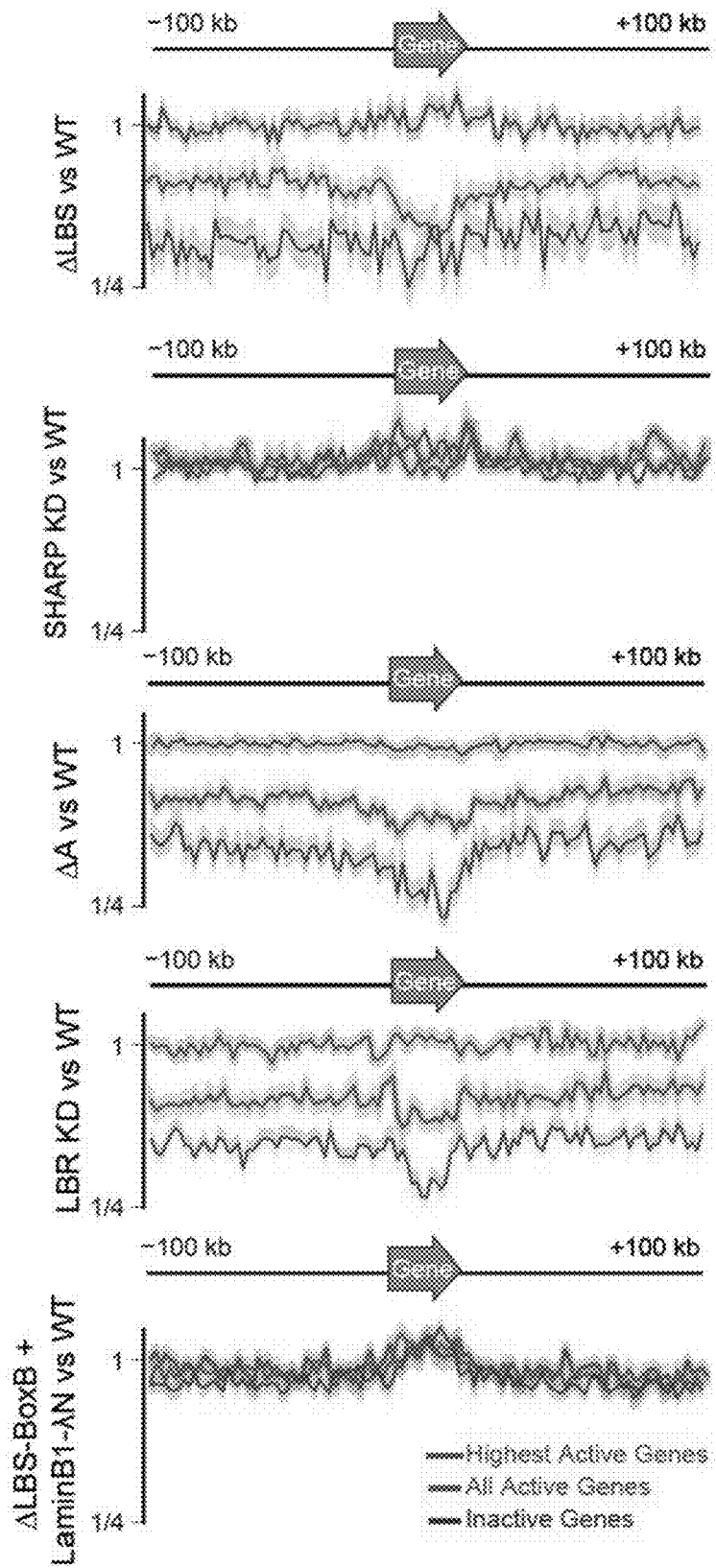
FIG. 31 shows graphs depicting the fold-change of Xist enrichment averaged across the most highly actively transcribed genes (dark red, RPKM expression >5), all actively transcribed genes (red, RPKM >1), and inactive genes (blue) on the X-chromosome for ΔLBS, SHARP knock down, ΔA, LBR knockdown with dCas9-KRAB, and ΔLBS-BoxB+LMNB1-λN cells in comparison to wild type Xist cells, with the shaded areas representing 95% confidence interval for the average enrichment, in which enrichment level are normalized to a mean of one across the X-chromosome and are plotted on a log scale, according to embodiments of the present invention.
Figure 32:
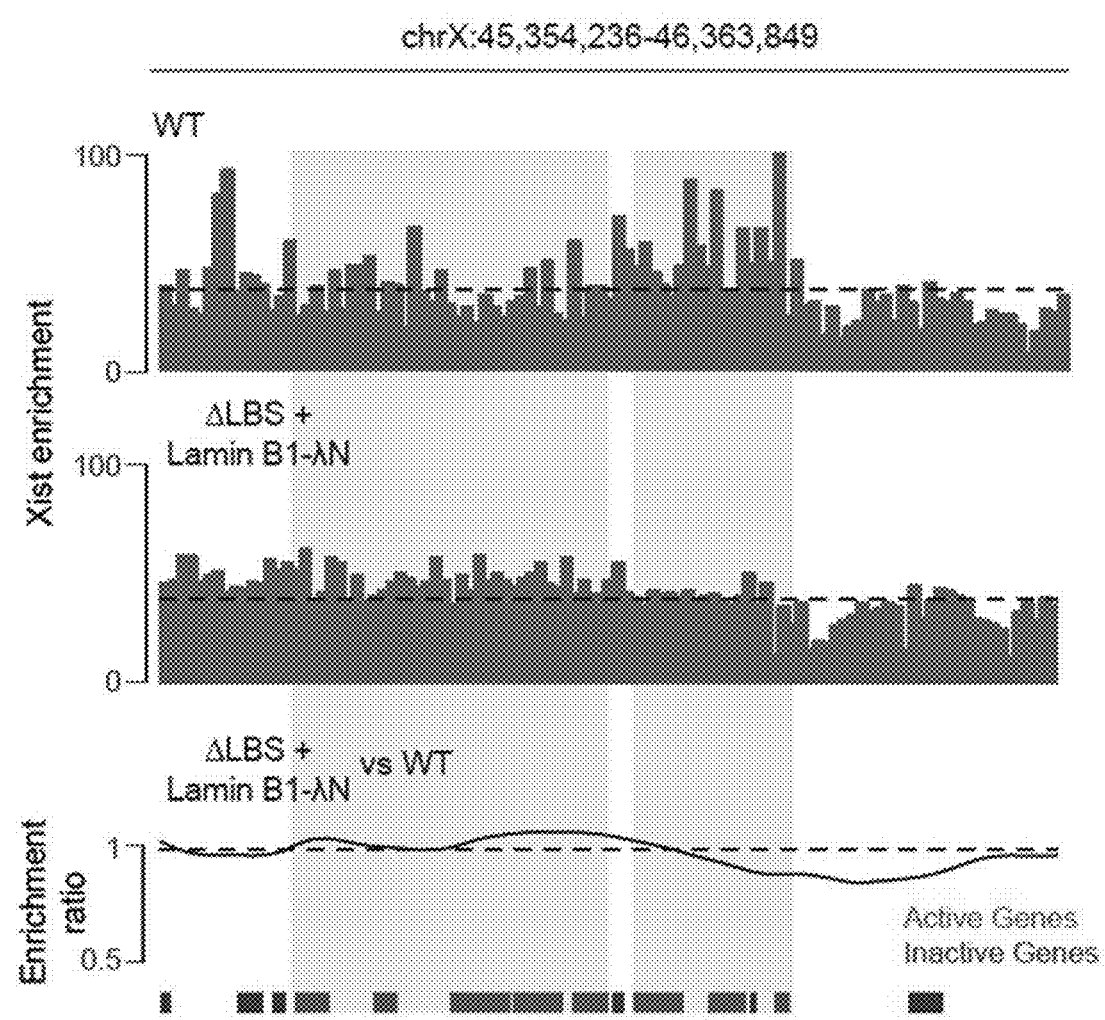
FIG. 32 shows graphs depicting the comparison of wild type and LMNB1-λN in ΔLBS cells of Xist enrichment of a representative region, with the gray boxes mark the regions that are depleted for Xist association in ΔLBS cells in comparison to wild type cells, and the dashed lines represents the regional average Xist enrichment level of wild type cells, according to embodiments of the present invention.

An alternative hypothesis is that LBR-mediated recruitment of the X chromosome to the nuclear lamina repositions active genes into the Xist-coated nuclear compartment thereby allowing Xist to spread across the X chromosome. Consistent with this notion, deletion of the A-repeat was previously shown to lead to a defect in Xist spreading to genes that are actively transcribed prior to initiation of XCI. To test this hypothesis, the localization of Xist across the X chromosome was explored using RAP-DNA, a method that enables comprehensive mapping of Xist to genomic DNA (17). In ΔLBS-Xist cells or upon knock down of LBR, a strong depletion of Xist RNA localization across regions of actively transcribed genes was observed, comparable to the defect observed in ΔA-Xist cells (~3-fold relative to wild-type, FIGS. 30A-30B, FIG. 31). Notably, it was found that Xist RNA localization is even more strongly depleted over more highly transcribed genes (FIG. 30B). To ensure that this localization defect is not merely due to loss of Xist-mediated silencing, SHARP was knocked down and an Xist localization defect was not observed (FIG. 30B, FIG. 31). Notably, it was found that synthetically tethering ΔLBS-BoxB Xist to the nuclear lamina using a Lamin B1-λN fusion enables Xist to spread to active genes to a similar level as that observed in wild-type conditions (FIG. 30B, FIG. 32).

Example 15

Xist Localization to Active Gene and Exclusion of RNA PolII

Figure 30C:
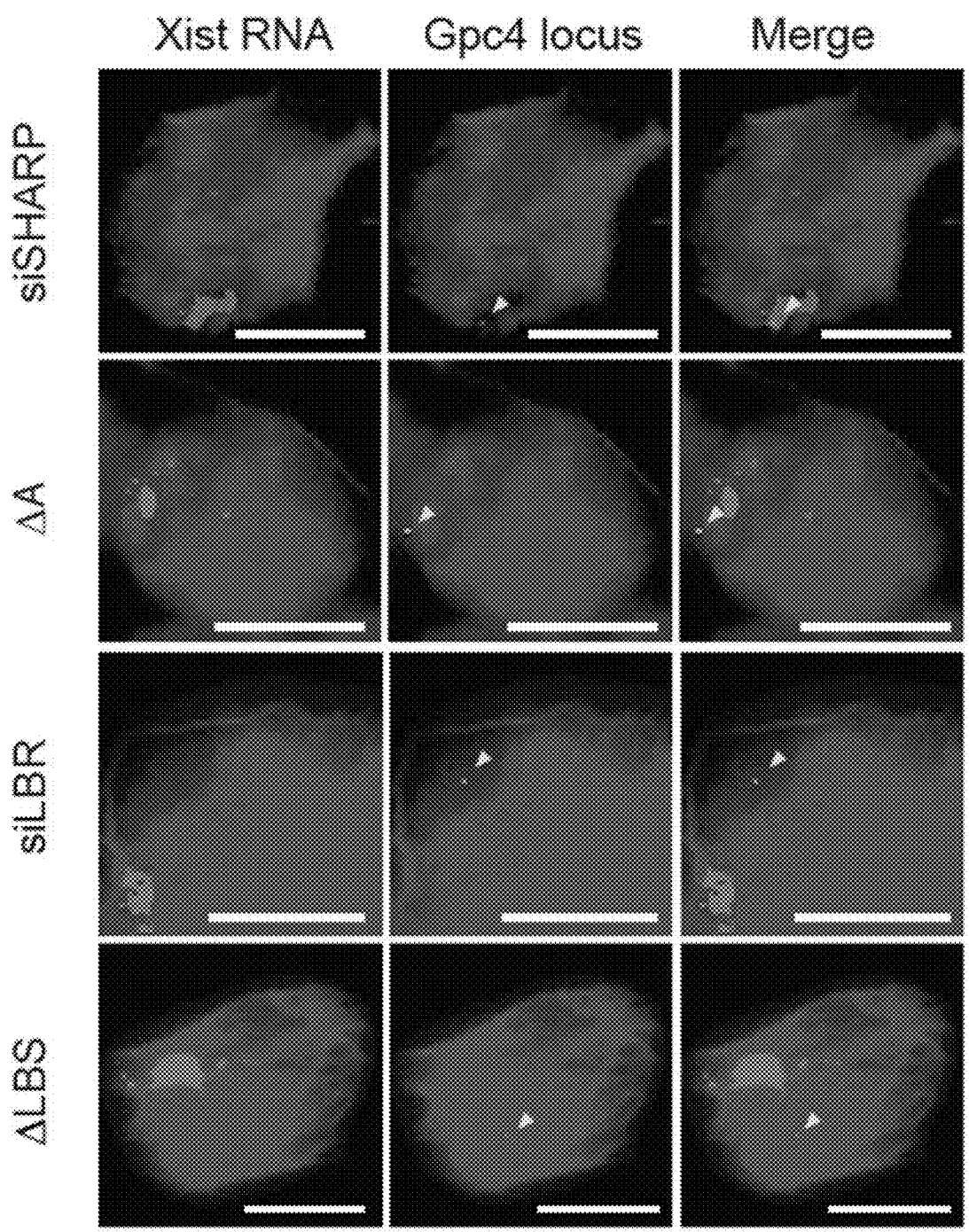
FIG. 30C shows representative images of individual cell that are labeled with Xist (red), Gpc4 locus (green) and DAPI (blue) across different cell lines (rows), with scale bars: 5 micrometers, according to embodiments of the present invention.
Figure 30D:
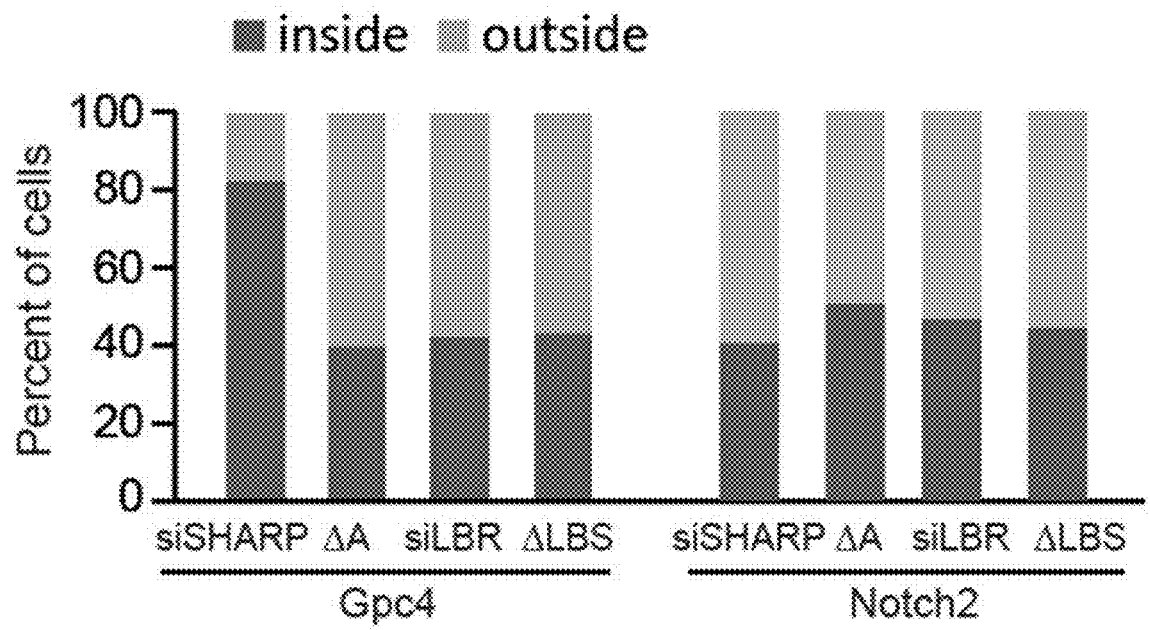
FIG. 30D is a graph plotting the percentage of cells where the Gpc4 locus (X chromosome) or Notch2 loci (autosomal) were found inside or outside of the Xist cloud across 80 individual cells, according to embodiments of the present invention.
Figure 30E:
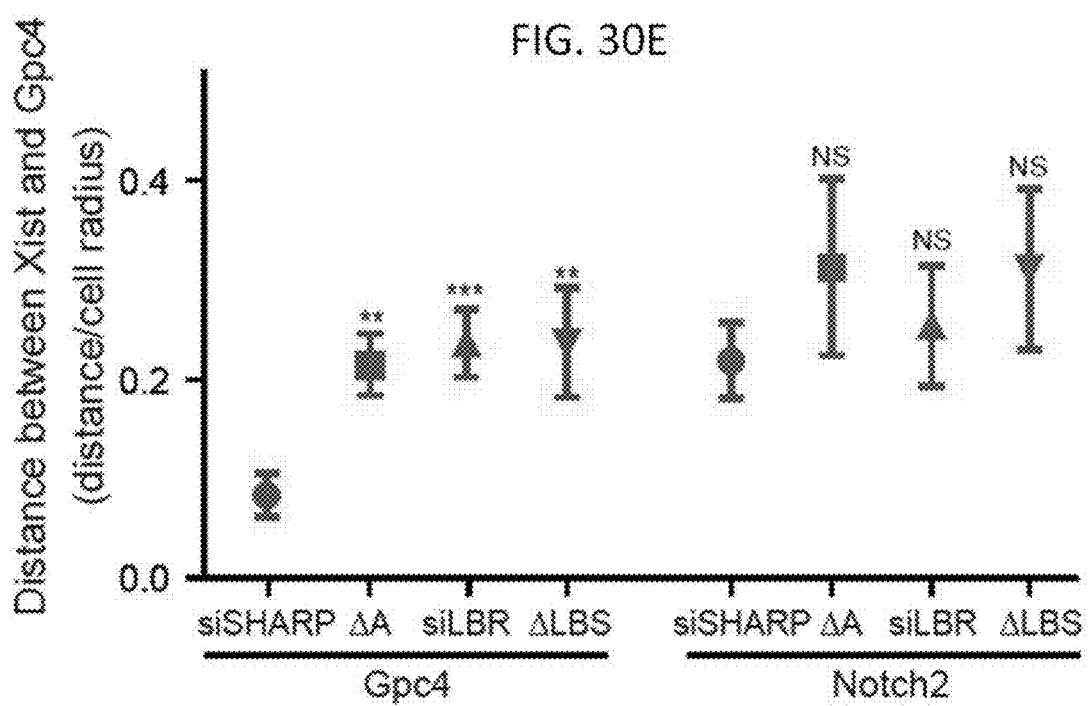
FIG. 30E is a graph plotting the distance from the Gpc4 locus or Notch2 loci to the Xist-coated compartment across 80 individual cells for different cell lines, NS: not significant,  p-value<0.01, * p-value<0.005 relative to siSHARP by an unpaired two-sample t-test, according to embodiments of the present invention.
Figure 33A:
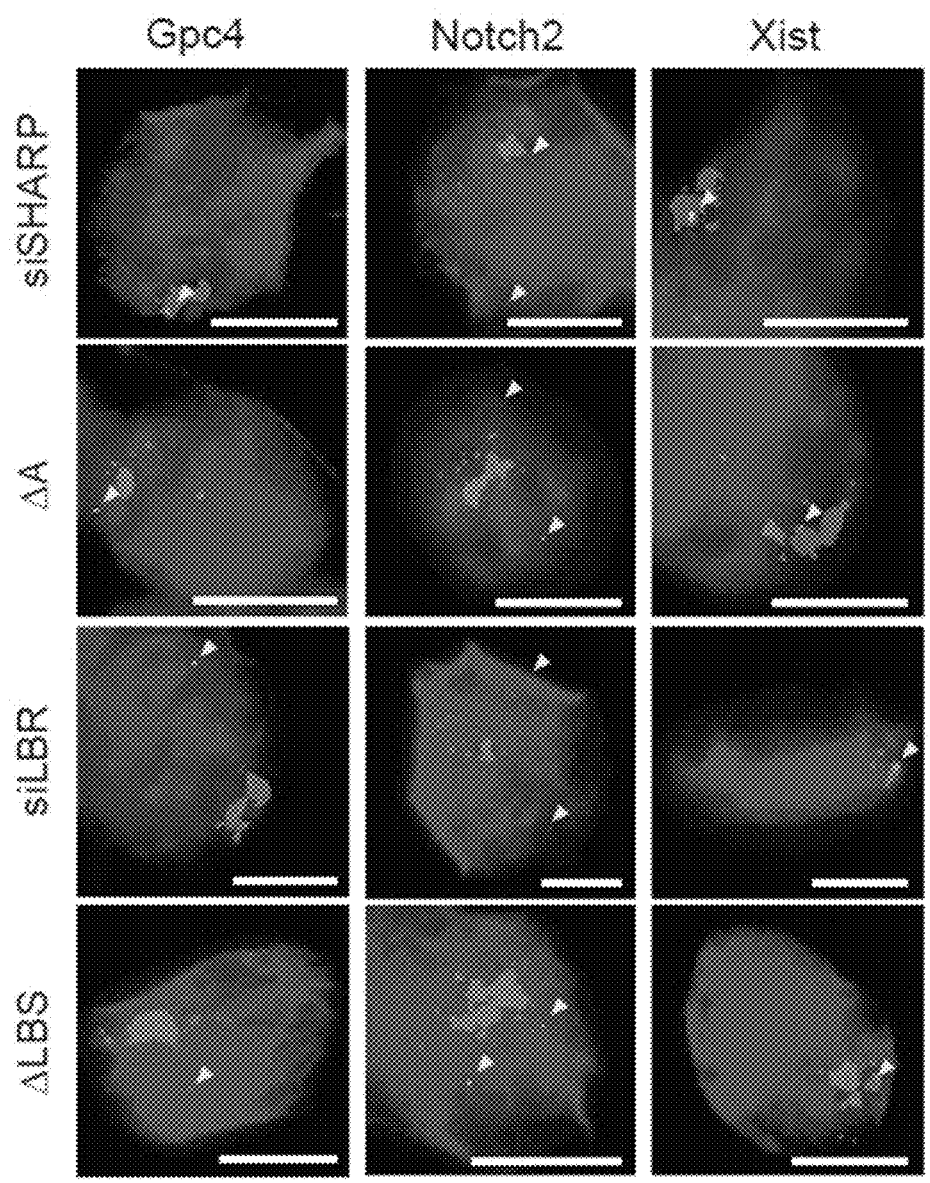
FIG. 33A shows representative images of individual cell that are labeled with Gpc4 locus, Notch2 loci, or Xist locus (green) along with Xist (red) and DAPI (blue) across different cell lines (rows), according to embodiments of the present invention.
Figure 33B:
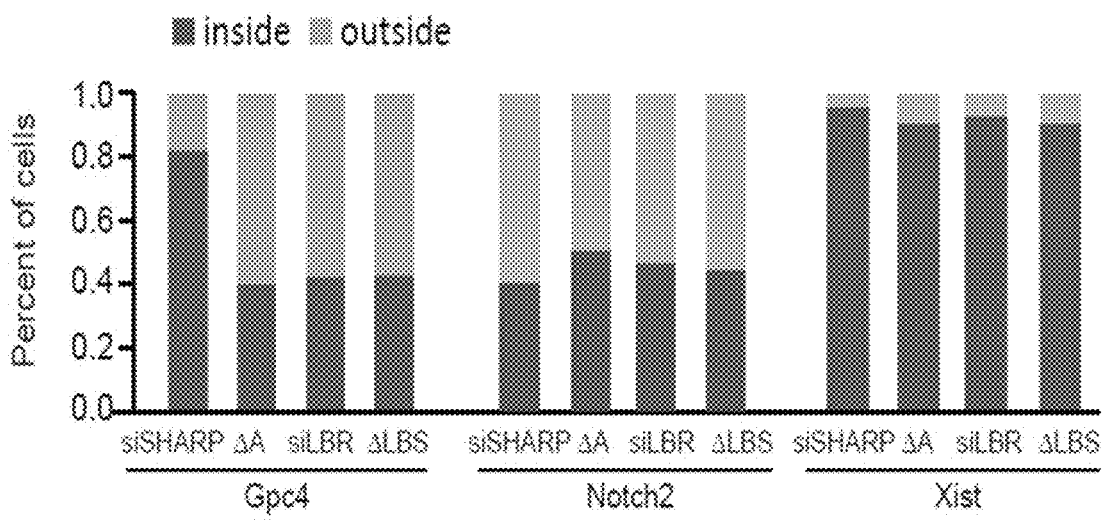
FIG. 33B is graph plotting the percentage of cells where Gpc4 locus, Notch2 loci or Xist locus were found inside or outside of the Xist cloud across 80 cells, according to embodiments of the present invention.
Figure 33C:
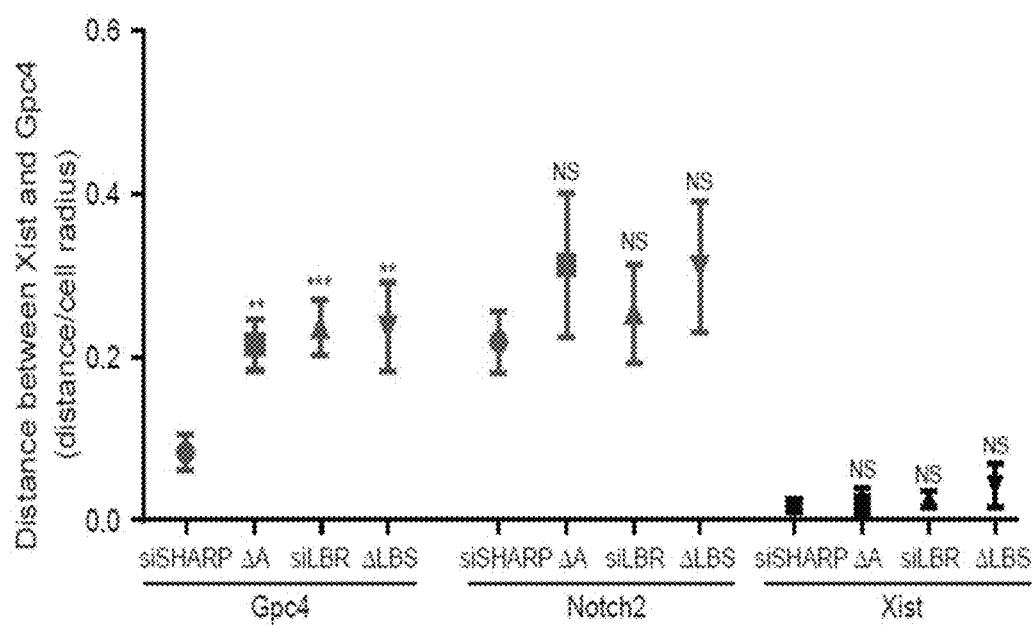
FIG. 33C is a graph plotting the distance from Gpc4 locus, Notch2 loci or Xist locus to Xist cloud across different cell lines across 80 cells, with error bars represent the SEM across 80 individual cells, NS: not significant,  p-value<0.01, * p-value<0.005 relative to siSHARP by an unpaired two-sample t-test, scale bars: 5 micrometers, according to embodiments of the present invention.

To determine whether this spreading defect is due to a failure to reposition actively transcribed genes into the Xist-coated compartment, the position of the genomic locus of an actively transcribed gene relative to the Xist-coated compartment was measured using RNA FISH (FIG. 30C). In ΔLBS cells or upon knock down of LBR, the distance between the Xist compartment and the locus of an actively transcribed X chromosome gene (Gpc4 locus) was comparable to the distance between Xist and an autosomal gene (Notch2 locus) (see Methods, FIGS. 30D, 30E). In contrast, upon knockdown of SHARP, it was found that the Gpc4 locus overlapped the Xist compartment in the vast majority of cells (~80%, FIG. 30D), displaying a comparable frequency of overlap to that observed for the Xist genomic locus itself (~90%, FIGS. 33A, 33B, 33C). Because Xist can still spread to active genes upon knockdown of SHARP, which is known to be required for the exclusion of RNA PolII (FIGS. 15A-15C), the results here demonstrate that spreading to active genes and exclusion of RNA PolII are independent functions that are both required for chromosome-wide transcriptional silencing.

Example 16

Model for Xist

Figure 34:
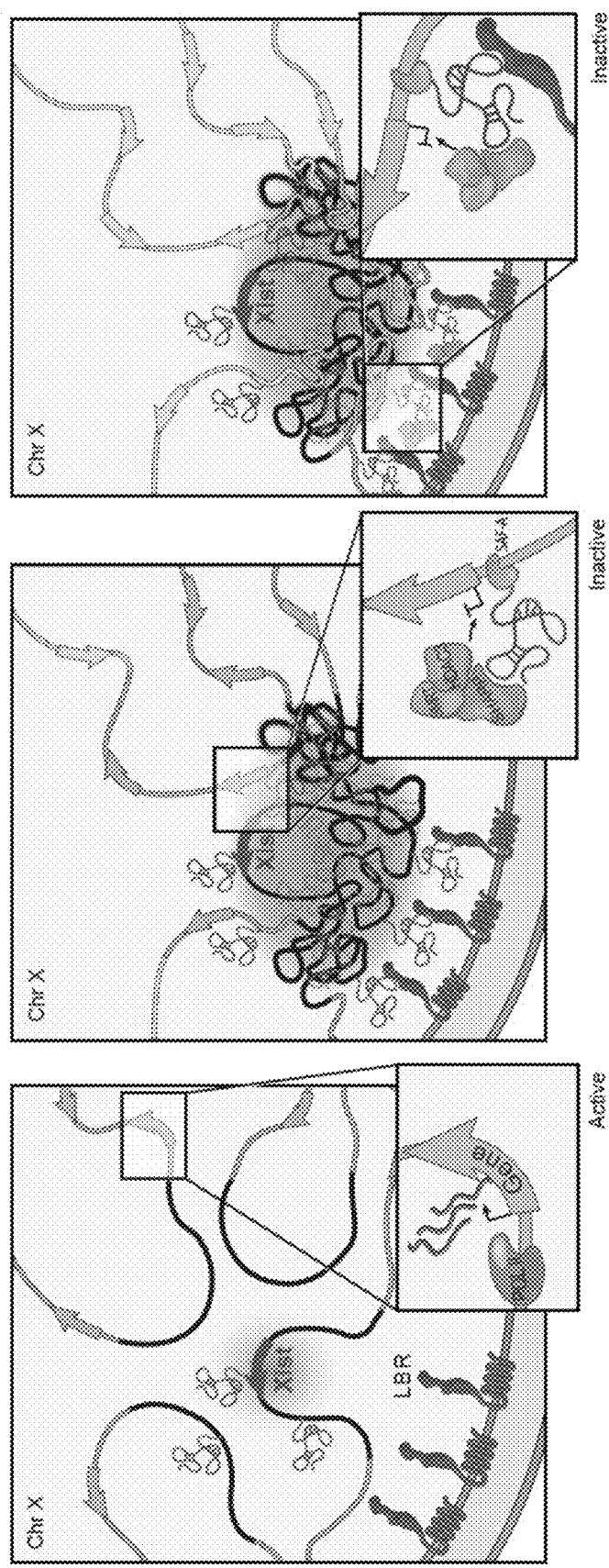
FIG. 34 is a schematic, according to embodiments of the present invention, depicting that: Upon initiation (left panel), Xist spreads to regions that are closest to the Xist transcription locus (red arrow). These initial Xist-coated DNA regions (black regions) are recruited to the nuclear lamina through an interaction between Xist and LBR (middle panel). This recruitment changes the 3-dimensional organization of X-chromosome and repositions active genes (green regions) closer the Xist transcription locus enabling Xist, and its SHARP/SMRT/HDAC3 silencing complex, to spread to these new sites by 3-dimensional proximity transfer. These sites are then recruited to the nuclear lamina, effectively bringing another set of active genes (yellow regions) into closer contact with the Xist transcription locus (right panel). This iterative process would enable Xist to spread to, and silence, actively transcribed genes across the entire X-chromosome.

Together, the results here are depicted in a model for how Xist shapes the 3-dimensional nuclear structure of the inactive X chromosome to spread to active genes and silence chromosome-wide transcription (FIG. 34). Xist initially localizes to the core of the X chromosome territory by localizing at DNA sites that are in close 3-dimensional proximity to its transcriptional locus as described in Engreitz et al., 2013, supra, and Simon et al., 2013, *Nature*, 504:465-469, the entire content of which is herein incorporated by reference. These initial Xist localization sites are generally inactive prior to Xist induction. The Xist-coated DNA, like other chromosomal DNA regions, will dynamically sample different nuclear locations and, because Xist binds LBR, will become tethered at the nuclear lamina when it comes into spatial proximity. This lamina association is known to constrain chromosomal mobility and by doing so would position the Xist-coated DNA away from the actively transcribed Xist transcription locus enabling other DNA regions on the X chromosome, which are physically linked to these tethered regions, to be brought into closer spatial proximity of the Xist transcription locus. In this way, Xist and its silencing factors can spread to these newly accessible DNA regions on the X chromosome.

Example 17

Material and Methods for Examples 9-16

Mouse ES Cell Culture and Xist Induction.

All mouse ES cell lines were cultured in serum-free 2i/LIF medium as described herein and Engreitz et al., 2013, supra. The following cell lines were used: (i) Male ES cells expressing Xist from the endogenous locus under control of a tet-inducible promoter (pSM33 ES cell line) as described in Engreitz et al., 2013, supra. (ii) Male ES cells carrying a cDNA Xist transgene without the A-repeat integrated into the Hprt locus under control of the Tet-inducible promoter as described in Wutz et al., 2002, supra (ΔA-Xist, cells were kindly provided by A. Wutz). Xist expression was induced by treating cells (pSM33 and ΔA-repeat deletion) with 2 µg/ml doxycycline (Sigma) for 6 hours or 16 hours depending on the assay performed.

To measure Xist-mediated silencing, a previously developed male mouse embryonic stem (ES) cell line was used containing a doxycycline-inducible Xist expressed from its endogenous location. Importantly, this inducible system has been shown to represent a well-synchronized model that accurately reflects the initiation of XCI. Furthermore, this male-inducible system is more sensitive for identifying proteins that affect silencing compared to a female system because Xist-mediated silencing in males will lead to loss of 100% of X-chromosome transcripts rather than only 50% in a female system, which still retains one active X. Moreover, because this system is well synchronized, relative to differentiation induced activation, it provides more reliable measurements of silencing at a given time point.

Gpc4 and Atrx were selected because they are X chromosome genes that are well expressed prior to Xist induction and are normally silenced by 16 hours of Xist induction in the doxycycline-inducible system (FIG. 2). Furthermore, it was shown that these two genes, which are located at varying distances from the Xist transcription locus across the X chromosome, accurately reflect the transcriptional status of many genes across the inactive X chromosome.

The X chromosome expression was measured before and after Xist induction using single molecule FISH. This approach provides more sensitive measurements relative to aggregate based methods because it allows us to analyze only cells that induce Xist expression (~50% in the system used here). Furthermore, it allows for analysis of individual cells that successfully deplete the target mRNA of interest (siRNA experiments) or that contain the transfected fusion proteins in our experiments.

siRNA Transfections.

For siRNA knockdown experiments, 20 nM siRNAs were transfected using the Neon transfection system (settings: 1200V, 40 ms width, 1 pulse). For each transfection, two 10 µL transfections with the same siRNA were carried out in succession using 100,000 cells each, mixed, and plated equally between two poly-D-lysine (Sigma) and 0.2% gelatin (Sigma)-coated #1.5 coverslips placed into wells of a 24-well plate containing 2i media. After 48 hours, 2i media was replaced and cells on one coverslip of each pair were treated with 2 µg/mL doxycycline (Sigma) for 16 hours to induce Xist expression. Coverslips were then fixed in Histochoice (Sigma) for 10 min, washed thoroughly in PBS, and dehydrated in ethanol for storage until FISH staining.

For all proteins and non-targeting control pool, siRNAs pools were used from Dharmacon (ON-TARGETplus SMARTpool siRNAs). For each cell analyzed, it was ensured that the siRNA successfully reduced the targeted mRNA expression by >70%.

Integrating BoxB Sequence into Xist Locus.

Three copies of the BoxB hairpin sequence (38) into nucleotide 16,523 of the endogenous Xist RNA in pSM33 ES cell line using CRISPR-mediated homologous recombination as described in Cong et al., 2013, Science, 339:819-813, the entire content of which is herein incorporated by reference. Specifically, a construct expressing Cas9 driven from a pCAG promoter, a guide RNA targeting the 3' region of the Xist locus (sgRNA sequence: CCTCATCCT-CATGTCTTCTC) (SEQ ID NO: 8), and a single strand DNA ultramer (IDT) containing 3×-BoxB sequence flanked with 70 nucleotides of upstream and downstream homologous sequence of the insertion site were co-transfected. Single colonies were picked from transfected cells and verified BoxB integration using PCR and Sanger sequenced successful integration lines with primers flanking the integration site and confirmed correct insertion. To ensure that the Xist-BoxB was still able to silence the X chromosome by expressing it and measuring transcriptional silencing of Atrx (FIGS. 23A-23B).

UV Crosslinking.

Cells were washed once with PBS and then crosslinked on ice using 0.4 Joules/cm2 (UV4k) of UV at 254 nm in a Spectrolinker UV Crosslinker. Cells were then scraped from culture dishes, washed once with PBS, pelleted by centrifugation at 1500×g for 4 minutes, and flash frozen in liquid nitrogen for storage at −80° C.

Immunoprecipitation and RT-qPCR.

Mouse ES cells were induced then crosslinked with UV4k as described above. Pellets of 20M cells were lysed and treated with TURBO DNase (Ambion) and incubated for 10 minutes at 37° C. in an Eppendorf Thermomixer C to digest genomic DNA. The lysate was pre-cleared by incubation with 180 µL of Dynabeads Protein G magnetic beads (Life Technologies). Meanwhile, 10 µg of antibody for immunoprecipitation was coupled to 75 µl Protein G magnetic beads. After pre-clearing was completed, the lysate was then mixed with the appropriate antibody-coupled Protein G magnetic beads and incubated for overnight at 4° C. on a Hulamixer sample mixer (Life Technologies) for protein capture. After immunoprecipitation, beads were washed with a wash buffer of 1×PBS with detergents and then captured nucleic acids were eluted by digesting all proteins with 5.6 U proteinase K (New England Biolabs). Eluted RNA was purified using the RNA Clean and Concentrator-5 Kit (Zymo Research) and RT-qPCR was performed as described previously (17) to evaluate RNA enrichment. The antibodies used for immunoprecipitation were anti-FLAG® M2 (Sigma-Aldrich; F1804) (for ΔTM- and ΔRS-LBR transfected cells), anti-SHARP (Bethyl; A301-119A), and customized LBR antibody from GenScript (LBR #4; 540774-1).

Crosslinking and Immunoprecipitation (CLIP) Analysis.

Doxycycline-induced pSM33 mouse male ES cells were crosslinked for 6 hours with 0.4 J of UV254. Cells were lysed and RNA was digested with RNase I to achieve a size range of 100-500 nucleotides in length. Lysate preparations were precleared by mixing with Protein G beads for 1 hr at 4° C. For each CLIP sample, target proteins were immunoprecipitated from 20 million cells with 10 ug of antibody and 75 µl of Protein G beads. The antibodies were pre-coupled to the beads for 1 hr at room temperature with mixing before incubating the precleared lysate to the beads-antibody overnight at 4 C. After the immunoprecipitation, the beads were washed four times with High salt wash buffer (50 mM Tris-HCl pH 7.4, 1 M NaCl, 1 mM EDTA, 1% NP-40, 0.1% SDS, 0.5% sodium deoxycholate) and four times with Wash buffer (20 mM Tris-HCl pH 7.4, 10 mM MgCl2, 0.2% Tween-20). RNAs were then eluted with NLS elution buffer (20 mM Tris-HCl pH 7.5, 10 mM EDTA, 2% N-lauroylsarcosine, 2.5 mM TCEP) with 100 mM DTT. Samples were then run through a standard SDS-PAGE gel and transferred to a nitrocellulose membrane, and a region 75 kDa above the molecular size of the protein of interest was isolated and treated with Proteinase K (NEB) followed by phenol/chloroform/isoamyl alcohol (pH 6.5) extraction to isolate the RNAs. Extracted RNAs were then purified with RNA Clean & Concentrator™-5 (Zymo). After a dephosphorylation treatment, the RNA in each sample was ligated to a mixture of barcoded adapters in which each adapter had a unique barcode identifier according to the Massively Multiplexed RNA Sequencing method as described in Shishkin et al., 2015, *Nat. Methods,* 12:323-325, the entire content of which is herein incorporated by reference. After ligation, beads were rinsed with 1×PBS and detergents and then 5×PBS and detergents prior to pooling 3-4 IPs per new tube. The proteins and RNA were then eluted from the Protein G beads with 6M urea and 40 mM DTT at 60° C. Protein-RNA complexes were separated away from free RNA and the proteins were then digested with Proteinase K. From the barcoded RNA in each pool, Illumina sequencing libraries were generated as previously described in Engreitz et al., 2014, supra.

Input samples: As a control, an "input" RNA control was sequenced for each immunoprecipitated protein. To do this, 10% of the total cellular lysate was saved prior to the immunoprecipitation step. These samples were then run through an SDS-PAGE gel alongside the immunoprecipitated sample and gel extracted from the identical region as the protein analyzed. Sequencing libraries were made from these samples as described above.

Analysis of CLIP Data.

The enrichment for any RNA region was computed and visualized by normalizing the number of reads upon immunoprecipitation with a specific protein relative to the number of reads in its size-matched input control (input sample). Specifically, the total number of reads overlapping the RNA region were counted in either the immunoprecipitation sample or the input control. To account for differences in read coverage between samples, each of these numbers was normalized to the total number of reads within the same experiment. This generates a normalized score, per region, within each sample. An enrichment metric was measured by taking the ratio of these normalized values (IP/Input).

Protein binding sites on the Xist RNA were identified by identifying regions that were enriched relative to the same region in the input control ("differential enrichment") and also was enriched relative to all other regions on the remainder of the Xist RNA ("local enrichment"). The differential enrichment accounts for biases in the size-selected input sample that would lead to a pile up of reads in specific regions of the RNA, but that do not reflect true protein binding sites. In contrast, the local enrichment accounts for cases where a given RNA might have higher overall levels of protein binding relative to the input. To compute significant enrichment, the differential enrichment as defined above (IP/Input) was computed for each window (window size=100 nucleotides). The local enrichment was computed for each region by taking the normalized number of reads for each region (IP) and dividing it by the normalized number of reads over the entire Xist RNA. To make these rates comparable, each number was divided by their respective region length prior to taking the ratio. Then, 1,000 random permutations of the reads in the IP samples were generated and paired input samples across the Xist RNA. For each permutation, the differential and local enrichments were computed and generated an empirical distribution of the maximum value observed for each permutation. A multiple-testing corrected p-value was assigned to each region by comparing the observed differential and local enrichment values to these permutation distributions. Significant windows that had a differential p-value <0.01 and a local p-value<0.01 were identified.

Three LBR binding sites from 535-1608 nucleotides (LBS-1), 9506-10245 nucleotides (LBS-2), and 11732-11956 nucleotides (LBS-3) were identified. A SHARP binding site from 317-1056 nucleotides and PTBP1 binding site from 10859-11344 nucleotides on Xist were also identified.

Generating ΔLBS and ΔLBS-BoxB Xist.

A ΔLBS and ΔLBS-BoxB was generated using CRISPR-mediated knock out. To generate ΔLBS and ΔLBS-BoxB cells, mouse pSM33 ES cells and Xist-BoxB cells were transfected with two guide RNAs flanking the LBS-1 region of Xist (sgRNA sequence: CACCGAG-GAGCACAGCGGAC (SEQ ID NO: 9) and TAAGGACGT-GAGTTTCGCTT) (SEQ ID NO: 10) and co-transfected along with the Cas9 construct described above to create a deletion of LBS-1 by non-homologous end joining. Single colonies were isolated from the transfected cells for both cell lines and verified that the LBS-1 region was deleted from the genome using PCR and Sanger sequencing with primers flanking the A-repeat region of Xist. It was ensured that the ΔLBS affected binding of the LBR protein using IP-qPCR and CLIP sequencing across the entire Xist RNA. It was also ensured that there was no impact on SHARP binding using IP-qPCR.

dCas9-KRAB Silencing.

To generate stable LBR and SHARP knock down cells, a puromycin resistant construct expressing dCas9-KRAB driven by an Ef1a promoter and a guide RNA with scaffolding structure targeting the region near the transcription start site of LBR (sgRNA sequence: CGGGACTCCGCCGCGTG) (SEQ ID NO: 11) or SHARP (sgRNA sequence: CGGTGGCGTCGGCAGCGG) (SEQ ID NO: 12) was co-transfected. Transfected cells were selected on 1 µg/mL puromycin (Sigma-Aldrich) for four days to enrich for cells that contain the dCas9-KRAB. FISH was used to verify that >90% of these puro-resistant cells had no detectable amount of mRNA after four days puromycin selection.

LBR Protein Mutagenesis.

A human cDNA containing the full-length ORF of LBR was obtained from the DNASU plasmid repository as a Gateway entry clone and was inserted into the pCAG-GW-λN-3×FLAG-BSD vector using an LR recombination reaction (Invitrogen). To generate ΔRS-LBR and ΔTM-LBR, λN-3×FLAG tagged full-length LBR construct was truncated using PCR-mediated deletion with primers flanking the deletion region.

Expression of cDNA Rescue Constructs.

Mouse ES cells were electroporated using the Neon transfection system (Invitrogen) with mammalian expression vector (pCAG-GW-λN-3×FLAG-BSD vector) expressing human ΔRS-LBR, ΔTM-LBR, or full-length LBR construct from above. Endogenous LBR was knocked down by treating cells with siRNAs pool from Dharmacon (ON-TARGETplus SMARTpool siRNAs) targeting only mouse LBR, but not human LBR. It was ensured that the siRNAs targeted the mouse LBR specifically by ensuring that the human full-length LBR construct could rescue cells with knock down of endogenous LBR.

Generation of λN-3×FLAG Epitope Tagged Proteins.

Figure 35A:
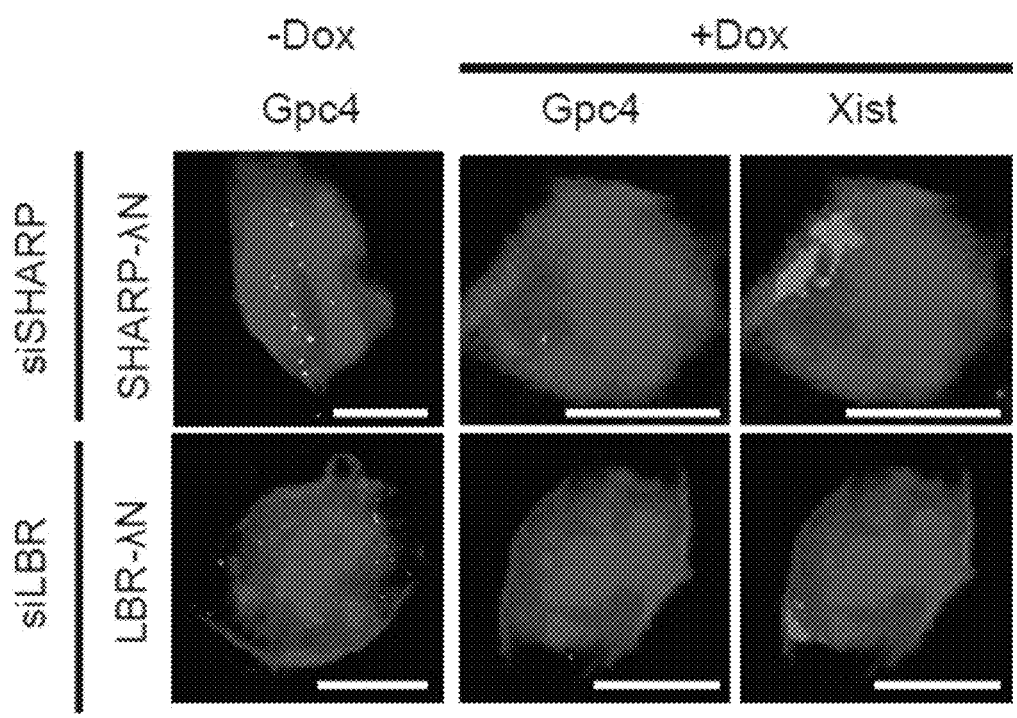
FIG. 35A show representative images of individual cells for Gpc4 mRNAs (green) and Xist (red) along with DAPI (blue) in cells expressing SHARP-λN-3×FLAG or LBR-λN-3×FLAG with SHARP or LBR knock down, with the number of identified mRNAs is shown, scale bars: 5 micrometers, according to embodiments of the present invention.
Figure 35B:
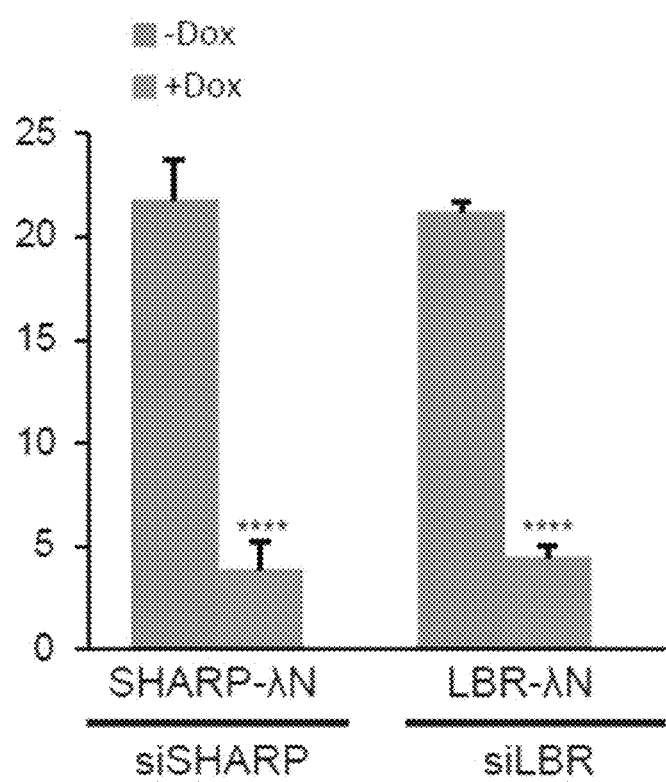
FIG. 35B is a graph plotting the quantification of the copy number of Gpc4 mRNA for −Dox and +Dox cells expressing SHARP-λN-3×FLAG or LBR-λN-3×FLAG upon SHARP or LBR knock down, with error bars representing the SEM across 50 individual cells, *** p-value<0.001 relative to −Dox cells by an unpaired two-sample t-test, according to embodiments of the present invention.

For λN-3×FLAG-tagged protein expression and immunoprecipitation, mouse ES cells were electroporated using the Neon transfection system (Invitrogen) with mammalian expression vector (pCAG-GW-λN-3×FLAG-BSD) encoding expression of a C-terminal λN-3×FLAG tagged ORF driven by CAG. Human ORFs of GFP, LBR, SHARP, EED1 and LMNB1 were obtained from the DNASU plasmid repository as Gateway entry clones and inserted into pCAG-GW-λN-3×FLAG-BSD using an LR recombination reaction (Invitrogen). Transfected cells were selected on 4 ug/mL Blasticidin (InvivoGen) to enrich for cells expressing tagged proteins For LBR-MCP, ORF of LBR was inserted into Ef1a-GW-MCP-V5-Neo vector using an LR recombination reaction (Invitrogen) and selected with 200 ug/mL Geneticin/G418 (Invitrogen). For analysis, immunofluorescence staining was used with antibodies against 3×FLAG or V5 epitope (described below) to select for cells expressing tagged proteins. λN-3×FLAG tagged proteins were verified as still functional by ensuring that they could rescue deletion of the endogenous protein (FIGS. 35A-35B).

Single Molecule RNA FISH.

Single molecule RNA Fluorescence in situ hybridization (FISH) experiments were done using QuantiGene ViewRNA ISH Cell Assay (Affymetrix) and QuantiGene ViewRNA ISH Cell 740 Module (Affymetrix) according to manufacturer's protocol. Cells fixed on coverslips were first permeabilized with Detergent Solution QC at room temperature for 5 min, and then incubated with desired mixture of probe set (Affymetrix) in Probe Set Diluent QF at 40° C. for 3 h, followed by incubated with PreAmplifier Mix at 40° C. for 30 min, Amplifier Mix at 40° C. for 30 min, and Label Probe Mix at 40° C. for 30 min sequentially. For DAPI staining, coverslips were incubated in 30 nM DAPI in PBS at room temperature for 15-20 min. Probe set and conjugated fluorophore for FISH were TYPE 1-XIST (550 nm), TYPE 4-GPC4 (488 nm), TYPE 10-ATRX (740 nm), and TYPE 6-SHARP, LBR, LMNB1, EMD (650 nm).

Immunofluorescence and RNA FISH.

For immunofluorescence (IF), cells were fixed on coverslips and permeabilized with 0.1% Triton-X in PBS at room temperature for 10 min, and blocked with 5% normal goat serum in PBS at room temperature for 10 min. Cells were then incubated with primary antibodies at room temperature for 1 h, followed by incubating with secondary antibodies at room temperature for 1 h. The samples were then processed using the RNA FISH protocol, as described above. Primary antibodies and the dilution used for IF were anti-Lamin B1 (Abcam; ab16048) (1:100), and anti-FLAG® M2 (Sigma-Aldrich; F1804) (1:100). Secondary antibodies and the dilution used for IF were Alexa Fluor® 488 F(ab')2 fragment of goat anti-rabbit IgG (H+L) (Life Technology; 1618692) (1:100) and highly x-ads DyLight® 650 goat anti-Rabbit IgG (H&L) (Bethyl; A120-201D5).

Microscopic Imaging.

FISH and IF/FISH samples were imaged using a Leica DMI 6000 Deconvolution Microscope with the Leica HC PL APO 63×/1.30 GLYC CORR CS2 objective. Samples stained with TYPE 10-ATRX (740 nm) were imaged using Nikon Ti Eclipse with the Nikon CFI Plan Apochromat λ DM 60×/1.40 oil objective. Images were projected with maximum projection (3 μm; step size, 0.2 μm).

X-Chromosome Silencing Assay.

Cells were stained for Xist RNA, Gpc4 mRNA, Atrx mRNA and siRNA-targeted mRNA by FISH and imaged. Images were then analyzed using Matlab R2013b (described below). Cells were selected if the copy number of the targeted mRNA was less than 30% of the level of the no siRNA treated cells and if they induced Xist expression. Within these cells, the copy number of Gpc4 mRNA and Atrx mRNA were quantified using a peak finding method (described below) and compared across conditions. mRNA levels for 50 individual cells were quantified. Xist expression was also evaluated in siRNA-treated cells, and no difference was observed in the percentage of cells that induced Xist expression in any of the siRNA conditions relative to untreated cells.

Quantifying mRNAs by Single Molecule FISH.

All image analysis was carried out using Matlab (version R2013b) utilizing built-in functions from the Image Processing toolbox. Images were first filtered using a two-dimensional median filter to remove background. Cell boundaries were outlined manually, guided by DAPI staining, to create a binary mask and applied to the various channels from the same field of view. Top-hat morphological filtering, a background subtraction method that enhances the individual focal spots, was applied to the images, Theodosiou et al., 2007, supra. The spots were then identified using a 2D peak finding algorithm that identifies local maximal signals within the cell. Once regional maxima were identified, the number of spots was counted for each cell.

Calculating Distance Between Xist Cloud and Lamin B1.

The nuclei of individual cells were identified manually using the DAPI staining. The Xist cloud, Lamin B1 region and nuclear area were identified by using an intensity-based threshold to partition the image within the nucleus and find contiguous 2-dimensional regions of high intensity. The threshold was determined based on Otsu method as previously described in Fumagalli et al., 2012, *Nat. Cell. Biol.* 14:355-365, the entire content of which is incorporated herein by reference, which splits the image into 2 bins—high and low—and identifies a threshold that minimizes the variance within the partition. This creates a binary mask on the image. With visual confirmation this binary mask accurately reflected the Xist cloud and Lamin B1 region. The distance between Xist cloud and Lamin B1 was determined by calculating the distance of each pixel between Xist cloud and Lamin B1 and finding the minimum value with a customized Fiji macro script. The area of the nucleus (Area) was measured using Fiji, and the radius of the nucleus (r) was calculated using $r=\sqrt{(Area/\pi)}$. The distance was set as zero if the Lamin B1 fluorescence signal overlapped with the fluorescence signal detect for the Xist compartment.

Calculating Distance Between Xist Cloud and Genomic Loci.

Nuclear area and Xist cloud were identified using the method described above. Genomic loci were determined by RNA FISH with probes against the intronic region of the genes using smFISH as described above (TYPE 4-GPC4 (Intron1), NOTCH2 (Intron1) and XIST (Intron1) (488 nm)). The spot was identified with Analyze Particle function in Fiji and selecting the spot with highest fluorescent intensity within the nucleus. The small number of images that contained more than one spot (for XIST and GPC4) or two spots (for NOTCH2) were discarded. For XIST and GPC4 locus, distance between Xist cloud and the locus was determined by finding the minimum distance between Xist cloud and the locus with a customized Fiji macro script described above. For NOTCH2 loci, distance between Xist cloud and the loci was determined by averaging the minimum distance between Xist cloud and the two loci.

The loci were identified as inside the Xist cloud if the fluorescence signal of the locus overlapped with these fluorescence signal for Xist (for XIST and GPC4) or the fluorescence signal of either one of the two loci overlapped with the fluorescence signal from the Xist compartment (for NOTCH2).

RNA antisense purification (RAP).

10 million mouse ES cells with 6 hours doxycycline induction were prepared and Xist RNA was captured and purified as described in Engreitz et al., 2013, supra. For Xist RNA capture, antisense 5' biotinylated 90-mer DNA oligonucleotides (Eurofins Operon) were used that spanned the entire length of the Xist RNA as previously described (23). To elute captured DNA, the beads were incubated with 15 U RNase H in 20 uL RNase H buffer (NEB Biolabs) at 37° C. for 1 hour. The RNase H digested samples were then transferred to a new tube. To reverse crosslinks, 25 uL Hybridization Buffer (20 mM Tris-HCl (pH 7.5), 7 mM EDTA, 3 mM EGTA, 150 mM LiCl, 1% NP-40, 0.2% N-lauroylsarcosine, 0.125% Na-Deoxycholate, 3M Guanidinium Thiocyanate, 2.5 mM TCEP), 125 uL NLS Elution Buffer (20 mM Tris-HCl (pH 7.5), 10 mM EDTA, 2% N-lauroylsarcosine, 2.5 mM TCEP), 500 mM NaCl and 4 U Protease K (NEB Biolabs, Molecular Biology Grade) was added and incubated at 60° C. overnight. Eluted DNA was sequenced, aligned and analyzed as described in Engreitz et al., 2013, supra, and Engreitz et al., 2014, Cell, 159:188-189, the entire content of which is incorporated herein by reference.

Aggregate Gene Analysis.

The Xist enrichments were averaged in 500 bp windows for the 100 Kb upstream and downstream of a gene, the 10 Kb starting at the beginning and end of a gene, and the 20 Kb centered at the middle of a gene. Genes within 5 Mb of the Xist transcription locus were excluded from the analysis because they represent outliers in terms of average Xist enrichment. The plots were generated and visualized using DeepTools and Gviz. The "active" and "inactive" genes were defined as described in Engreitz et al., 2013, supra. Expression levels were split based on RPKM levels computed from chromatin RNA-Seq levels as described Engreitz et al., 2014, supra. Only the genes with RPKM expression greater than 1 were considered. Genes with RPKM expression greater than 5 are grouped as highly actively transcribed genes.

Example 18

Materials and Methods for Reactivation in MLF Cells FIGS. 7A-7D

Mouse MLF Cell Culture and Inhibitor Treatment.

5,000 Mouse MLF cells were plated on a poly-D-lysine (Sigma) and 0.2% gelatin (Sigma)-coated #1.5 coverslip placed into wells of a 24-well plate containing HEK media (DMEM, 10% Gemini Benchmark FBS, 1×L-glutamine, 1× sodium pyruvate, 1×NEAA, 1× Pen/Strep; Life Technologies unless otherwise indicated). After 16 hours, inhibitors were added into the media and incubated the cells for 48 hours. The inhibitors and the concentration used were: 5-Azacytidine (6 μM; Sigma, A2385), 5-Aza-2'-deoxycytidine (0.3 M; Sigma, A3656), RG 108 (200 μM; Abcam, ab141013), Trichostatin A (5 μM; Sigma, T8552), and Scriptaid (100 nM; Sigma, S7817).

siRNA Transfection.

For siRNA knockdown experiments, 20 nM DNMT1 and HDAC3 siRNAs (Dharmacon, ON-TARGETplus SMARTpool siRNAs; HDAC siRNA: Catalog number: L-043553-02-0005; DNMT1 si RNA Catalog Number L-044147-01-0005) were mixed and transfected using the Neon transfection system (settings: 1200V, 40 ms width, 1 pulse). For each transfection, a 10 μL transfection with the siRNAs was carried out in succession using 100,000 cells, and plated on a poly-D-lysine (Sigma) and 0.2% gelatin (Sigma)-coated #1.5 coverslip placed into wells of a 24-well plate containing HEK media for 48 hours. For each cell analyzed, it was ensured that the siRNA successfully reduced the targeted mRNA expression by >70%.

Single Molecule RNA FISH.

Coverslips from siRNA transfection or inhibitor treatment were fixed in Histochoice (Sigma) for 10 min, washed thoroughly in PBS, and dehydrated in ethanol for storage until FISH staining. Single molecule RNA Fluorescence in situ hybridization (FISH) experiments were done using QuantiGene ViewRNA ISH Cell Assay (Affymetrix) and QuantiGene ViewRNA ISH Cell 740 Module (Affymetrix) according to manufacturer's protocol. Specifically, cells fixed on coverslips were first permeabilized with Detergent Solution QC at room temperature for 5 min, and then incubated with desired mixture of probe set (Affymetrix) in Probe Set Diluent QF at 40° C. for 3 h, followed by incubated with PreAmplifier Mix at 40° C. for 30 min, Amplifier Mix at 40° C. for 30 min, and Label Probe Mix at 40° C. for 30 min sequentially. For DAPI staining, coverslips were incubated in 30 nM DAPI in PBS at room temperature for 15-20 min. Probe sets and conjugated fluorophores (excitation wavelengths) for FISH were TYPE 4-GPC4, MECP2, SMC1A (488 nm), TYPE 10-ATRX (740 nm), and TYPE 6-EMD (650 nm).

Microscopic Imaging.

FISH samples were imaged using a Leica DMI 6000 Deconvolution Microscope with the Leica HC PL APO 63×/1.30 GLYC CORR CS2 objective. Samples stained with TYPE 10-ATRX (740 nm) were imaged using Nikon Ti Eclipse with the Nikon CFI Plan Apochromat λ DM 60×/1.40 oil objective. Images were projected with maximum projection (3 μm; step size, 0.2 μm). Samples for 3D deconvolution was imaged using Leica DMI 6000 Deconvolution Microscope with the Leica HC PL APO 63×/1.30 GLYC CORR CS2 objective (15 μm; 0.02 μm step size).

X-Chromosome Reactivation Assay.

Cells were stained for target mRNAs and siRNA-targeted mRNA by FISH and imaged. Images were then analyzed using Matlab R2013b (described below). In the case of siRNA targeting, cells were selected if the copy number of the targeted mRNA was less than 30% of the level of the no siRNA treated cells and if they induced Xist expression. Within these cells, the copy number of target mRNAs were quantified using a peak finding method (described below) and compared across conditions. The mRNA levels were quantified for 50 individual cells.

Quantifying mRNAs by Single Molecule FISH.

All image analysis was carried out using Matlab (version R2013b) utilizing built-in functions from the Image Processing toolbox. Images were first filtered using a two-dimensional median filter to remove background. Cell boundaries were outlined manually, guided by DAPI staining, to create a binary mask and applied to the various channels from the same field of view. Top-hat morphological filtering, a background subtraction method that enhances the individual focal spots, was applied to the images. The spots were then identified using a 2D peak finding algorithm that identifies local maximal signals within the cell. Once regional maxima were identified, the number of spots was counted for each cell. The percentage of X-reactivation is calculated by normalizing the average number of spots of each condition to the average number of spots in untreated cells, and subtracting the value by 1.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method of prohibiting Xist-dependent silencing of at least one Xist-dependent X chromosome gene or of prohibiting Xist-dependent silencing of an Xist-dependent autosome gene, the method comprising:

providing an isolated stem cell comprising the at least one Xist-dependent X chromosome gene or the Xist-dependent autosome gene; and administering a molecule that inhibits HDAC3 and a molecule that inhibits DNA methylation to the isolated stem cell; and measuring expression activity of the at least one Xist-dependent X chromosome gene or the Xist-dependent autosome gene in the isolated stem cell, wherein the molecule that inhibits HDAC3 is an HDAC3-specific inhibitor and is not a pan-HDAC inhibitor.

2. The method of claim 1, wherein the molecule that inhibits HDAC3 comprises a HDAC3 small interfering RNA (siRNA).

3. The method of claim 1, wherein the molecule that inhibits HDAC3 is selected from the group consisting of Cas9, dCas9, TALENS, zinc-finger nucleases, and nucleases targeted to a gene encoding for HDAC3.

4. A method of reactivating expression of at least one Xist-dependent silenced X chromosome gene or a silenced Xist-dependent autosome gene in an isolated stem cell comprising at least one Xist-dependent silenced X chromosome gene or Xist-dependent silenced autosomal gene, comprising:
   targeting the Xist interaction with HDAC3 to reactivate expression of the at least one Xist-dependent silenced X chromosome gene or the silenced Xist-dependent autosome gene in the isolated stem cell; and
   administering an HDAC3-specific inhibitor and a DNA methylation inhibitor to the isolated stem cell, wherein the HDAC3-specific inhibitor reactivates expression of the at least one Xist-dependent silenced X chromosome gene or the silenced Xist-dependent autosome gene; and
   measuring expression activity of the at least one Xist-dependent X chromosome gene or the Xist-dependent autosome gene in the isolated stem cell;
   wherein the HDAC3-specific inhibitor is not a pan-HDAC inhibitor.

5. A method of prohibiting Xist-dependent silencing of at least one Xist-dependent X chromosome gene or of prohibiting Xist-dependent silencing of an Xist-dependent autosome gene in an isolated stem cell, the method comprising:
   identifying a molecule as capable of prohibiting Xist-dependent silencing of X chromosome genes or an Xist-dependent autosome gene, wherein the molecule is an HDAC3-specific inhibitor; and
   administering the HDAC3-specific inhibitor and a DNA methylation inhibitor to the isolated stem cell, wherein the HDAC3-specific inhibitor prohibits Xist-dependent silencing; and
   measuring expression activity of the at least one Xist-dependent X chromosome gene or the Xist-dependent autosome gene in the isolated stem cell;
   wherein the HDAC3-specific inhibitor is not a pan-HDAC inhibitor.

6. The method of claim 5, wherein the HDAC3-specific inhibitor comprises HDAC3 siRNA.

7. The method of claim 1, wherein the at least one Xist-dependent X chromosome gene or the Xist-dependent autosome gene comprises Gpc4 or Atrx, or both.

8. The method of claim 1, wherein measuring expression activity of the at least one Xist-dependent X chromosome gene or the Xist-dependent autosome gene is selected from:
   measuring chromatin modification states of active or repressed transcription of the at least one Xist-dependent X chromosome gene or the Xist-dependent autosome gene, or measuring RNA Polymerase II levels of the at least one Xist-dependent X chromosome gene or the Xist-dependent autosome gene, or
   measuring transcription, mRNA levels, or protein expression levels of the at least one X chromosome gene or Xist-dependent autosome gene.

9. The method of claim 4, wherein measuring expression activity of the at least one Xist-dependent X chromosome gene or the Xist-dependent autosome gene is selected from:
   measuring chromatin modification states of active or repressed transcription of the at least one Xist-dependent X chromosome gene or the Xist-dependent autosome gene, or measuring RNA Polymerase II levels of the at least one Xist-dependent X chromosome gene or the Xist-dependent autosome gene, or
   measuring transcription, mRNA levels, or protein expression levels of the at least one X chromosome gene or Xist-dependent autosome gene.

10. The method of claim 5, wherein measuring expression activity of the at least one Xist-dependent X chromosome gene or the Xist-dependent autosome gene is selected from:
   measuring chromatin modification states of active or repressed transcription of the at least one Xist-dependent X chromosome gene or the Xist-dependent autosome gene, or measuring RNA Polymerase II levels of the at least one Xist-dependent X chromosome gene or the Xist-dependent autosome gene, or
   measuring transcription, mRNA levels, or protein expression levels of the at least one X chromosome gene or Xist-dependent autosome gene.

* * * * *

SEQUENCE LISTING

<160> NUMBER OF SEQ ID NOS: 12

<210> SEQ ID NO 1
<211> LENGTH: 19
<212> TYPE: RNA
<213> ORGANISM: artificial
<220> FEATURE:
<223> OTHER INFORMATION: D1 Spen siRNA

<400> SEQUENCE: 1
cgagagggag agacgaaua                                                    19

<210> SEQ ID NO 2
<211> LENGTH: 19
<212> TYPE: RNA
<213> ORGANISM: artificial
<220> FEATURE:
<223> OTHER INFORMATION: D2 Spen siRNA

<400> SEQUENCE: 2
cuaaagagcc ggagccgaa                                                    19

<210> SEQ ID NO 3
<211> LENGTH: 19
<212> TYPE: RNA
<213> ORGANISM: artificial
<220> FEATURE:
<223> OTHER INFORMATION: D3 Spen siRNA

<400> SEQUENCE: 3
ccuaaaauca cgucgguua                                                    19

<210> SEQ ID NO 4
<211> LENGTH: 19
<212> TYPE: RNA
<213> ORGANISM: artificial
<220> FEATURE:
<223> OTHER INFORMATION: D4 Spen siRNA

<400> SEQUENCE: 4
ggaaacaccu caaggccga                                                    19

<210> SEQ ID NO 5
<211> LENGTH: 19
<212> TYPE: RNA
<213> ORGANISM: artificial
<220> FEATURE:
<223> OTHER INFORMATION: D1 Lbr siRNA

<400> SEQUENCE: 5
uguugaagcc guucggaaa                                                    19

<210> SEQ ID NO 6
<211> LENGTH: 19
<212> TYPE: RNA
<213> ORGANISM: artificial
<220> FEATURE:
<223> OTHER INFORMATION: D2 Lbr siRNA

<400> SEQUENCE: 6
auacaaagau ggcaccgaa                                                    19

<210> SEQ ID NO 7
<211> LENGTH: 19
<212> TYPE: RNA
<213> ORGANISM: artificial

-continued

```
<220> FEATURE:
<223> OTHER INFORMATION: D3 Lbr siRNA

<400> SEQUENCE: 7
auaaacacau agacgacuu                                                  19

<210> SEQ ID NO 8
<211> LENGTH: 20
<212> TYPE: DNA
<213> ORGANISM: artificial
<220> FEATURE:
<223> OTHER INFORMATION: 3' Xist guide RNA

<400> SEQUENCE: 8
cctcatcctc atgtcttctc                                                 20

<210> SEQ ID NO 9
<211> LENGTH: 20
<212> TYPE: DNA
<213> ORGANISM: artificial
<220> FEATURE:
<223> OTHER INFORMATION: LBS-1 sgRNA 1

<400> SEQUENCE: 9
caccgaggag cacagcggac                                                 20

<210> SEQ ID NO 10
<211> LENGTH: 20
<212> TYPE: DNA
<213> ORGANISM: artificial
<220> FEATURE:
<223> OTHER INFORMATION: LBS-1 sgRNA 2

<400> SEQUENCE: 10
taaggacgtg agtttcgctt                                                 20

<210> SEQ ID NO 11
<211> LENGTH: 17
<212> TYPE: DNA
<213> ORGANISM: artificial
<220> FEATURE:
<223> OTHER INFORMATION: LBR transcription start sgRNA

<400> SEQUENCE: 11
cgggactccg ccgcgtg                                                    17

<210> SEQ ID NO 12
<211> LENGTH: 18
<212> TYPE: DNA
<213> ORGANISM: artificial
<220> FEATURE:
<223> OTHER INFORMATION: SHARP transcription start sgRNA

<400> SEQUENCE: 12
cggtggcgtc ggcagcgg                                                   18
```